United States Patent [19]
Fiers et al.

[11] Patent Number: 5,652,353
[45] Date of Patent: Jul. 29, 1997

[54] DNAS ENCODING TUMOR NECROSIS FACTOR-α MUTEINS

[75] Inventors: Walter Fiers, Destelbergen; Jan Tavernier, Balegem; Xaveer Van Ostade, Antwerp, all of Belgium

[73] Assignee: Hoffman-La Roche Inc., Nutley, N.J.

[21] Appl. No.: 397,470

[22] Filed: Mar. 1, 1995

Related U.S. Application Data

[62] Division of Ser. No. 794,400, Nov. 20, 1991, Pat. No. 5,422,104.

[30] Foreign Application Priority Data

Nov. 21, 1990 [EP] European Pat. Off. ............ 90810901

[51] Int. Cl.$^6$ .................. C12N 15/28; C07K 14/525
[52] U.S. Cl. ................ 536/23.5; 435/69.5; 435/172.3; 435/252.3; 435/320.1; 935/11; 935/22; 935/70; 935/73
[58] Field of Search ................ 536/23.1, 23.5; 435/69.5, 172.3, 260.2, 252.3, 320.1, 71.1, 71.2; 935/11, 27, 29, 52, 66, 72, 73; 530/358

[56] References Cited

U.S. PATENT DOCUMENTS

| | | | |
|---|---|---|---|
| 4,650,674 | 3/1987 | Aggarwal et al. | 424/85 |
| 4,948,875 | 8/1990 | Tanaku et al. | 530/350 |
| 4,990,455 | 2/1991 | Yamagishi et al. | 435/69.5 |

FOREIGN PATENT DOCUMENTS

| | | |
|---|---|---|
| B-44652/85 | 7/1985 | Australia . |
| 40162 | 12/1989 | Australia . |
| 0 168 214 | 1/1986 | European Pat. Off. . |
| 3843534 | 7/1990 | Germany . |
| 61/40221 | 2/1986 | Japan . |
| 63/291590 | 11/1988 | Japan . |
| 88/06625 | 9/1988 | WIPO . |

OTHER PUBLICATIONS

English Abstract for Document B7.
English Abstract for Document B6 (J63/91590).
Tsujimoto, et al. J. Biochem. 101, 919–925 (1987).
Masegi, et al. Protein Engineering 375–376 (1989).
Yamagishi, et al. Protein Engineering, vol. 3, No. 8, 713–719 (1990).
Tsukio, Patent Abstract of Japan, vol. 13, No. 119 (1989).
Ostade, et al. The Embo Journal, vol. 10, No. 4 827–836 (1991).
Tartaglia, et al, Immunology Today, vol. 13, No. 5, (1992).
Barrett, et al. Eur. Journal Immunology vol. 21, 1649–1656 (1991).
Lewis, et al. Proc. Natl. Acad. Science vol. 88, 2830–2834 (1991).
Yamagishi, et al. Protein Eng. 3(4) 372 (abst. only) (1990).
Wills, et al. Science 243, 1330–1336 (1989).
Goh, et al. Protein Eng. 4 (7) 785–791 (1991).
Zavernier, et al. J. Mol. Biol. 211(2) 493–502 (1990).
Eck et al, JBC, 264 17595–06, (1989).
Bowie et al. (1990) Science, vol. 247, pp. 1306–1310.

*Primary Examiner*—John Ulm
*Assistant Examiner*—Prema Mertz
*Attorney, Agent, or Firm*—George W. Johnston; William H. Epstein; Lewis J. Kreisler

[57] ABSTRACT

It is an object of this invention to provide a human Tumor Necrosis Factor mutein or a pharmaceutically acceptable salt thereof characterized in that the TNF sequence is changed by a deletion, insertion, substitution or combinations thereof, of one or more amino acids so that the mutein shows a significant difference between its binding affinity to the human p75-Tumor-Necrosis-Factor-Receptor and to the human p55-Tumor-Necrosis-Factor-Receptor. The invention also includes DNA sequences coding for such muteins, vectors comprising such DNA sequences, host cells transformed with such vectors and a process for the production of such muteins employing such transformed host cells and pharmaceutical compositions containing such muteins and their use for the treatment of illnesses, for example cancer.

4 Claims, 18 Drawing Sheets

HindIII
```
   1 AAGCTTCACG CTGCCGCAAG CACTCAGGGC GCAAGGGCTG CTAAAGGAAG
  51 CGGAACACGT AGAAAGCCAG TCCGCAGAAA CGGTGCTGAC CCCGGATGAA
 101 TGTCAGCTAC TGGGCTATCT GGACAAGGGA AAACGCAAGC GCAAAGAGAA
 151 AGCAGGTAGC TTGCAGTGGG CTTACATGGC GATAGCTAGA CTGGGCGGTT
 201 TTATGGACAG CAAGCGAACC GGAATTGCCA GCTGGGGCGC CCTCTGGTAA
 251 GGTTGGGAAG CCCTGCAAAG TAAACTGGAT GGCTTTCTTG CCGCCAAGGA
 301 TCTGATGGCG CAGGGGATCA AGATCTGATC AAGAGACAGG ATGACGGTCG
 351 TTTCGCATGC TTGAACAAGA TGGATTGCAC GCAGGTTCTC CGGCCGCTTG
 401 GGTGGAGAGG CTATTCGGCT ATGACTGGGC ACAACAGACA ATCGGCTGCT
 451 CTGATGCCGC CGTGTTCCGG CTGTCAGCGC AGGGGCGCCC GGTTCTTTTT
 501 GTCAAGACCG ACCTGTCCGG TGCCCTGAAT GAACTGCAGG ACGAGGCAGC
 551 GCGGCTATCG TGGCTGGCCA CGACGGGCGT TCCTTGCGCA GCTGTGCTCG
 601 ACGTTGTCAC TGAAGCGGGA AGGGACTGGC TGCTATTGGG CGAAGTGCCG
 651 GGGCAGGATC TCCTGTCATC TCACCTTGCT CCTGCCGAGA AAGTATCCAT
 701 CATGGCTGAT GCAATGCGGC GGCTGCATAC GCTTGATCCG GCTACCTGCC
 751 CATTCGACCA CCAAGCGAAA CATCGCATCG AGCGAGCACG TACTCGGATG
 801 GAAGCCGGTC TTGTCGATCA GGATGATCTG GACGAAGAGC ATCAGGGGCT
 851 CGCGCCAGCC GAACTGTTCG CCAGGCTCAA GGCGCGCATG CCCGACGGCG
 901 AGGATCTCGT CGTGACCCAT GGCGATGCCT GCTTGCCGAA TATCATGGTG
 951 GAAAATGGCC GCTTTTCTGG ATTCATCGAC TGTGGCCGGC TGGGTGTGGC
1001 GGACCGCTAT CAGGACATAG CGTTGGCTAC CCGTGATATT GCTGAAGAGC
1051 TTGGCGGCGA ATGGGCTGAC CGCTTCCTCG TGCTTTACGG TATCGCCGCT
1101 CCCGATTCGC AGCGCATCGC CTTCTATCGC CTTCTTGACG AGTTCTTCTG
1151 AGCGGGACTC TGGGGTTCGA AATGACCGAC CAAGCGACGC CCAACCTGCC
1201 ATCACGAGAT TTCGATTCCA CCGCCGCCTT CTATGAAAGG TTGGGCTTCG
1251 GAATCGTTTT CCGGGACGCC GGCTGGATGA TCCTCCAGCG CGGGGATCTC
1301 ATGCTGGAGT TCTTCGCCCA CCCCGGGCTC GATCCCCTCG CGAGTTGGTT
```

*FIG. 4A*

1351 CAGCTGCTGC CTGAGGCTGG ACGACCTCGC GGAGTTCTAC CGGCAGTGCA

1401 AATCCGTCGG CATCCAGGAA ACCAGCAGCG GCTATCCGCG CATCCATGCC

Sal I

1451 CCCGAACTGC AGGAGTGGGG AGGCACGATG GCCGCTTTGG TCGACAATTC

1501 GCGCTAACTT ACATTAATTG CGTTGCGCTC ACTGCCCGCT TTCCAGTCGG

1551 GAAACCTGTC GTGCCAGCTG CATTAATGAA TCGGCCAACG CGCGGGGAGA

1601 GGCGGTTTGC GTATTGGGCG CCAGGGTGGT TTTTCTTTTC ACCAGTGAGA

1651 CGGGCAACAG CTGATTGCCC TTCACCGCCT GGCCCTGAGA GAGTTGCAGC

1701 AAGCGGTCCA CGCTGGTTTG CCCCAGCAGG CGAAAATCCT GTTTGATGGT

1751 GGTTAACGGC GGGATATAAC ATGAGCTGTC TTCGGTATCG TCGTATCCCA

1801 CTACCGAGAT ATCCGCACCA ACGCGCAGCC CGGACTCGGT AATGGCGCGC

1851 ATTGCGCCCA GCGCCATCTG ATCGTTGGCA ACCAGCATCG CAGTGGGAAC

1901 GATGCCCTCA TTCAGCATTT GCATGGTTTG TTGAAAACCG GACATGGCAC

1951 TCCAGTCGCC TTCCCGTTCC GCTATCGGCT GAATTTGATT GCGAGTGAGA

2001 TATTTATGCC AGCCAGCCAG ACGCAGACGC GCCGAGACAG AACTTAATGG

2051 GCCCGCTAAC AGCGCGATTT GCTGGTGACC CAATGCGACC AGATGCTCCA

2101 CGCCCAGTCG CGTACCGTCT TCATGGGAGA AAATAATACT GTTGATGGGT

2151 GTCTGGTCAG AGACATCAAG AAATAACGCC GGAACATTAG TGCAGGCAGC

2201 TTCCACAGCA ATGGCATCCT GGTCATCCAG CGGATAGTTA ATGATCAGGC

2251 CACTGACGCG TTGCGCGAGA AGATTGTGCA CCGCCGCTTT ACAGGCTTCG

2301 ACGCCGCTTC GTTCTACCAT CGACACCACC ACGCTGGCAC CCAGTTGATC

2351 GGCGCGAGAT TAATCGCCG CGACAATTTG CGACGGCGCG TGCAGGGCCA

2401 GACTGGAGGT GGCAACGCCA ATCAGCAACG ACTGTTTGCC CGCCAGTTGT

2451 TGTGCCACGC GGTTGGGAAT GTAATTCAGC TCCGCCATCG CCGCTTCCAC

2501 TTTTTCCCGC GTTTTCGCAG AAACGTGGCT GGCCTGGTTC ACCACGCGGG

2551 AAACGGTCTG ATAAGAGACA CCGGCATACT CTGCGACATC GTATAACGTT

2601 ACTGGTTTCA CATTCACCAC CCTGAATTGA CTCTCTTCCG GGCGCTATCA

2651 TGCCATACCG CGAAAGGTTT TGCGCCATTC GATGGTGTCA ACGTAAATGC

Sal I

2701 ATGCCGCTTC GCCTTCGCGC GCGAATTGTC GACCCTGTCC CTCCTGTTCA

FIG. 4B

2751 GCTACTGACG GGGTGGTGCG TAACGGCAAA AGCACCGCCG GACATCAGCG

2801 CTAGCGGAGT GTATACTGGC TTACTATGTT GGCACTGATG AGGGTGTCAG

2851 TGAAGTGCTT CATGTGGCAG GAGAAAAAAG GCTGCACCGG TGCGTCAGCA

2901 GAATATGTGA TACAGGATAT ATTCCGCTTC CTCGCTCACT GACTCGCTAC

2951 GCTCGGTCGT TCGACTGCGG CGAGCGGAAA TGGCTTACGA ACGGGGCGGA

3001 GATTTCCTGG AAGATGCCAG GAAGATACTT AACAGGGAAG TGAGAGGGCC

3051 GCGGCAAAGC CGTTTTTCCA TAGGCTCCGC CCCCCTGACA AGCATCACGA

3101 AATCTGACGC TCAAATCAGT GGTGGCGAAA CCCGACAGGA CTATAAAGAT

3151 ACCAGGCGTT TCCCCTGGCG GCTCCCTCGT GCGCTCTCCT GTTCCTGCCT

3201 TTCGGTTTAC CGGTGTCATT CCGCTGTTAT GGCCGCGTTT GTCTCATTCC

3251 ACGCCTGACA CTCAGTTCCG GGTAGGCAGT TCGCTCCAAG CTGGACTGTA

3301 TGCACGAACC CCCCGTTCAG TCCGACCGCT GCGCCTTATC CGGTAACTAT

3351 CGTCTTGAGT CCAACCCGGA AAGACATGCA AAAGCACCAC TGGCAGCAGC

3401 CACTGGTAAT TGATTTAGAG GAGTTAGTCT TGAAGTCATG CGCCGGTTAA

3451 GGCTAAACTG AAAGGACAAG TTTTGGTGAC TGCGCTCCTC CAAGCCAGTT

3501 ACCTCGGTTC AAAGAGTTGG TAGCTCAGAG AACCTTCGAA AAACCGCCCT

3551 GCAAGGCGGT TTTTTCGTTT TCAGAGCAAG AGATTACGCG CAGACCAAAA

3601 CGATCTCAAG AAGATCATCT TATTAATCAG ATAAAATATT TCTAGATTTC

3651 AGTGCAATTT ATCTCTTCAA ATGTAGCACC TGAAGTCAGC CCCATACGAT

3701 ATAAGTTGTT AATTCTCATG TTTGACAGCT TATCATCGAT

*FIG. 4C*

```
     XhoI
   1 CTCGAGAAAT CATAAAAAAT TTATTTGCTT TGTGAGCGGA TAACAATTAT
                                                EcoRI
  51 AATAGATTCA ATTGTGAGCG GATAACAATT TCACACAGAA TTCATTAAAG
 101 AGGAGAAATT AAGCATGGTC AGATCATCTT CTCGAACCCC GAGTGACAAG
 151 CCTGTAGCCC ATGTTGTCGC GAACCCTCAA GCTGAGGGGC AGCTCCAGTG
 201 GCTGAACCGC CGGGCCAATG CCCTCCTGGC CAATGGCGTG GAGCTGAGAG
 251 ATAACCAGCT GGTGGTGCCA TCAGAGGGCC TGTACCTCAT CTACTCCCAG
 301 GTCCTCTTCA AGGGCCAAGG CTGCCCCTCC ACCCATGTGC TCCTCACCCA
 351 CACCATCAGC CGCATCGCCG TCTCCTACCA GACCAAGGTC AACCTCCTCT
 401 CTGCCATCAA GAGCCCCTGC CAGAGGGAGA CCCCAGAGGG GGCTGAGGCC
 451 AAGCCCTGGT ATGAGCCCAT CTATCTGGGA GGGGTCTTCC AGCTGGAGAA
 501 GGGTGACCGA CTCAGCGCTG AGATCAATCG GCCCGACTAT CTCGACTTTG
 551 CCGAGTCTGG GCAGGTCTAC TTTGGGATCA TTGCCCTGTG AGGAGGACGA
 601 ACATCCAACC TTCCCAAACG CCTCCCCTGC CCCAATCCCT TTATTACCCC
 651 CTCCTTCAGA CACCCTCAAC CTCTTCTGGC TCAAAAGAG AATTGGGGGC
                HindIII
 701 TTAGGGTCGG AACCCAAGCT TGGACTCCTG TTGATAGATC CAGTAATGAC
 751 CTCAGAACTC CATCTGGATT TGTTCAGAAC GCTCGGTTGC CGCCGGGCGT
 801 TTTTTATTGG TGAGAATCCA AGCTAGCTTG GCGAGATTTT CAGGAGCTAA
 851 GGAAGCTAAA ATGGAGAAAA AAATCACTGG ATATACCACC GTTGATATAT
 901 CCCAATGGCA TCGTAAAGAA CATTTTGAGG CATTTCAGTC AGTTGCTCAA
 951 TGTACCTATA ACCAGACCGT TCAGCTGGAT ATTACGGCCT TTTTAAAGAC
1001 CGTAAAGAAA AATAAGCACA AGTTTTATCC GGCCTTTATT CACATTCTTG
1051 CCCGCCTGAT GAATGCTCAT CCGGAATTTC GTATGGCAAT GAAAGACGGT
1101 GAGCTGGTGA TATGGGATAG TGTTCACCCT TGTTACACCG TTTTCCATGA
1151 GCAAACTGAA ACGTTTTCAT CGCTCTGGAG TGAATACCAC GACGATTTCC
1201 GGCAGTTTCT ACACATATAT TCGCAAGATG TGGCGTGTTA CGGTGAAAAC
1251 CTGGCCTATT TCCCTAAAGG GTTTATTGAG AATATGTTTT TCGTCTCAGC
```

*FIG. 6A*

```
1301 CAATCCCTGG GTGAGTTTCA CCAGTTTTGA TTTAAACGTG GCCAATATGG

1351 ACAACTTCTT CGCCCCCGTT TTCACCATGG GCAAATATTA TACGCAAGGC

1401 GACAAGGTGC TGATGCCGCT GGCGATTCAG GTTCATCATG CCGTCTGTGA

1451 TGGCTTCCAT GTCGGCAGAA TGCTTAATGA ATTACAACAG TACTGCGATG

1501 AGTGGCAGGG CGGGGCGTAA TTTTTTTAAG GCAGTTATTG GTGCCCTTAA

1551 ACGCCTGGGG TAATGACTCT CTAGCTTGAG GCATCAAATA AAACGAAAGG

1601 CTCAGTCGAA AGACTGGGCC TTTCGTTTTA TCTGTTGTTT GTCGGTGAAC
                                    XbaI
1651 GCTCTCCTGA GTAGGACAAA TCCGCCGCTC TAGAGCTGCC TCGCGCGTTT

1701 CGGTGATGAC GGTGAAAACC TCTGACACAT GCAGCTCCCG GAGACGGTCA

1751 CAGCTTGTCT GTAAGCGGAT GCCGGGAGCA GACAAGCCCG TCAGGGCGCG

1801 TCAGCGGGTG TTGGCGGGTG TCGGGGCGCA GCCATGACCC AGTCACGTAG

1851 CGATAGCGGA GTGTATACTG GCTTAACTAT GCGGCATCAG AGCAGATTGT

1901 ACTGAGAGTG CACCATATGC GGTGTGAAAT ACCGCACAGA TGCGTAAGGA

1951 GAAAATACCG CATCAGGCGC TCTTCCGCTT CCTCGCTCAC TGACTCGCTG

2001 CGCTCGGTCT GTCGGCTGCG GCGAGCGGTA TCAGCTCACT CAAAGGCGGT

2051 AATACGGTTA TCCACAGAAT CAGGGGATAA CGCAGGAAAG AACATGTGAG

2101 CAAAAGGCCA GCAAAAGGCC AGGAACCGTA AAAAGGCCGC GTTGCTGGCG

2151 TTTTTCCATA GGCTCCGCCC CCTGACGAG CATCACAAAA ATCGACGCTC

2201 AAGTCAGAGG TGGCGAAACC CGACAGGACT ATAAAGATAC CAGGCGTTTC

2251 CCCCTGGAAG CTCCCTCGTG CGCTCTCCTG TTCCGACCCT GCCGCTTACC

2301 GGATACCTGT CCGCCTTTCT CCCTTCGGGA AGCGTGGCGC TTTCTCAATG

2351 CTCACGCTGT AGGTATCTCA GTTCGGTGTA GGTCGTTCGC TCCAAGCTGG

2401 GCTGTGTGCA CGAACCCCCC GTTCAGCCCG ACCGCTGCGC CTTATCCGGT

2451 AACTATCGTC TTGAGTCCAA CCCGGTAAGA CACGACTTAT CGCCACTGGC

2501 AGCAGCCACT GGTAACAGGA TTAGCAGAGC GAGGTATGTA GGCGGTGCTA

2551 CAGAGTTCTT GAAGTGGTGG CCTAACTACG GCTACACTAG AAGGACAGTA

2601 TTTGGTATCT GCGCTCTGCT GAAGCCAGTT ACCTTCGGAA AAAGAGTTGG

2651 TAGCTCTTGA TCCGGCAAAC AAACCACCGC TGGTAGCGGT GGTTTTTTTG
```

*FIG. 6B*

```
2701 TTTGCAAGCA GCAGATTACG CGCAGAAAAA AAGGATCTCA AGAAGATCCT
2751 TTGATCTTTT CTACGGGGTC CGCAGAAAAA TGGAACGAAA ACTCACGTTA
2801 AGGGATTTTG GTCATGAGAT TATCAAAAAG GATCTTCACC TAGATCCTTT
2851 TAAATTAAAA ATGAAGTTTT AAATCAATCT AAGTATATA TGAGTAAACT
2901 TGGTCTGACA GTTACCAATG CTTAATCAGT GAGGCACCTA TCTCAGCGAT
2951 CTGTCTATTT CGTTCATCCA TAGCTGCCTG ACTCCCCGTC GTGTAGATAA
3001 CTACGATACG GGAGGGCTTA CCATCTGGCC CCAGTGCTGC AATGATACCG
3051 CGAGACCCAC GCTCACCGGC TCCAGATTTA TCAGCAATAA ACCAGCCAGC
3101 CGGAAGGGCC GAGCGCAGAA GTGGTCCTGC AACTTTATCC GCCTCCATCC
3151 AGTCTATTAA TTGTTGCCGG GAAGCTAGAG TAAGTAGTTC GCCAGTTAAT
3201 AGTTTGCGCA ACGTTGTTGC CATTGCTACA GGCATCGTGG TGTCACGCTC
3251 GTCGTTTGGT ATGGCTTCAT TCAGCTCCGG TTCCCAACGA TCAAGGCGAG
3301 TTACATGATC CCCCATGTTG TGCAAAAAAG CGGTTAGCTC CTTCGGTCCT
3351 CCGATCGTTG TCAGAAGTAA GTTGGCCGCA GTGTTATCAC TCATGGTTAT
3401 GGCAGCACTG CATAATTCTC TTACTGTCAT GCCATCCGTA AGATGCTTTT
3451 CTGTGACTGG TGAGTACTCA ACCAAGTCAT TCTGAGAATA GTGTATGCGG
3501 CGACCGAGTT GCTCTTGCCC GGCGTCAATA CGGGATAATA CCGCGCCACA
3551 TAGCAGAACT TTAAAAGTGC TCATCATTGG AAAACGTTCT TCGGGGCGAA
3601 AACTCTCAAG GATCTTACCG CTGTTGAGAT CCAGTTCGAT GTAACCCACT
3651 CGTGCACCCA ACTGATCTTC AGCATCTTTT ACTTTCACCA GCGTTTCTGG
3701 GTGAGCAAAA ACAGGAAGGC AAAATGCCGC AAAAAAGGGA ATAAGGGCGA
3751 CACGGAAATG TTGAATACTC ATACTCTTCC TTTTTCAATA TTATTGAAGC
3801 ATTTATCAGG GTTATTGTCT CATGAGCGGA TACATATTTG AATGTATTTA
3851 GAAAAATAAA CAAATAGGGG TTCCGCGCAC ATTTCCCCGA AAAGTGCCAC
3901 CTGACGTCTA AGAAACCATT ATTATCATGA CATTAACCTA TAAAAATAGG
3951 CGTATCACGA GGCCCTTTCG TCTTCAC
```

FIG. 6C

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 157 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens
        ( F ) TISSUE TYPE: Blood
        ( G ) CELL TYPE: Macrophage ( x i ) SEQUENCE DESCRIPTION: SEQ ID NO:1:

```
Val  Arg  Ser  Ser  Ser  Arg  Thr  Pro  Ser  Asp  Lys  Pro  Val  Ala  His  Val
 1                  5                        10                       15

Val  Ala  Asn  Pro  Gln  Ala  Glu  Gly  Gln  Leu  Gln  Trp  Leu  Asn  Arg  Arg
               20                       25                       30

Ala  Asn  Ala  Leu  Leu  Ala  Asn  Gly  Val  Glu  Leu  Arg  Asp  Asn  Gln  Leu
          35                       40                       45

Val  Val  Pro  Ser  Glu  Gly  Leu  Tyr  Leu  Ile  Tyr  Ser  Gln  Val  Leu  Phe
     50                       55                       60

Lys  Gly  Gln  Gly  Cys  Pro  Ser  Thr  His  Val  Leu  Leu  Thr  His  Thr  Ile
 65                       70                       75                       80

Ser  Arg  Ile  Ala  Val  Ser  Tyr  Gln  Thr  Lys  Val  Asn  Leu  Leu  Ser  Ala
                    85                       90                       95

Ile  Lys  Ser  Pro  Cys  Gln  Arg  Glu  Thr  Pro  Glu  Gly  Ala  Glu  Ala  Lys
               100                      105                      110

Pro  Trp  Tyr  Glu  Pro  Ile  Tyr  Leu  Gly  Gly  Val  Phe  Gln  Leu  Glu  Lys
          115                      120                      125

Gly  Asp  Arg  Leu  Ser  Ala  Glu  Ile  Asn  Arg  Pro  Asp  Tyr  Leu  Asp  Phe
     130                      135                      140
```

```
                Ala Glu Ser Gly Gln Val Tyr Phe Gly Ile Ile Ala Leu
                145                 150                 155
```

(2) INFORMATION FOR SEQ ID NO:2:

(i) SEQUENCE CHARACTERISTICS:
        (A) LENGTH: 3977 base pairs
        (B) TYPE: nucleic acid
        (C) STRANDEDNESS: single
        (D) TOPOLOGY: linear (ii) MOLECULE TYPE: DNA (recombinant plasmid)

(vii) IMMEDIATE SOURCE:
        (B) CLONE: pDS56/RBSII,Sph1-TNF-alpha (ix) FEATURE:
        (A) NAME/KEY: CDS
        (B) LOCATION: 115..591

(xi) SEQUENCE DESCRIPTION: SEQ ID NO:2:

```
CTCGAGAAAT CATAAAAAAT TTATTTGCTT TGTGAGCGGA TAACAATTAT AATAGATTCA      60

ATTGTGAGCG GATAACAATT TCACACAGGA TTCATTAAAG AGGAGAAATT AAGC ATG       117
                                                              Met
                                                               1

GTC AGA TCA TCT TCT CGA ACC CCG AGT GAC AAG CCT GTA GCC CAT GTT      165
Val Arg Ser Ser Ser Arg Thr Pro Ser Asp Lys Pro Val Ala His Val
          5                  10                  15

GTC GCG AAC CCT CAA GCT GAG GGG CAG CTC CAG TGG CTG AAC CGC CGG      213
Val Ala Asn Pro Gln Ala Glu Gly Gln Leu Gln Trp Leu Asn Arg Arg
             20                  25                  30

GCC AAT GCC CTC CTG GCC AAT GGC GTG GAG CTG AGA GAT AAC CAG CTG      261
Ala Asn Ala Leu Leu Ala Asn Gly Val Glu Leu Arg Asp Asn Gln Leu
 35                  40                  45

GTG GTG CCA TCA GAG GGC CTG TAC CTC ATC TAC TCC CAG GTC CTC TTC      309
Val Val Pro Ser Glu Gly Leu Tyr Leu Ile Tyr Ser Gln Val Leu Phe
 50                  55                  60                  65

AAG GGC CAA GGC TGC CCC TCC ACC CAT GTG CTC CTC ACC CAC ACC ATC      357
Lys Gly Gln Gly Cys Pro Ser Thr His Val Leu Leu Thr His Thr Ile
                 70                  75                  80

AGC CGC ATC GCC GTC TCC TAC CAG ACC AAG GTC AAC CTC CTC TCT GCC      405
Ser Arg Ile Ala Val Ser Tyr Gln Thr Lys Val Asn Leu Leu Ser Ala
             85                  90                  95

ATC AAG AGC CCC TGC CAG AGG GAG ACC CCA GAG GGG GCT GAG GCC AAG      453
Ile Lys Ser Pro Cys Gln Arg Glu Thr Pro Glu Gly Ala Glu Ala Lys
        100                 105                 110

CCC TGG TAT GAG CCC ATC TAT CTG GGA GGG GTC TTC CAG CTG GAG AAG      501
Pro Trp Tyr Glu Pro Ile Tyr Leu Gly Gly Val Phe Gln Leu Glu Lys
    115                 120                 125

GGT GAC CGA CTC AGC GCT GAG ATC AAT CGG CCC GAC TAT CTC GAC TTT      549
Gly Asp Arg Leu Ser Ala Glu Ile Asn Arg Pro Asp Tyr Leu Asp Phe
130                 135                 140                 145

GCC GAG TCT GGG CAG GTC TAC TTT GGG ATC ATT GCC CTG TGAGGAGGAC       598
Ala Glu Ser Gly Gln Val Tyr Phe Gly Ile Ile Ala Leu
                150                 155

GAACATCCAA CCTTCCCAAA CGCCTCCCCT GCCCCAATCC CTTTATTACC CCTCCTTCA     658

GACACCCTCA ACCTCTTCTG GCTCAAAAAG AGAATTGGGG GCTTAGGGTC GGAACCCAAG    718

CTTGGACTCC TGTTGATAGA TCCAGTAATG ACCTCAGAAC TCCATCTGGA TTTGTTCAGA    778

ACGCTCGGTT GCCGCCGGGG GTTTTTATT GGTGAGAATC CAAGCTAGCT TGGCGAGATT     838
```

| | | | | | |
|---|---|---|---|---|---|
| TTCAGGAGCT | AAGGAAGCTA | AAATGGAGAA | AAAAATCACT | GGATATACCA | CCGTTGATAT | 898
| ATCCCAATGG | CATCGTAAAG | AACATTTTGA | GGCATTTCAG | TCAGTTGCTC | AATGTACCTA | 958
| TAACCAGACC | GTTACGCTGG | ATATTACGGC | CTTTTAAAG | ACCGTAAAGA | AAAATAAGCA | 1018
| CAAGTTTTAT | CCGGCCTTTA | TTCACATTCT | TGCCCGCCTG | ATGAATGCTC | ATCCGGAATT | 1078
| TCGTATGGCA | ATGAAAGACG | GTGAGCTGGT | GATATGGGAT | AGTGTTCACC | CTTGTTACAC | 1138
| CGTTTTCCAT | GAGCAAACTG | AAACGTTTTC | ATCGCTCTGG | AGTGAATACC | ACGACGATTT | 1198
| CCGGCAGTTT | CTACACATAT | ATTCGCAAGA | TGTGGCGTGT | TACGGTGAAA | ACCTGGCCTA | 1258
| TTTCCCTAAA | GGGTTTATTG | AGAATATGTT | TTCGTCTCA | GCCAATCCCT | GGGTGAGTTT | 1318
| CACCAGTTTT | GATTTAAACG | TGGCCAATAT | GGACAACTTC | TTCGCCCCCG | TTTTCACCAT | 1378
| GGGCAAATAT | TATACGCAAG | GCGACAAGGT | GCTGATGCCG | CTGGCGATTC | AGGTTCATCA | 1438
| TGCCGTCTGT | GATGGCTTCC | ATGTCGGCAG | AATGCTTAAT | GAATTACAAC | AGTACTGCGA | 1498
| TGAGTGGCAG | GGCGGGGCGT | AATTTTTTA | AGGCAGTTAT | TGGTGCCCTT | AAACGCCTGG | 1558
| GGTAATGACT | CTCTAGCTTG | AGGCATCAAA | TAAAACGAAA | GGCTCAGTCG | AAAGACTGGG | 1618
| CCTTTCGTTT | TATCTGTTGT | TTGTCGGTGA | ACGCTCTCCT | GAGTAGGACA | AATCCGCCGC | 1678
| TCTAGAGCTG | CCTCGCGCGT | TTCGGTGATG | ACGGTGAAAA | CCTCTGACAC | ATGCAGCTCC | 1738
| CGGAGACGGT | CACAGCTTGT | CTGTAAGCGG | ATGCCGGGAG | CAGACAAGCC | CGTCAGGGCG | 1798
| CGTCAGCGGG | TGTTGGCGGG | TGTCGGGGCG | CAGCCATGAC | CCAGTCACGT | AGCGATAGCG | 1858
| GAGTGTATAC | TGGCTTAACT | ATGCCGCATC | AGAGCAGATT | GTACTGAGAG | TGCACCATAT | 1918
| GCGGTGTGAA | ATACCGCACA | GATGCGTAAG | GAGAAAATAC | CGCATCAGGC | GCTCTTCCGC | 1978
| TTCCTCGCTC | ACTGACTCGC | TGCGCTCGGT | CTGTCGGCTG | CGGCGAGCGG | TATCAGCTCA | 2038
| CTCAAAGGCG | GTAATACGGT | TATCCACAGA | ATCAGGGGAT | AACGCAGGAA | AGAACATGTG | 2098
| AGCAAAAGGC | CAGCAAAAGG | CCAGGAACCG | TAAAAAGGCC | GCGTTGCTGG | CGTTTTCCA | 2158
| TAGGCTCCGC | CCCCCTGACG | AGCATCACAA | AAATCGACGC | TCAAGTCAGA | GGTGGCGAAA | 2218
| CCCGACAGGA | CTATAAAGAT | ACCAGGCGTT | TCCCCCTGGA | AGCTCCCTCG | TGCGCTCTCC | 2278
| TGTTCCGACC | CTGCCGCTTA | CCGGATACCT | GTCCGCCTTT | CTCCCTTCGG | GAAGCGTGGC | 2338
| GCTTTCTCAA | TGCTCACGCT | GTAGGTATCT | CAGTTGCCTG | TAGGTCGTTC | GCTCCAAGCT | 2398
| GGGCTGTGTG | CACGAACCCC | CCGTTCAGCC | CGACCGCTGC | GCCTTATCCG | GTAACTATCG | 2458
| TCTTGAGTCC | AACCCGGTAA | GACACGACTT | ATCGCCACTG | GCAGCAGCCA | CTGGTAACAG | 2518
| GATTAGCAGA | GCGAGGTATG | TAGGGGGTGC | TACAGAGTTC | TTGAAGTGGT | GGCCTAACTA | 2578
| CGGCTACACT | AGAAGGACAG | TATTTGGTAT | CTGCGCTCTG | CTGAAGCCAG | TTACCTTCGG | 2638
| AAAAAGAGTT | GGTAGCTCTT | GATCCGGCAA | ACAAACCACC | GCTGGTAGCG | GTGGTTTTTT | 2698
| TGTTTGCAAG | CAGCAGATTA | CGCGCAGAAA | AAAAGGATCT | CAAGAAGATC | CTTTGATCTT | 2758
| TTCTACGGGG | TCTGACGCTC | AGTGGAACGA | AAACTCACGT | TAAGGGATTT | TGGTCATGAG | 2818
| ATTATCAAAA | AGGATCTTCA | CCTAGATCCT | TTTAAATTAA | AAATGAAGTT | TTAAATCAAT | 2878
| CTAAAGTATA | TATGAGTAAA | CTTGGTCTGA | CAGTTACCAA | TGCTTAATCA | GTGAGGCACC | 2938
| TATCTCAGCG | ATCTGTCTAT | TTCGTTCATC | CATAGCTGCC | TGACTCCCCG | TCGTGTAGAT | 2998
| AACTACGATA | CGGGAGGGCT | TACCATCTGG | CCCCAGTGCT | GCAATGATAC | CGCGAGACCC | 3058
| ACGCTCACCG | GCTCCAGATT | TATCAGCAAT | AAACCAGCCA | GCCGGAAGGG | CCGAGCGCAG | 3118
| AAGTGGTCCT | GCAACTTTAT | CCGCCTCCAT | CCAGTCTATT | AATTGTTGCC | GGGAAGCTAG | 3178
| AGTAAGTAGT | CCGCCAGTTA | ATAGTTTGCG | CAACGTTGTT | GCCATTGCTA | CAGGCATCGT | 3238

```
GGTCTCACGC  TCGTCGTTTG  GTATGGCTTC  ATTCAGCTCC  GGTTCCCAAC  GATCAAGGCG   3298

AGTTACATGA  TCCCCCATGT  TGTGCAAAAA  AGCGGTTAGC  TCCTTCGGTC  CTCCGATCGT   3358

TGTCAGAAGT  AAGTTGGCCG  CAGTGTTATC  ACTCATGGTT  ATGGCAGCAC  TGCATAATTC   3418

TCTTACTGTC  ATGCCATCCG  TAAGATGCTT  TTCTGTGACT  GGTGAGTACT  CAACCAAGTC   3478

ATTCTGAGAA  TAGTGTATGC  GGCGACCGAG  TTGCTCTTGC  CCGGCGTCAA  TACGGGATAA   3538

TACCGCGCCA  CATAGCAGAA  CTTTAAAAGT  GCTCATCATT  GGAAAACGTT  CTTCGGGGCG   3598

AAAACTCTCA  AGGATCTTAC  CGCTGTTGAG  ATCCAGTTCG  ATGTAACCCA  CTCGTGCACC   3658

CAACTGATCT  TCAGCATCTT  TTACTTTCAC  CAGCGTTTCT  GGCTGAGCAA  AAACAGGAAG   3718

GCAAATGCC   GCAAAAAGG   GAATAAGGGC  GACACGGAAA  TGTTGAATAC  TCATACTCTT   3778

CCTTTTTCAA  TATTATTGAA  GCATTATCA   GGGTTATTGT  CTCATGAGCG  GATACATATT   3838

TGAATGTATT  TAGAAAAATA  AACAAATAGG  GGTTCCGCGC  ACATTCCCC   GAAAAGTCCC   3898

ACCTGACGTC  TAAGAAACCA  TTATTATCAT  GACATTAACC  TATAAAAATA  GGCGTATCAC   3958

GAGGCCCTTT  CGTCTTCAC                                                    3977
```

( 2 ) INFORMATION FOR SEQ ID NO:3:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( i x ) FEATURE:
        ( A ) NAME/KEY: Modified site
        ( B ) LOCATION: 29, 31 and 32
        ( D ) OTHER INFORMATION:/note="Xaa =any naturally occurring amino acid"

( x i ) SEQUENCE DESCRIPTION: SEQ ID NO:3:

```
Met  Val  Arg  Ser  Ser  Ser  Arg  Thr  Pro  Ser  Asp  Lys  Pro  Val  Ala  His
 -1   +1             5                       10                        15
Val  Val  Ala  Asn  Pro  Gln  Ala  Glu  Gly  Gln  Leu  Gln  Trp  Xaa  Asn  Xaa
               20                       25                        30

Xaa  Ala  Asn  Ala  Leu  Leu  Ala  Asn  Gly  Val  Glu  Leu  Arg  Asp  Asn  Gln
               35                       40                        45

Leu  Val  Val  Pro  Ser  Glu  Gly  Leu  Tyr  Leu  Ile  Tyr  Ser  Gln  Val  Leu
          50                       55                        60

Phe  Lys  Gly  Gln  Gly  Cys  Pro  Ser  Thr  His  Val  Leu  Leu  Thr  His  Thr
     65                       70                        75

Ile  Ser  Arg  Ile  Ala  Val  Ser  Tyr  Gln  Thr  Lys  Val  Asn  Leu  Leu  Ser
 80                       85                        90                        95

Ala  Ile  Lys  Ser  Pro  Cys  Gln  Arg  Glu  Thr  Pro  Glu  Gly  Ala  Glu  Ala
               100                      105                      110

Lys  Pro  Trp  Tyr  Glu  Pro  Ile  Tyr  Leu  Gly  Gly  Val  Phe  Gln  Leu  Glu
               115                      120                      125

Lys  Gly  Asp  Arg  Leu  Ser  Ala  Glu  Ile  Asn  Arg  Pro  Asp  Tyr  Leu  Asp
               130                      135                      140

Phe  Ala  Glu  Ser  Gly  Gln  Val  Tyr  Phe  Gly  Ile  Ile  Ala  Leu
     145                      150                      155
```

( 2 ) INFORMATION FOR SEQ ID NO:4:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Val | Arg | Ser | Ser | Ser | Arg | Thr | Pro | Ser | Asp | Lys | Pro | Val | Ala | His |
|---|---|---|---|---|---|---|---|---|---|---|---|---|---|---|---|
| -1 | +1 | | | | 5 | | | | | 10 | | | | | 15 |
| Val | Val | Ala | Asn | Pro | Gln | Ala | Glu | Gly | Gln | Leu | Gln | Trp | Ser | Asn | Arg |
| | | | | 20 | | | | | 25 | | | | | 30 | |
| Arg | Ala | Asn | Ala | Leu | Leu | Ala | Asn | Gly | Val | Glu | Leu | Arg | Asp | Asn | Gln |
| | | | 35 | | | | | 40 | | | | | 45 | | |
| Leu | Val | Val | Pro | Ser | Glu | Gly | Leu | Tyr | Leu | Ile | Tyr | Ser | Gln | Val | Leu |
| | | | 50 | | | | 55 | | | | | 60 | | | |
| Phe | Lys | Gly | Gln | Gly | Cys | Pro | Ser | Thr | His | Val | Leu | Leu | Thr | His | Thr |
| | 65 | | | | | 70 | | | | | 75 | | | | |
| Ile | Ser | Arg | Ile | Ala | Val | Ser | Tyr | Gln | Thr | Lys | Val | Asn | Leu | Leu | Ser |
| 80 | | | | | 85 | | | | | 90 | | | | | 95 |
| Ala | Ile | Lys | Ser | Pro | Cys | Gln | Arg | Glu | Thr | Pro | Glu | Gly | Ala | Glu | Ala |
| | | | | 100 | | | | | 105 | | | | | 110 | |
| Lys | Pro | Trp | Tyr | Glu | Pro | Ile | Tyr | Leu | Gly | Gly | Val | Phe | Gln | Leu | Glu |
| | | | | 115 | | | | | 120 | | | | | 125 | |
| Lys | Gly | Asp | Arg | Leu | Ser | Ala | Glu | Ile | Asn | Arg | Pro | Asp | Tyr | Leu | Asp |
| | | | 130 | | | | | 135 | | | | | 140 | | |
| Phe | Ala | Glu | Ser | Gly | Gln | Val | Tyr | Phe | Gly | Ile | Ile | Ala | Leu | | |
| | 145 | | | | | 150 | | | | | 155 | | | | |

( 2 ) INFORMATION FOR SEQ ID NO:5:

( i ) SEQUENCE CHARACTERISTICS:
  ( A ) LENGTH: 158 amino acids
  ( B ) TYPE: amino acid
  ( D ) TOPOLOGY: linear ( i i ) MOLECULE TYPE: protein ( x i ) SEQUENCE DESCRIPTION: SEQ ID NO:5:

| Met | Val | Arg | Ser | Ser | Ser | Arg | Thr | Pro | Ser | Asp | Lys | Pro | Val | Ala | His |
|---|---|---|---|---|---|---|---|---|---|---|---|---|---|---|---|
| -1 | +1 | | | | 5 | | | | | 10 | | | | | 15 |
| Val | Val | Ala | Asn | Pro | Gln | Ala | Glu | Gly | Gln | Leu | Gln | Trp | Gly | Asn | Arg |
| | | | | 20 | | | | | 25 | | | | | 30 | |
| Arg | Ala | Asn | Ala | Leu | Leu | Ala | Asn | Gly | Val | Glu | Leu | Arg | Asp | Asn | Gln |
| | | | 35 | | | | | 40 | | | | | 45 | | |
| Leu | Val | Val | Pro | Ser | Glu | Gly | Leu | Tyr | Leu | Ile | Tyr | Ser | Gln | Val | Leu |
| | | | 50 | | | | 55 | | | | | 60 | | | |
| Phe | Lys | Gly | Gln | Gly | Cys | Pro | Ser | Thr | His | Val | Leu | Leu | Thr | His | Thr |
| | 65 | | | | | 70 | | | | | 75 | | | | |
| Ile | Ser | Arg | Ile | Ala | Val | Ser | Tyr | Gln | Thr | Lys | Val | Asn | Leu | Leu | Ser |
| 80 | | | | | 85 | | | | | 90 | | | | | 95 |
| Ala | Ile | Lys | Ser | Pro | Cys | Gln | Arg | Glu | Thr | Pro | Glu | Gly | Ala | Glu | Ala |
| | | | | 100 | | | | | 105 | | | | | 110 | |
| Lys | Pro | Trp | Tyr | Glu | Pro | Ile | Tyr | Leu | Gly | Gly | Val | Phe | Gln | Leu | Glu |
| | | | | 115 | | | | | 120 | | | | | 125 | |
| Lys | Gly | Asp | Arg | Leu | Ser | Ala | Glu | Ile | Asn | Arg | Pro | Asp | Tyr | Leu | Asp |
| | | | 130 | | | | | 135 | | | | | 140 | | |
| Phe | Ala | Glu | Ser | Gly | Gln | Val | Tyr | Phe | Gly | Ile | Ile | Ala | Leu | | |
| | 145 | | | | | 150 | | | | | 155 | | | | |

( 2 ) INFORMATION FOR SEQ ID NO:6:

( i ) SEQUENCE CHARACTERISTICS:
  ( A ) LENGTH: 158 amino acids (B) TYPE: amino acid
(D) TOPOLOGY: linear (ii) MOLECULE TYPE: protein (xi) SEQUENCE DESCRIPTION: SEQ ID NO:6:

```
Met  Val  Arg  Ser  Ser  Ser  Arg  Thr  Pro  Ser  Asp  Lys  Pro  Val  Ala  His
 -1   +1                  5                      10                       15
Val  Val  Ala  Asn  Pro  Gln  Ala  Glu  Gly  Gln  Leu  Gln  Trp  Tyr  Asn  Arg
                    20                      25                      30
Arg  Ala  Asn  Ala  Leu  Leu  Ala  Asn  Gly  Val  Glu  Leu  Arg  Asp  Asn  Gln
                35                      40                      45
Leu  Val  Val  Pro  Ser  Glu  Gly  Leu  Tyr  Leu  Ile  Tyr  Ser  Gln  Val  Leu
           50                      55                      60
Phe  Lys  Gly  Gln  Gly  Cys  Pro  Ser  Thr  His  Val  Leu  Leu  Thr  His  Thr
     65                      70                      75
Ile  Ser  Arg  Ile  Ala  Val  Ser  Tyr  Gln  Thr  Lys  Val  Asn  Leu  Leu  Ser
 80                      85                      90                       95
Ala  Ile  Lys  Ser  Pro  Cys  Gln  Arg  Glu  Thr  Pro  Glu  Gly  Ala  Glu  Ala
                100                     105                     110
Lys  Pro  Trp  Tyr  Glu  Pro  Ile  Tyr  Leu  Gly  Gly  Val  Phe  Gln  Leu  Glu
                115                     120                     125
Lys  Gly  Asp  Arg  Leu  Ser  Ala  Glu  Ile  Asn  Arg  Pro  Asp  Tyr  Leu  Asp
           130                     135                     140
Phe  Ala  Glu  Ser  Gly  Gln  Val  Tyr  Phe  Gly  Ile  Ile  Ala  Leu
     145                     150                     155
```

(2) INFORMATION FOR SEQ ID NO:7:

(i) SEQUENCE CHARACTERISTICS:
(A) LENGTH: 158 amino acids
(B) TYPE: amino acid
(D) TOPOLOGY: linear (ii) MOLECULE TYPE: protein (xi) SEQUENCE DESCRIPTION: SEQ ID NO:7:

```
Met  Val  Arg  Ser  Ser  Ser  Arg  Thr  Pro  Ser  Asp  Lys  Pro  Val  Ala  His
 -1   +1                  5                      10                       15
Val  Val  Ala  Asn  Pro  Gln  Ala  Glu  Gly  Gln  Leu  Gln  Trp  Leu  Asn  Glu
                    20                      25                      30
Arg  Ala  Asn  Ala  Leu  Leu  Ala  Asn  Gly  Val  Glu  Leu  Arg  Asp  Asn  Gln
                35                      40                      45
Leu  Val  Val  Pro  Ser  Glu  Gly  Leu  Tyr  Leu  Ile  Tyr  Ser  Gln  Val  Leu
           50                      55                      60
Phe  Lys  Gly  Gln  Gly  Cys  Pro  Ser  Thr  His  Val  Leu  Leu  Thr  His  Thr
     65                      70                      75
Ile  Ser  Arg  Ile  Ala  Val  Ser  Tyr  Gln  Thr  Lys  Val  Asn  Leu  Leu  Ser
 80                      85                      90                       95
Ala  Ile  Lys  Ser  Pro  Cys  Gln  Arg  Glu  Thr  Pro  Glu  Gly  Ala  Glu  Ala
                100                     105                     110
Lys  Pro  Trp  Tyr  Glu  Pro  Ile  Tyr  Leu  Gly  Gly  Val  Phe  Gln  Leu  Glu
                115                     120                     125
Lys  Gly  Asp  Arg  Leu  Ser  Ala  Glu  Ile  Asn  Arg  Pro  Asp  Tyr  Leu  Asp
           130                     135                     140
Phe  Ala  Glu  Ser  Gly  Gln  Val  Tyr  Phe  Gly  Ile  Ile  Ala  Leu
     145                     150                     155
```

(2) INFORMATION FOR SEQ ID NO:8:

( i ) SEQUENCE CHARACTERISTICS:
   ( A ) LENGTH: 158 amino acids
   ( B ) TYPE: amino acid
   ( D ) TOPOLOGY: linear ( i i ) MOLECULE TYPE: protein ( x i ) SEQUENCE DESCRIPTION: SEQ ID NO:8:

```
Met  Val  Arg  Ser  Ser  Ser  Arg  Thr  Pro  Ser  Asp  Lys  Pro  Val  Ala  His
 -1   +1                  5                      10                       15
Val  Val  Ala  Asn  Pro  Gln  Ala  Glu  Gly  Gln  Leu  Gln  Trp  Leu  Asn  Asn
                    20                      25                      30

Arg  Ala  Asn  Ala  Leu  Leu  Ala  Asn  Gly  Val  Glu  Leu  Arg  Asp  Asn  Gln
               35                      40                      45

Leu  Val  Val  Pro  Ser  Glu  Gly  Leu  Tyr  Leu  Ile  Tyr  Ser  Gln  Val  Leu
          50                      55                      60

Phe  Lys  Gly  Gln  Gly  Cys  Pro  Ser  Thr  His  Val  Leu  Leu  Thr  His  Thr
     65                      70                      75

Ile  Ser  Arg  Ile  Ala  Val  Ser  Tyr  Gln  Thr  Lys  Val  Asn  Leu  Leu  Ser
 80                      85                      90                       95

Ala  Ile  Lys  Ser  Pro  Cys  Gln  Arg  Glu  Thr  Pro  Glu  Gly  Ala  Glu  Ala
               100                     105                     110

Lys  Pro  Trp  Tyr  Glu  Pro  Ile  Tyr  Leu  Gly  Gly  Val  Phe  Gln  Leu  Glu
               115                     120                     125

Lys  Gly  Asp  Arg  Leu  Ser  Ala  Glu  Ile  Asn  Arg  Pro  Asp  Tyr  Leu  Asp
               130                     135                     140

Phe  Ala  Glu  Ser  Gly  Gln  Val  Tyr  Phe  Gly  Ile  Ile  Ala  Leu
     145                     150                     155
```

( 2 ) INFORMATION FOR SEQ ID NO:9:

( i ) SEQUENCE CHARACTERISTICS:
      ( A ) LENGTH: 158 amino acids
      ( B ) TYPE: amino acid
      ( D ) TOPOLOGY: linear ( i i ) MOLECULE TYPE: protein ( x i ) SEQUENCE DESCRIPTION: SEQ ID NO:9:

```
Met  Val  Arg  Ser  Ser  Ser  Arg  Thr  Pro  Ser  Asp  Lys  Pro  Val  Ala  His
 -1   +1                  5                      10                       15
Val  Val  Ala  Asn  Pro  Gln  Ala  Glu  Gly  Gln  Leu  Gln  Trp  Leu  Asn  Arg
                    20                      25                      30

Trp  Ala  Asn  Ala  Leu  Leu  Ala  Asn  Gly  Val  Glu  Leu  Arg  Asp  Asn  Gln
               35                      40                      45

Leu  Val  Val  Pro  Ser  Glu  Gly  Leu  Tyr  Leu  Ile  Tyr  Ser  Gln  Val  Leu
          50                      55                      60

Phe  Lys  Gly  Gln  Gly  Cys  Pro  Ser  Thr  His  Val  Leu  Leu  Thr  His  Thr
     65                      70                      75

Ile  Ser  Arg  Ile  Ala  Val  Ser  Tyr  Gln  Thr  Lys  Val  Asn  Leu  Leu  Ser
 80                      85                      90                       95

Ala  Ile  Lys  Ser  Pro  Cys  Gln  Arg  Glu  Thr  Pro  Glu  Gly  Ala  Glu  Ala
               100                     105                     110

Lys  Pro  Trp  Tyr  Glu  Pro  Ile  Tyr  Leu  Gly  Gly  Val  Phe  Gln  Leu  Glu
               115                     120                     125

Lys  Gly  Asp  Arg  Leu  Ser  Ala  Glu  Ile  Asn  Arg  Pro  Asp  Tyr  Leu  Asp
               130                     135                     140

Phe  Ala  Glu  Ser  Gly  Gln  Val  Tyr  Phe  Gly  Ile  Ile  Ala  Leu
     145                     150                     155
```

(2) INFORMATION FOR SEQ ID NO:10:

(i) SEQUENCE CHARACTERISTICS:
(A) LENGTH: 158 amino acids
(B) TYPE: amino acid
(D) TOPOLOGY: linear (ii) MOLECULE TYPE: protein (xi) SEQUENCE DESCRIPTION: SEQ ID NO:10:

| Met | Val | Arg | Ser | Ser | Ser | Arg | Thr | Pro | Ser | Asp | Lys | Pro | Val | Ala | His |
|---|---|---|---|---|---|---|---|---|---|---|---|---|---|---|---|
| -1 | +1 | | | 5 | | | | | 10 | | | | | | 15 |
| Val | Val | Ala | Asn | Pro | Gln | Ala | Glu | Gly | Gln | Leu | Gln | Trp | Leu | Asn | Arg |
| | | | | 20 | | | | | 25 | | | | | 30 | |
| Tyr | Ala | Asn | Ala | Leu | Leu | Ala | Asn | Gly | Val | Glu | Leu | Arg | Asp | Asn | Gln |
| | | | 35 | | | | | 40 | | | | | 45 | | |
| Leu | Val | Val | Pro | Ser | Glu | Gly | Leu | Tyr | Leu | Ile | Tyr | Ser | Gln | Val | Leu |
| | | | 50 | | | | 55 | | | | | 60 | | | |
| Phe | Lys | Gly | Gln | Gly | Cys | Pro | Ser | Thr | His | Val | Leu | Leu | Thr | His | Thr |
| | 65 | | | | | 70 | | | | | 75 | | | | |
| Ile | Ser | Arg | Ile | Ala | Val | Ser | Tyr | Gln | Thr | Lys | Val | Asn | Leu | Leu | Ser |
| 80 | | | | | 85 | | | | | 90 | | | | | 95 |
| Ala | Ile | Lys | Ser | Pro | Cys | Gln | Arg | Glu | Thr | Pro | Glu | Gly | Ala | Glu | Ala |
| | | | | 100 | | | | | 105 | | | | | 110 | |
| Lys | Pro | Trp | Tyr | Glu | Pro | Ile | Tyr | Leu | Gly | Gly | Val | Phe | Gln | Leu | Glu |
| | | | 115 | | | | | 120 | | | | | 125 | | |
| Lys | Gly | Asp | Arg | Leu | Ser | Ala | Glu | Ile | Asn | Arg | Pro | Asp | Tyr | Leu | Asp |
| | | 130 | | | | | 135 | | | | | 140 | | | |
| Phe | Ala | Glu | Ser | Gly | Gln | Val | Tyr | Phe | Gly | Ile | Ile | Ala | Leu | | |
| | 145 | | | | | 150 | | | | | 155 | | | | |

(2) INFORMATION FOR SEQ ID NO:11:

(i) SEQUENCE CHARACTERISTICS:
(A) LENGTH: 158 amino acids
(B) TYPE: amino acid
(D) TOPOLOGY: linear (ii) MOLECULE TYPE: protein (xi) SEQUENCE DESCRIPTION: SEQ ID NO:11:

| Met | Val | Arg | Ser | Ser | Ser | Arg | Thr | Pro | Ser | Asp | Lys | Pro | Val | Ala | His |
|---|---|---|---|---|---|---|---|---|---|---|---|---|---|---|---|
| -1 | +1 | | | 5 | | | | | 10 | | | | | | 15 |
| Val | Val | Ala | Asn | Pro | Gln | Ala | Glu | Gly | Gln | Leu | Gln | Trp | Leu | Asn | Asn |
| | | | | 20 | | | | | 25 | | | | | 30 | |
| Thr | Ala | Asn | Ala | Leu | Leu | Ala | Asn | Gly | Val | Glu | Leu | Arg | Asp | Asn | Gln |
| | | | 35 | | | | | 40 | | | | | 45 | | |
| Leu | Val | Val | Pro | Ser | Glu | Gly | Leu | Tyr | Leu | Ile | Tyr | Ser | Gln | Val | Leu |
| | | | 50 | | | | 55 | | | | | 60 | | | |
| Phe | Lys | Gly | Gln | Gly | Cys | Pro | Ser | Thr | His | Val | Leu | Leu | Thr | His | Thr |
| | 65 | | | | | 70 | | | | | 75 | | | | |
| Ile | Ser | Arg | Ile | Ala | Val | Ser | Tyr | Gln | Thr | Lys | Val | Asn | Leu | Leu | Ser |
| 80 | | | | | 85 | | | | | 90 | | | | | 95 |
| Ala | Ile | Lys | Ser | Pro | Cys | Gln | Arg | Glu | Thr | Pro | Glu | Gly | Ala | Glu | Ala |
| | | | | 100 | | | | | 105 | | | | | 110 | |
| Lys | Pro | Trp | Tyr | Glu | Pro | Ile | Tyr | Leu | Gly | Gly | Val | Phe | Gln | Leu | Glu |
| | | | 115 | | | | | 120 | | | | | 125 | | |
| Lys | Gly | Asp | Arg | Leu | Ser | Ala | Glu | Ile | Asn | Arg | Pro | Asp | Tyr | Leu | Asp |
| | | 130 | | | | | 135 | | | | | 140 | | | |
| Phe | Ala | Glu | Ser | Gly | Gln | Val | Tyr | Phe | Gly | Ile | Ile | Ala | Leu | | |
| | 145 | | | | | 150 | | | | | 155 | | | | |

( 2 ) INFORMATION FOR SEQ ID NO:12:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met  Val  Arg  Ser  Ser  Ser  Arg  Thr  Pro  Ser  Asp  Lys  Pro  Val  Ala  His
 -1   +1                  5                      10                      15
Val  Val  Ala  Asn  Pro  Gln  Ala  Glu  Gly  Gln  Leu  Gln  Trp  Ser  Asn  Arg
                  20                      25                      30
Trp  Ala  Asn  Ala  Leu  Leu  Ala  Asn  Gly  Val  Glu  Leu  Arg  Asp  Asn  Gln
                  35                      40                      45
Leu  Val  Val  Pro  Ser  Glu  Gly  Leu  Tyr  Leu  Ile  Tyr  Ser  Gln  Val  Leu
             50                      55                      60
Phe  Lys  Gly  Gln  Gly  Cys  Pro  Ser  Thr  His  Val  Leu  Leu  Thr  His  Thr
       65                      70                      75
Ile  Ser  Arg  Ile  Ala  Val  Ser  Tyr  Gln  Thr  Lys  Val  Asn  Leu  Leu  Ser
 80                      85                      90                      95
Ala  Ile  Lys  Ser  Pro  Cys  Gln  Arg  Glu  Thr  Pro  Glu  Gly  Ala  Glu  Ala
                 100                     105                     110
Lys  Pro  Trp  Tyr  Glu  Pro  Ile  Tyr  Leu  Gly  Gly  Val  Phe  Gln  Leu  Glu
                 115                     120                     125
Lys  Gly  Asp  Arg  Leu  Ser  Ala  Glu  Ile  Asn  Arg  Pro  Asp  Tyr  Leu  Asp
            130                     135                     140
Phe  Ala  Glu  Ser  Gly  Gln  Val  Tyr  Phe  Gly  Ile  Ile  Ala  Leu
       145                     150                     155
```

( 2 ) INFORMATION FOR SEQ ID NO:13:

( i ) SEQUENCE CHARACTERISTICS:
        ( A ) LENGTH: 3977 base pairs
        ( B ) TYPE: nucleic acid
        ( C ) STRANDEDNESS: single
        ( D ) TOPOLOGY: linear ( i i ) MOLECULE TYPE: DNA (recombinant plasmid)

( v i i ) IMMEDIATE SOURCE:
        ( B ) CLONE: pDS56/RBSII,Sph1-TNF- alpha ( i x ) FEATURE:
        ( A ) NAME/KEY: CDS
        ( B ) LOCATION: 115..591

( i x ) FEATURE:
        ( A ) NAME/KEY: Modified site
        ( B ) LOCATION: 202-204, 208-210 and 211-213
        ( D ) OTHER INFORMATION:/note="N =A, G, C or T"

( x i ) SEQUENCE DESCRIPTION: SEQ ID NO:13:

```
CTCGAGAAAT CATAAAAAAT TTATTTGCTT TGTGAGCGGA TAACAATTAT AATAGATTCA        60

ATTGTGAGCG GATAACAATT TCACACAGGA TTCATTAAAG AGGAGAAATT AAGC ATG         117
                                                              Met
                                                               -1

GTC  AGA  TCA  TCT  TCT  CGA  ACC  CCG  AGT  GAC  AAG  CCT  GTA  GCC  CAT  GTT  165
Val  Arg  Ser  Ser  Ser  Arg  Thr  Pro  Ser  Asp  Lys  Pro  Val  Ala  His  Val
 +1                  5                      10                      15
GTC  GCG  AAC  CCT  CAA  GCT  GAG  GGG  CAG  CTC  CAG  TGG  NNN  AAC  NNN  NNN  213
Val  Ala  Asn  Pro  Gln  Ala  Glu  Gly  Gln  Leu  Gln  Trp  Xaa  Asn  Xaa  Xaa
```

|  |  |  |  |  |  |  |  |  |  |  |  |  |  |  |  |
|---|---|---|---|---|---|---|---|---|---|---|---|---|---|---|---|
|  |  | 20 |  |  |  |  | 25 |  |  |  |  |  | 30 |  |  |
| GCC | AAT | GCC | CTC | CTG | GCC | AAT | GGC | GTG | GAG | CTG | AGA | GAT | AAC | CAG | CTG | 261 |
| Ala | Asn | Ala | Leu | Leu | Ala | Asn | Gly | Val | Glu | Leu | Arg | Asp | Asn | Gln | Leu |
|  |  | 35 |  |  |  |  | 40 |  |  |  |  | 45 |  |  |  |
| GTG | GTG | CCA | TCA | GAG | GGC | CTG | TAC | CTC | ATC | TAC | TCC | CAG | GTC | CTC | TTC | 309 |
| Val | Val | Pro | Ser | Glu | Gly | Leu | Tyr | Leu | Ile | Tyr | Ser | Gln | Val | Leu | Phe |
|  | 50 |  |  |  |  | 55 |  |  |  |  | 60 |  |  |  |  |
| AAG | GGC | CAA | GGC | TGC | CCC | TCC | ACC | CAT | GTG | CTC | CTC | ACC | CAC | ACC | ATC | 357 |
| Lys | Gly | Gln | Gly | Cys | Pro | Ser | Thr | His | Val | Leu | Leu | Thr | His | Thr | Ile |
| 65 |  |  |  |  | 70 |  |  |  |  | 75 |  |  |  |  | 80 |
| AGC | CGC | ATC | GCC | GTC | TCC | TAC | CAG | ACC | AAG | GTC | AAC | CTC | CTC | TCT | GCC | 405 |
| Ser | Arg | Ile | Ala | Val | Ser | Tyr | Gln | Thr | Lys | Val | Asn | Leu | Leu | Ser | Ala |
|  |  |  |  | 85 |  |  |  |  | 90 |  |  |  |  | 95 |  |
| ATC | AAG | AGC | CCC | TGC | CAG | AGG | GAG | ACC | CCA | GAG | GGG | GCT | GAG | GCC | AAG | 453 |
| Ile | Lys | Ser | Pro | Cys | Gln | Arg | Glu | Thr | Pro | Glu | Gly | Ala | Glu | Ala | Lys |
|  |  |  | 100 |  |  |  |  | 105 |  |  |  |  | 110 |  |  |
| CCC | TGG | TAT | GAG | CCC | ATC | TAT | CTG | GGA | GGG | GTC | TTC | CAG | CTG | GAG | AAG | 501 |
| Pro | Trp | Tyr | Glu | Pro | Ile | Tyr | Leu | Gly | Gly | Val | Phe | Gln | Leu | Glu | Lys |
|  |  | 115 |  |  |  |  | 120 |  |  |  |  | 125 |  |  |  |
| GGT | GAC | CGA | CTC | AGC | GCT | GAG | ATC | AAT | CGG | CCC | GAC | TAT | CTC | GAC | TTT | 549 |
| Gly | Asp | Arg | Leu | Ser | Ala | Glu | Ile | Asn | Arg | Pro | Asp | Tyr | Leu | Asp | Phe |
| 130 |  |  |  |  | 135 |  |  |  |  | 140 |  |  |  |  |  |
| GCC | GAG | TCT | GGG | CAG | GTC | TAC | TTT | GGG | ATC | ATT | GCC | CTG | TGAGGAGGAC |  |  | 598 |
| Ala | Glu | Ser | Gly | Gln | Val | Tyr | Phe | Gly | Ile | Ile | Ala | Leu |
| 145 |  |  |  |  | 150 |  |  |  |  | 155 |  |  |

```
GAACATCCAA CCTTCCCAAA CGCCTCCCCT GCCCCAATCC CTTTATTACC CCCTCCTTCA    658
GACACCCTCA ACCTCTTCTG GCTCAAAAAG AGAATTGGGG CTTAGGGTC  GGAACCCAAG    718
CTTGGACTCC TGTTGATAGA TCCAGTAATG ACCTCAGAAC TCCATCTGGA TTTGTTCAGA    778
ACGCTCGGTT GCCGCCGGGG GTTTTTATT  GGTGAGAATC CAAGCTAGCT TGGCGAGATT    838
TTCAGGAGCT AAGGAAGCTA AATGGAGAA  AAAAATCACT GGATATACCA CCGTTGATAT    898
ATCCCAATGG CATCGTAAAG AACATTTGA  GGCATTTCAG TCAGTTGCTC AATGTACCTA    958
TAACCAGACC GTTACGCTGG ATATTACGGC CTTTTAAAG  ACCGTAAAGA AAAATAAGCA   1018
CAAGTTTTAT CCGGCCTTTA TTCACATTCT TGCCCGCCTG ATGAATGCTC ATCCGGAATT   1078
TCGTATGGCA ATGAAAGACG GTGAGCTGGT GATATGGGAT AGTGTTCACC CTTGTTACAC   1138
CGTTTTCCAT GAGCAAACTG AAACGTTTTC ATCGCTCTGG AGTGAATACC ACGACGATTT   1198
CCGGCAGTTT CTACACATAT ATTCGCAAGA TGTGGCGTGT TACGGTGAAA ACCTGGCCTA   1258
TTTCCCTAAA GGGTTTATTG AGAATATGTT TTCGTCTCA  GCCAATCCCT GGGTGAGTTT   1318
CACCAGTTTT GATTAAACG  TGGCCAATAT GGACAACTTC TTCGCCCCCG TTTTCACCAT   1378
GGGCAAATAT TATACGCAAG GCGACAAGGT GCTGATGCCG CTGGCGATTC AGGTTCATCA   1438
TGCCGTCTGT GATGGCTTCC ATGTCGGCAG AATGCTTAAT GAATTACAAC AGTACTGCGA   1498
TGAGTGGCAG GGCGGGGCGT AATTTTTTA  AGGCAGTTAT TGGTGCCCTT AAACGCCTGG   1558
GGTAATGACT CTCTAGCTTG AGGCATCAAA TAAAACGAAA GGCTCAGTCG AAAGACTGGG   1618
CCTTTCGTTT TATCTGTTGT TTGTCGGTGA ACGCTCTCCT GAGTAGGACA AATCCGCCGC   1678
TCTAGAGCTG CCTCGCGCGT TTCGGTGATG ACGGTGAAAA CCTCTGACAC ATGCAGCTCC   1738
CGGAGACGGT CACAGCTTGT CTGTAAGCGG ATGCCGGGAG CAGACAAGCC CGTCAGGGCG   1798
CGTCAGCGGG TGTTGGCGGG TGTCGGGGCG CAGCCATGAC CCAGTCACGT AGCGATAGCG   1858
GAGTGTATAC TGGCTTAACT ATGCCGCATC AGAGCAGATT GTACTGAGAG TGCACCATAT   1918
GCGGTGTGAA ATACCGCACA GATGCGTAAG GAGAAAATAC CGCATCAGGC GCTCTTCCGC   1978
```

| | | | | | |
|---|---|---|---|---|---|
| TTCCTCGCTC | ACTGACTCGC | TGCGCTCGGT | CTGTCGGCTG | CGGCGAGCGG | TATCAGCTCA | 2038 |
| CTCAAAGGCG | GTAATACGGT | TATCCACAGA | ATCAGGGGAT | AACGCAGGAA | AGAACATGTG | 2098 |
| AGCAAAAGGC | CAGCAAAAGG | CCAGGAACCG | TAAAAAGGCC | GCGTTGCTGG | CGTTTTTCCA | 2158 |
| TAGGCTCCGC | CCCCCTGACG | AGCATCACAA | AAATCGACGC | TCAAGTCAGA | GGTGGCGAAA | 2218 |
| CCCGACAGGA | CTATAAAGAT | ACCAGGCGTT | TCCCCCTGGA | AGCTCCCTCG | TGCGCTCTCC | 2278 |
| TGTTCCGACC | CTGCCGCTTA | CCGGATACCT | GTCCGCCTTT | CTCCCTTCGG | GAAGCGTGGC | 2338 |
| GCTTTCTCAA | TGCTCACGCT | GTAGGTATCT | CAGTTCCTG | TAGGTCGTTC | GCTCCAAGCT | 2398 |
| GGGCTGTGTG | CACGAACCCC | CCGTTCAGCC | CGACCGCTGC | GCCTTATCCG | GTAACTATCG | 2458 |
| TCTTGAGTCC | AACCCGGTAA | GACACGACTT | ATCGCCACTG | GCAGCAGCCA | CTGGTAACAG | 2518 |
| GATTAGCAGA | GCGAGGTATG | TAGGGGGTGC | TACAGAGTTC | TTGAAGTGGT | GGCCTAACTA | 2578 |
| CGGCTACACT | AGAAGGACAG | TATTTGGTAT | CTGCGCTCTG | CTGAAGCCAG | TTACCTTCGG | 2638 |
| AAAAAGAGTT | GGTAGCTCTT | GATCCGGCAA | ACAAACCACC | GCTGGTAGCG | GTGGTTTTTT | 2698 |
| TGTTTGCAAG | CAGCAGATTA | CGCGCAGAAA | AAAAGGATCT | CAAGAAGATC | CTTTGATCTT | 2758 |
| TTCTACGGGG | TCTGACGCTC | AGTGGAACGA | AAACTCACGT | TAAGGGATTT | TGGTCATGAG | 2818 |
| ATTATCAAAA | AGGATCTTCA | CCTAGATCCT | TTTAAATTAA | AAATGAAGTT | TTAAATCAAT | 2878 |
| CTAAAGTATA | TATGAGTAAA | CTTGGTCTGA | CAGTTACCAA | TGCTTAATCA | GTGAGGCACC | 2938 |
| TATCTCAGCG | ATCTGTCTAT | TTCGTTCATC | CATAGCTGCC | TGACTCCCCG | TCGTGTAGAT | 2998 |
| AACTACGATA | CGGGAGGGCT | TACCATCTGG | CCCCAGTGCT | GCAATGATAC | CGCGAGACCC | 3058 |
| ACGCTCACCG | GCTCCAGATT | TATCAGCAAT | AAACCAGCCA | GCCGGAAGGG | CCGAGCGCAG | 3118 |
| AAGTGGTCCT | GCAACTTTAT | CCGCCTCCAT | CCAGTCTATT | AATTGTTGCC | GGGAAGCTAG | 3178 |
| AGTAAGTAGT | CCGCCAGTTA | ATAGTTTGCG | CAACGTTGTT | GCCATTGCTA | CAGGCATCGT | 3238 |
| GGTCTCACGC | TCGTCGTTTG | GTATGGCTTC | ATTCAGCTCC | GGTTCCCAAC | GATCAAGGCG | 3298 |
| AGTTACATGA | TCCCCCATGT | TGTGCAAAAA | AGCGGTTAGC | TCCTTCGGTC | CTCCGATCGT | 3358 |
| TGTCAGAAGT | AAGTTGGCCG | CAGTGTTATC | ACTCATGGTT | ATGGCAGCAC | TGCATAATTC | 3418 |
| TCTTACTGTC | ATGCCATCCG | TAAGATGCTT | TTCTGTGACT | GGTGAGTACT | CAACCAAGTC | 3478 |
| ATTCTGAGAA | TAGTGTATGC | GGCGACCGAG | TTGCTCTTGC | CCGGCGTCAA | TACGGGATAA | 3538 |
| TACCGCGCCA | CATAGCAGAA | CTTTAAAAGT | GCTCATCATT | GGAAAACGTT | CTTCGGGGCG | 3598 |
| AAAACTCTCA | AGGATCTTAC | CGCTGTTGAG | ATCCAGTTCG | ATGTAACCCA | CTCGTGCACC | 3658 |
| CAACTGATCT | TCAGCATCTT | TTACTTTCAC | CAGCGTTTCT | GGCTGAGCAA | AACAGGAAG | 3718 |
| GCAAAATGCC | GCAAAAAAGG | GAATAAGGGC | GACACGGAAA | TGTTGAATAC | TCATACTCTT | 3778 |
| CCTTTTTCAA | TATTATTGAA | GCATTTATCA | GGGTTATTGT | CTCATGAGCG | GATACATATT | 3838 |
| TGAATGTATT | TAGAAAAATA | AACAAATAGG | GGTTCCGCGC | ACATTTCCCC | GAAAAGTCCC | 3898 |
| ACCTGACGTC | TAAGAAACCA | TTATTATCAT | GACATTAACC | TATAAAAATA | GGCGTATCAC | 3958 |
| GAGGCCCTTT | CGTCTTCAC | | | | | 3977 |

( 2 ) INFORMATION FOR SEQ ID NO:14:

( i ) SEQUENCE CHARACTERISTICS:
        ( A ) LENGTH: 3740 base pairs
        ( B ) TYPE: nucleic acid
        ( C ) STRANDEDNESS: single
        ( D ) TOPOLOGY: linear ( i i ) MOLECULE TYPE: DNA (recombinant plasmid)

( i x ) FEATURE:

(A) NAME/KEY: CDS
(B) LOCATION: complement (2613..one- of(1532))
(D) OTHER INFORMATION: /note="Contains coding region for the lacI gene beginning at residue 2613 to 1532"

(xi) SEQUENCE DESCRIPTION: SEQ ID NO:14:

| | | | | | | |
|---|---|---|---|---|---|---|
| AAGCTTCACG | CTGCCGCAAG | CACTCAGGGC | GCAAGGGCTG | CTAAAGGAAG | CGGAACACGT | 60 |
| AGAAAGCCAG | TCCGCAGAAA | CGGTGCTGAC | CCCGGATGAA | TGTCAGCTAC | TGGGCTATCT | 120 |
| GGACAAGGGA | AAACGCAAGC | GCAAAGAGAA | AGCAGGTAGC | TTGCAGTGGG | CTTACATGGC | 180 |
| GATAGCTAGA | CTGGGCGGTT | TTATGGACAG | CAAGCGAACC | GGAATTGCCA | GCTGGGGCGC | 240 |
| CCTCTGGTAA | CGTTGGGAAG | CCCTGCAAAG | TAAACTGGAT | GGCTTTCTTG | CCGCCAAGGA | 300 |
| TCTGATGGCG | CAGGGGATCA | AGATCTGATC | AAGAGACAGG | ATGACGGTCG | TTTCGCATGC | 360 |
| TTGAACAAGA | TGGATTGCAC | GCAGGTTCTC | CGGCCGCTTG | GGTCGAGAGG | CTATTCGGCT | 420 |
| ATGACTGGGC | ACAACAGACA | ATCCGCTGCT | CTGATGCCGC | CGTGTTCCGG | CTGTCAGCCC | 480 |
| AGGGGCGCCC | GGTTCTTTTT | GTCAAGACCG | ACCTGTCCGG | TGCCCTGAAT | GAACTGCAGG | 540 |
| ACGAGGCAGC | GCGGCTATCG | TGGCTGGCCA | CGACGGGCGT | TCCTTGCGCA | GCTGTGCTCG | 600 |
| ACGTTGTCAC | TGAAGCGGGA | AGGGACTGGC | TGCTATTGGG | CGAAGTGCCG | GGCAGGATC | 660 |
| TCCTGTCATC | TCACCTTGCT | CCTGCCGAGA | AAGTATCCAT | CATGGCTGAT | GCAATGCGGC | 720 |
| GGCTGCATAC | GCTTGATCCG | GCTACCTGCC | CATTCGACCA | CCAAGCGAAA | CATCGCATCG | 780 |
| AGCGAGCACG | TACTCGGATG | GAAGCCGGTC | TTGTCGATCA | GGATCATCTG | GACGAAGAGC | 840 |
| ATCAGGGGCT | CGCGCCAGCC | GAACTGTTCG | CCAGGCTCAA | GGCGCGCATG | CCCGACGGCG | 900 |
| AGGATCTCGT | CGTGACCCAT | GGCGATGCCT | GCTTGCCGAA | TATCATGGTG | GAAAATGGCC | 960 |
| GCTTTTCTGG | ATTCATCGAC | TGTGGCCGGC | TGGGTGTGGC | GGACCGCTAT | CAGGACATAG | 1020 |
| CGTTGGCTAC | CCGTGATATT | GCTGAAGAGC | TTGGCGGCGA | ATGGGCTGAC | CGCTTCCTCG | 1080 |
| TGCTTTACGG | TATCGCCGCT | CCCGATTCGC | AGCGCATCGC | CTTCTATCGC | CTTCTTGACG | 1140 |
| AGTTCTTCTG | AGCGGGACTC | TGGGGTTCGA | AATGACCGAC | CAAGCGACGC | CCAACCTGCC | 1200 |
| ATCACGAGAT | TTCGATTCCA | CCGCCGCCTT | CTATGAAAGG | TTGGGCTTCG | GAATCGTTTT | 1260 |
| CCGGGACGCC | GGCTGGATGA | TCCTCCAGCG | CGGGGATCTC | ATGCTGGAGT | TCTTCGCCCA | 1320 |
| CCCCGGGCTC | GATCCCCTCG | CGAGTTGGTT | CAGCTGCTGC | CTGAGGCTGG | ACGACCTCGC | 1380 |
| GGAGTTCTAC | CGGCAGTGCA | AATCCGTCGG | CATCCAGGAA | ACCAGCAGCG | GCTATCCGCG | 1440 |
| CATCCATGCC | CCCGAACTGC | AGGAGTGGGG | AGGCACGATG | GCCGCTTTGG | TCGACAATTC | 1500 |
| GCGCTAACTT | ACATTAATTG | CGTTGCGCTC | ACTGCCCGCT | TTCCAGTCGG | GAAACCTGTC | 1560 |
| GTGCCAGCTG | CATTAATGAA | TCGGCCAACG | CGCGGGGAGA | GGCGGTTTGC | GTATTGGGCG | 1620 |
| CCAGGGTGGT | TTTTCTTTTC | ACCAGTGAGA | CGGGCAACAG | CTGATTGCCC | TTCACCGCCT | 1680 |
| GGCCCTGAGA | GAGTTGCAGC | AAGCGGTCCA | CGCTGGTTTG | CCCCAGCAGG | CGAAAATCCT | 1740 |
| GTTTGATGGT | GGTTAACGGC | GGGATATAAC | ATGAGCTGTC | TTCGGTATCG | TCGTATCCCA | 1800 |
| CTACCGAGAT | ATCCGCACCA | ACGCGCAGCC | CGGACTCGGT | AATGGCGCGC | ATTGCGCCCA | 1860 |
| GCGCCATCTG | ATCGTTGGCA | ACCAGCATCG | CAGTGGGAAC | GATGCCCTCA | TTCAGCATTT | 1920 |
| GCATGGTTTG | TTGAAAACCG | GACATGGCAC | TCCAGTCGCC | TTCCCGTTCC | GCTATCGGCT | 1980 |
| GAATTTGATT | GCGAGTGAGA | TATTTATGCC | AGCCAGCCAG | ACGCAGACGC | GCCGAGACAG | 2040 |
| AACTTAATGG | GCCCGCTAAC | AGCGCGATTT | GCTGGTGACC | CAATGCGACC | AGATGCTCCA | 2100 |
| CGCCCAGTCG | CGTACCGTCT | TCATGGGAGA | AAATAATACT | GTTGATGGGT | GTCTGGTCAG | 2160 |
| AGACATCAAG | AAATAACGCC | GGAACATTAG | TGCAGGCAGC | TTCCACAGCA | ATGGCATCCT | 2220 |

```
GGTCATCCAG  CGGATAGTTA  ATGATCAGCC  CACTGACGCG  TTGCGCGAGA  AGATTGTGCA    2280

CCGCCGCTTT  ACAGGCTTCG  ACGCCGCTTC  GTTCTACCAT  CGACACCACC  ACGCTGGCAC    2340

CCAGTTGATC  GGCGCGAGAT  TTAATCGCCG  CGACAATTTG  CGACGGCGCG  TGCAGGGCCA    2400

GACTGGAGGT  GGCAACGCCA  ATCAGCAACG  ACTGTTTGCC  CGCCAGTTGT  TGTGCCACGC    2460

GGTTGGGAAT  GTAATTCAGC  TCCCCCATCG  CCGCTTCCAC  TTTTTCCCGC  GTTTTCGCAG    2520

AAACGTGGCT  GGCCTGGTTC  ACCACGCGGG  AAACGGTCTG  ATAAGAGACA  CCGGCATACT    2580

CTGCGACATC  GTATAACGTT  ACTGGTTTCA  CATTCACCAC  CCTGAATTGA  CTCTCTTCCG    2640

GGCGCTATCA  TGCCATACCG  CGAAAGGTTT  TGCGCCATTC  GATGGTGTCA  ACGTAAATGC    2700

ATGCCGCTTC  GCCTTCGCCC  GCGAATTGTC  GACCCTGTCC  CTCCTGTTCA  GCTACTGACG    2760

GGGTGGTGCG  TAACGGCAAA  AGCACCGCCG  GACATCAGCG  CTAGCGGAGT  GTATACTGGC    2820

TTACTATGTT  GGCACTGATG  AGGGTGTCAG  TGAAGTGCTT  CATGTGGCAG  GAGAAAAAAG    2880

GCTGCACCGG  TGCGTCAGCA  GAATATGTGA  TACAGGATAT  ATTCCGCTTC  CTCGCTCACT    2940

GACTCGCTAC  GCTCGGTCGT  TCGACTGCGG  CGAGCGGAAA  TGGCTTACGA  ACGGGCGGA    3000

GATTTCCTGG  AAGATGCCAG  GAAGATACTT  AACAGGGAAG  TGAGAGGGCC  GCGGCAAAGC    3060

CGTTTTTCCA  TAGGCTCCGC  CCCCCTGACA  AGCATCACGA  AATCTGACGC  TCAAATCAGT    3120

GGTGGCGAAA  CCCCACAGGA  CTATAAAGAT  ACCAGGCGTT  TCCCCTGGCG  GCTCCCTCGT    3180

GCGCTCTCCT  GTTCCTGCCT  TTCCGTTTAC  CGGTGTCATT  CCGCTGTTAT  GGCCGCGTTT    3240

GTCTCATTCC  ACGCCTGACA  CTCAGTTCCG  GGTAGGCAGT  TCGCTCCAAG  CTGGACTGTA    3300

TGCACGAACC  CCCCGTTCAG  TCCGACCGCT  GCGCCTTATC  CGGTAACTAT  CGTCTTGAGT    3360

CCAACCCGGA  AAGACATGCA  AAAGCACCAC  TGGCAGCAGC  CACTGGTAAT  TGATTTAGAG    3420

GAGTTAGTCT  TGAAGTCATG  CGCCGGTTAA  GGCTAAACTG  AAAGGACAAG  TTTTCGTCAC    3480

TGCGCTCCTC  CAAGCCAGTT  ACCTCGGTTC  AAAGAGTTGG  TAGCTCAGAG  AACCTTCGAA    3540

AAACCGCCCT  GCAAGGCGGT  TTTTTCGTTT  TCAGAGCAAG  AGATTACGCG  CAGACCAAAA    3600

CGATCTCAAG  AAGATCATCT  TATTAATCAG  ATAAAATATT  TCTAGATTTC  AGTGCAATTT    3660

ATCTCTTCAA  ATGTAGCACC  TGAAGTCAGC  CCCATACGAT  ATAAGTTGTT  AATTCTCATG    3720

TTTGACAGCT  TATCATCGAT                                                    3740
```

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: 1..22
        ( D ) OTHER INFORMATION: /function="Oligonucleotide used for
            gap duplex mutagenesis"
        / note="Used to create Ser(29)-mutein of TNF-alpha"

( x i ) SEQUENCE DESCRIPTION: SEQ ID NO:15:

```
CCGGCGGTTG  GACCACTGGA  GC                                                  22
```

( 2 ) INFORMATION FOR SEQ ID NO:16:

( i ) SEQUENCE CHARACTERISTICS:
        ( A ) LENGTH: 19 base pairs ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: 1..19
        ( D ) OTHER INFORMATION: /function="Oligonucleotide used for
            gap duplex mutagenesis"
            / note="Used to create Trp(32)-mutein of TNF-alpha"

( x i ) SEQUENCE DESCRIPTION: SEQ ID NO:16:

CATTGGCCCA GCGGTTCAG                                                    19

( 2 ) INFORMATION FOR SEQ ID NO:17:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: 1..32
        ( D ) OTHER INFORMATION: /function="Oligonucleotide used for
            gap duplex mutagenesis"
            / note="Used to create Ser(29)Trp(32)-mutein of
            TNF-alpha"

( x i ) SEQUENCE DESCRIPTION: SEQ ID NO:17:

GGGCATTGGC CCAGCGGTTG GACCACTGGA GC                                     32

( 2 ) INFORMATION FOR SEQ ID NO:18:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: 1..50
        ( D ) OTHER INFORMATION: /function="Oligonucleotide used for
            gap duplex mutagenesis"
            / note="Used to create any position 29-mutein of
            TNF-alpha"

( x i ) SEQUENCE DESCRIPTION: SEQ ID NO:18:

CCACGCCATT CGCGAGGAGG GCATTGGCCC GGCGGTTNNN CCACTGGAGC                  50

( 2 ) INFORMATION FOR SEQ ID NO:19:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: 1..42
        ( D ) OTHER INFORMATION: /function="Oligonucleotide used for
            gap duplex mutagenesis"
            / note="Used to create any position 32-mutein of TNF-alpha"

( x i ) SEQUENCE DESCRIPTION: SEQ ID NO:19:

CCACGCCATT CGCGAGGAGG GCATTGGCNN NGCGGTTCAG CC                       42

( 2 ) INFORMATION FOR SEQ ID NO:20:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: complement (1..22)
        ( D ) OTHER INFORMATION: /function="PCR primer"
            / note="Complementary to positions 3949 to 3970 of
            Sequence ID No. 2"

( x i ) SEQUENCE DESCRIPTION: SEQ ID NO:20:

GGCGTATCAC GAGGCCCTTT CG                                             22

( 2 ) INFORMATION FOR SEQ ID NO:21:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: 1..22
        ( D ) OTHER INFORMATION: /function="PCR primer"
            / note="Complementary to positions
            748 - 727 of Seq. ID No. 2"

( x i ) SEQUENCE DESCRIPTION: SEQ ID NO:21:

CATTACTGGA TCTATCAACA GG                                             22

( 2 ) INFORMATION FOR SEQ ID NO:22:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: 1..36
        ( D ) OTHER INFORMATION: /function="PCR primer"
            / product="primer 21/M5"
            / note="PCR primer which is complementary to
            positions 219-184 of Seq. ID No. 2 with mismatched
            residues at positions 10-12."

( x i ) SEQUENCE DESCRIPTION: SEQ ID NO:22:

ATTGGCCCGC TCGTTCAGCC ACTGGAGCTG CCCCTC                              36

( 2 ) INFORMATION FOR SEQ ID NO:23:

( i ) SEQUENCE CHARACTERISTICS:
        ( A ) LENGTH: 36 base pairs
        ( B ) TYPE: nucleic acid ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: 1..36
        ( D ) OTHER INFORMATION: /function="PCR primer for
            mutagenesis"
            / note="PCR primer for mutagenesis which is
            complementary to positions 219-184 of Seq. ID No.
            2 with mismatched bases at positions 7-9 and 11-12

( x i ) SEQUENCE DESCRIPTION: SEQ ID NO:23:

ATTGGCAGTG TTGTTCAGCC ACTGGAGCTG CCCCTC                                  3 6

( 2 ) INFORMATION FOR SEQ ID NO:24:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( i x ) FEATURE:
        ( A ) NAME/KEY: misc_feature
        ( B ) LOCATION: 1..22
        ( D ) OTHER INFORMATION: /function="PCR primer"
            / product="primer 21/MR"
            / note="PCR primer used in conjunction with Seq.
            ID Nos. 22 & 23 to create muteins of TNF-alpha"

( x i ) SEQUENCE DESCRIPTION: SEQ ID NO:24:

GCCCTCCTGG CCAATGGCGT GG                                                 2 2

DNAS ENCODING TUMOR NECROSIS FACTOR-α MUTEINS

This is a division of application Ser. No. 07/794,400 filed Nov. 20, 1991, now U.S. Pat. No. 4,422,104.

BACKGROUND OF INVENTION

Tumor Necrosis Factor, or more specifically Tumor Necrosis Factor-alpha, is a cytokine, primarily produced by stimulated macrophages, that exhibits not only a striking cytotoxicity against various tumour cells [Carswell et al., Procd. Nat. Acad. Sci., U.S.A. 72, 3666–3670, (1975)] but also plays a multiple role as a mediator of inflammation and the immune response [See Beutler and Cerami, Ann. Rev. Immunol. 7, 625–655 (1989); Bonavista and Granger (eds.) "Tumor Necrosis Factor: Structure, Mechanism of Action, Role in Disease and Therapy", Karger, Basel (1990)]. The primary structure of human Tumor Necrosis Factor-alpha (hTNF-α) has been deduced from the nucleotide sequence of a cDNA which has been cloned and expressed in *E. coli* [Pennica et al., Nature 912, 724–729 (1984); Marmenout et al., Europ. J. Biochem. 152, 515–522 (1985); Wang et al., Science 228, 149–154 (1985); Shirai et al., Nature 313, 803–806 (1985)]. A striking homology in amino acid sequence (30%) was found between hTNF-α and human Lymphotoxin, often referred to as human Tumor Necrosis Factor-beta (hTNF-β), a cytokine produced by a subset of lymphocytes [Gray et al., Nature 312, 721–724 (1984); Fiers et al., Cold Spring Harbour Symp. 51, 587–595 (1986)].

hTNF-α with modified amino acid sequences, so called TNF-α-muteins, have also been described in the art [See, e.g., Yamagishi et al., Protein Engineering 3, 713–719, (1990) or by Fiers in "Tumor Necrosis Factors: Structure, Function and Mechanism of Action", Aggarwal and Vilcek (eds.), Marcel Dekker, Inc., New York, (in press), or by Fiers et al. in Bonavista and Granger, pp. 77–81 Supra. In addition TNF-α-muteins have also been the object of several patent applications, for example, International Patent Applications Publ. Nos. WO 86/02381, WO 86/04606, WO 88/06625 and European Patent Applications Publ. Nos. 155,549; 158,286; 168,214; 251,037 and 340,333, and Deutsche Offenlegungsschrift Nr. 3843534.

Muteins of Lymphotoxin have also been disclosed in the art, for example in European Patent Applications Publ. Nos. 250,000; 314,094 and 336,383.

The biological effects of TNF are mediated via specific receptors, namely a receptor with an apparent molecular weight of 55 kD on sodium dodecylsulfate polyacrylamide gel electrophoresis (SDS-PAGE) (p55-TNF-R) and a receptor with an apparent molecular weight of 75 kD on SDS-PAGE (p75-TNF-R). Both forms of TNF-receptors have been cloned previously. The cloning of p55-TNF-R was done by Loetscher et al. [Cell 61, 351–359, (1990)] and the cloning of p75-TNF-R was done by Dembic et al. [Cytokine 2, 53–58, (1990)] See also European Patent Application No. 90116707.2 (both receptors). It was found more recently that both receptors bind not only TNF-α, but also TNF-β with high affinity [Schönfeld et al., J. Biol. Chem. 266, 3863–3869 (1991)].

SUMMARY OF THE INVENTION

An object of the present invention is a mutein or a pharmaceutically acceptable salt thereof of human Tumor Necrosis Factor having an amino acid sequence which is changed by deletion, insertion and/or substitution of one or more amino acids such that the mutein shows a significant difference between its binding affinity to the human p75-Tumor-Necrosis-Factor-Receptor and the human p55-Tumor-Necrosis-Factor-Receptor.

A preferred embodiment of the present invention is a mutein as defined above on the basis of the amino acid sequence of TNF-α as disclosed by Pennica et al; supra, namely [SEQ, ID No: 1]

```
  1                                           10
VAL ARG SER SER SER ARG THR PRO SER ASP LYS PRO VAL ALA HIS
                        20                                                30
VAL VAL ALA ASN PRO GLN ALA GLU GLY GLN LEU GLN TRP LEU ASN
                                        40
ARG ARG ALA ASN ALA LEU LEU ALA ASN GLY VAL GLU LEU ARG ASP
                    50                                                60
ASN GLN LEU VAL VAL PRO SER GLU GLY LEU TYR LEU ILE TYR SER
                                    70
GLN VAL LEU PHE LYS GLY GLN GLY CYS PRO SER THR HIS VAL LEU
                80                                              90
LEU THR HIS THR ILE SER ARG ILE ALA VAL SER TYR GLN THR LYS
                                100
VAL ASN LEU LEU SER ALA ILE LYS SER PRO CYS GLN ARG GLU THR
                110                                             120
PRO GLU GLY ALA GLU ALA LYS PRO TRP TYR GLU PRO ILE TYR LEU
                                130
GLY GLY VAL PHE GLN LEU GLU LYS GLY ASP ARG LEU SER ALA GLU
                140                                             150
ILE ASN ARG PRO ASP TYR LEU ASP PHE ALA GLU SER GLY GLN VAL
                        157
TYR PHE GLY ILE ILE ALA LEU
``` or as disclosed by Marmenout et al. supra or Wang et al. supra or Shirai et al. supra. More specifically muteins of deduced amino acid sequence as are coded for by the nucleotide sequence of the insert of the plasmid pDS56/RBSII,Sph1-TNFα[SEQ ID No: 2] (See also FIG. 5 and 6A–6C) coding for mature TNF-α.

Another preferred embodiment of the present invention is a mutein as defined above wherein the TNF-α amino acid sequence is changed by substitution of one or more amino acids, preferably one or two by other amino acids, and preferably by naturally occuring amino acids.

Another preferred embodiment is a human Tumor Necrosis Factor mutein wherein SEQ ID NO: 1 is changed by deletion, insertion, substitution or combinations thereof, of between one and 10 amino acids.

A more preferred embodiment of the present invention are muteins as defined above wherein the TNF-α amino acid sequence is substituted at position 29 and/or 32 or position 31 and 32 or position 31 or position 29 and 31 whereby substitutions at position 29 and/or 32 or position 31 and 32 or position 31 are preferred (referring to [SEQ ID No: 1]) by other amino acids, preferably naturally occuring amino acids. Any amino acid, preferably any naturally occuring one, can be used at one or more of these positions which leads to a TNF-mutein showing a significant difference between its binding affinity to the human p75-TNF-R and the human p55-TNF-R. For substitutions at position 29 serine [SEQ ID No: 4], glycine [SEQ ID No: 5] or tyrosine [SEQ ID No: 6] are preferred, serine is especially preferred, for example in case of a single position mutein at position 29 (Ser$^{29}$-TNFα) [SEQ ID No: 4]. For substitutions at position 31 glutamic acid, for example Glu$^{31}$-TNFα [SEQ ID No :7], or asparagine [SEQ ID No: 8] are preferred. For substitutions at position 32 tyrosine, for example Tyr$^{32}$-TNFα [SEQ ID No: 10] or tryptophan, for example Trp$^{32}$-TNFα [SEQ ID No: 9] are preferred, Trp$^{32}$ is specifically preferred. Especially preferred substitutions in case of a double position mutein at positions 29 and 32 are Ser$^{29}$-Trp$^{32}$-TNFα [SEQ ID No: 12] and at position 31 and 32 are Asn$^{31}$-Thr$^{32}$-TNFα. [SEQ ID No: 11]. It is understood that the muteins of the present invention can also be prepared by methods known in the art of chemical peptide and protein synthesis, for example by partial or total liquid or solid phase synthesis as described by Gross and Meyenhofer in "The Peptides" Vols. 1–9, Academic Press, Inc., Harcourt Brace Jovanovich, Publs., San Diego (1979–1987) or by Field' and Nobel, Int. J. Pept. Prot. Res. 35, 161–214 (1990).

Another preferred embodiment of the present invention is a mutein of TNF-α comprising the amino acid sequence set forth in SEQ ID No: 1 wherein at lease one of the positions 29, 31 or 32 is substituted with any naturally occurring amino acid different from the corresponding amino acid in SEQ ID No: 1.

Analogs obtained by deletion, substitution or addition or combinations thereof of one or several amino acids from or to the muteins as defined in the previous paragraph, whereby position 29 and/or 32 or position 31 or position 31 and 32 in the mutein are not changed and which analogs still show a significant difference between its binding affinity to the human p75-TNF-R and the human p55-TNF-R are also an object of the present invention. With respect to such substitution analogs, amino acid substitutions in proteins which do not generally alter the activity are known in the state of the art and are described, for example, by H. Neurath and R. L. Hill in "The Proteins" (Academic Press, New York, 1979, see especially FIG. 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse (the three letter abbreviations are used for amino acids and are standard and known in the art).

Analogs made by substitution, addition, deletion or combinations thereof can be produced by methods known in the art and described for example in Sambrook et al. [Molecular Cloning, A Laboratory Manual, 2nd ed., Cold Spring Harbour Laboratory, Cold Spring Harbour Laboratory Press, USA (1989)] or as described herein. Whether such an analog still shows the significant difference between its binding affinity to the p75-TNF-R and the p55-TNF-R can be determined as described below and more specifically in Examples III1) and 2) or Example VIII. Furthermore, salts of such muteins and analogs are also an object of the present invention. Such salts can be produced by methods known in the art.

It is furthermore an object of the present invention to provide a mutein as described above for the treatment of illnesses, for example cancer.

It is well known in the art that on the basis of its biological activities TNF-α can be a valuable compound for the treatment of various disorders. For example TNF-α, alone or in combination with interferon, can be an effective antitumor agent [Brouckaert et al., Int. J. Cancer 38, 763–769 (1986)]. However, its systemic toxicity is a major limitation to its wider therapeutic use [Taguchi T. and Sohmura Y.; Biotherapy 3, 177–186 (1991)].

The discovery of two TNF-receptors with (putatively) distinct functional roles should allow one to separate in a given disease state the benefical and unwanted biological responses to TNF. There is circumstantial evidence supporting the feasibility of this approach. It has been shown for example [Brouckaert et al., Agents and Actions 26, 196–197 (1989); Everaerdt, B. et al., Biochem. Biophys. Res. Comm. 163, 378–385 (1989)] that in mice, murine TNF-α (mTNF-α) is up to 50-fold more toxic than human TNF-α (hTNF-α), although when tested in cell culture (murine and human), both are equally active on sensitive cell lines.

It is believed that the strategy of separating beneficial and unwanted TNFα activities by using compounds specifically binding to one or the other TNF-receptor, such as the TNF-muteins of the present invention, can be used in general in other disease states where TNF plays a role.

DNA-sequences comprising a DNA-sequence coding for TNF-muteins as hereinbefore described are also an object of the present invention. Such DNA-sequences can be constructed starting from genomic-or cDNA-sequences coding for hTNF as disclosed in the art using known methods of in vitro mutagenesis [see e.g. Sambrook et al., 1989]. Such mutagenesis can be carried out at .random in order to obtain a large number of mutants which can then be tested for their desired properties in appropriate assay systems or, in order to mutate defined positions .in a given DNA-sequence, by so called site directed mutagenesis [see, e.g., Sambrook et al., 1989, 15.51–15.113] or by mutagenesis using the polymerase chain reaction [see, e.g., White et al., Trends in Genetics 5, 185–189 (1989)].

A preferred embodiment of the invention is a purified and isolated DNA sequence, comprising positions 115 to 591 of SEQ ID NO:2 wherein the DNA sequence is changed by deletion, insertion, substitution or combinations thereof, such that the DNA sequence codes for a human Tumor Necrosis Factor mutein containing at least one amino acid different from SEQ ID No: 1 and the mutein shows a significant difference between its binding affinity to the human p75-(Tumor Necrosis Factor)-Receptor and to human p55-(Tumor Necrosis Factor)-Receptor.

Another preferred embodiment is a purified and isolated DNA sequence comprising positions 115 to 591 of SEQ ID No: 13 wherein at least one of the codons at positions 202 to 204, 208 to 210, or 211 to 213 codes for an amino acid different from the amino acid coded for by the corresponding condon in SEQ ID No: 2.

One chemical mutagen which is often used for random mutagenesis is sodium bisulfite which converts cytosin residues into uracil residues and hence leads to a transition of "C" to "T" (standard abbreviations for nucleotides) [for the method see e.g. Shortle and Nathans, Procd. Nat. Acad. Sci. U.S.A. 75, 2170–2174 (1978) or Pine and Huang, Meth. Enzym. 154, 415–430 (1987)]. This mutagen acts solely on single stranded DNA whereas the expression of the mutated target DNA sequence is achieved with a double stranded plasmid vector. One possibility to avoid the necessity of recloning in mutagenesis and expression vectors is the use of so called "phasmids". These are vectors which, in addition to a plasmid origin of replication, carry also an origin of replication derived from a filamentous phage. Examples of such phasmids are the pMa-and pMc-phasmids as described by Stanssen et al. [Nucleic Acids Res. 17, 4441–4454, (1989)]. Using this expression system one can construct so called "gap-duplex"-structures [see also Kramer et al., Nucl. Acids. Res. 12, 9441–9456 (1984)] where only the TNF-coding sequence is in a single stranded configuration and therefore accessible for the specific chemical mutagen. "Gap-duplexes" to be used in at random mutagenesis can be constructed as described for site-specific mutagenesis by Stanssen et al. supra with the exception that the (−)strand contains the same active antibiotic resistance gene as the (+)strand. By making use of different restriction sites in the DNA-sequence encoding hTNFα [SEQ ID No: 2], variation of the width of the gap is possible. Examples of such restriction sites are the Cla1-Sal1 sites (470 nucleotides), BstX1-BstX1 sites (237 nucleotides) or Styl-Styl sites (68 nucleotides). Such gap-duplex-constructs can then be treated with increasing concentrations (up to 4M) of bisulfite, followed by several dialysis steps, as described by Shortle and Nathans supra. A suitable procaryotic host cell can then be transformed by such phasmid constructs according to methods known in the art and described for example by Sambrook et al. supra. A suitable procaryotic host cell means in this context a host cell deficient in a specific repair function so that an uracil residue is maintained in the DNA during replication and which host cell is capable of expressing the corresponding mutated TNF. Such specific host strains are known in the art, for example for *E. coli* strains, e.g. *E.* coil BW 313 [Kunkel, T. A., Procd. Natl. Acad. Sci. USA 82, 488–492 (1985)]. The resulting clones can then be screened for those expressing a desired TNF-mutein by appropriate assay systems. For example each colony can be inoculated in a microtiterplate in a suitable medium containing the relevant antibiotic. The cells may be lysed by addition of lysozyme, followed by sequential freeze-thaw cycles. After precipitation of nucleic acids and centrifugation, the supernatant of each colony can directly be used in appropriate assays as described, for example, in Example IIa and IIb or Example VIII measuring binding to the p75-TNF-R and the p55-TNF-R on the surface of living cells or in purified form.

If desired, the specific sites of mutation can be determined, for example by restriction fragment analysis [see, e.g., Sambrook et al. supra]. By determination of the DNA-sequence of such fragments the exact position of the mutation can be determined and if such mutation leads to an amino acid replacement the new amino acid can be derived from the determined DNA:sequence. DNA-sequencing can be performed according to methods known in the art, for example by using T7 polymerase on supercoiled DNA with a commercially available sequencing kit (Pharmacia, Uppsala, Sweden).

As already mentioned above, another possibility of mutating a given DNA-sequence is by "site directed mutagenesis". A widely used strategy for such kind of mutagenesis as originally outlined by Hutchinson and Edgell [J. Virol. 8, 181 (1971)] involves the annealing of a synthetic oligonucleotide carrying the desired nucleotide substitution to a target region of a single stranded DNA-sequence wherein the mutation should be introduced [for review see Smith, Annual. Rev. Genet. 19, 423 (1985) and for improved methods see references 2–6 in Stanssen. et al. supra. (1989)].

One such preferred method is the one of Stanssen et al. supra (1989) using "gapped duplex DNA" as originally described by Kramer et al. supra (1984) [see also Kramer and Fritz, Methods in Enzymology, (1987), Academic Press, Inc., USA], but using antibiotic resistance genes instead of M13 functional genes for selection of the mutation containing strand as well as the phasmid-technology described by Stanssen et al. supra (1989). An advantage of this method lies also in the capability of performing successive cycles of mutagenesis without the need to transfer the gene to a new mutagenesis vector. The second round mutagenesis differs only in the selection using another antibiotic marker (Stanssen et al., supra). As a control, site-specific back mutagenesis of the mutant to the wild-type TNF can be used. In addition, the use of an oligonucleotide, creating or destroying a restriction site in the TNF gene, allows one to control the mutant not only by hybridization to the oligonucleotide used for site directed mutagenesis but also by the presence or absence of the restriction site. In order to create a set of TNF-muteins wherein at a defined position of their amino acid sequence the wild-type amino acid, is replaced by any naturally occurring amino acid a set of oligonucleotides is used with all possible codons at the defined position.

As already mentioned above, another possibility of mutating a given DNA-sequence is the mutagenesis by using the polymerase chain reaction (PCR). The principle of this method is outlined by White et al. supra (1989), whereas improved methods are described in Innis et al. [PCR Protocols: A Guide to Methods and Applications, Academic Press, Inc. (1990)].

PCR is an in vitro method for producing large amounts of a specific DNA fragment of defined length and sequence from small amounts of a template DNA. PCR is based on the enzymatic amplification of the DNA fragment which is flanked by two oligonucleotide primers that hybridize to opposite strands of the target sequence. The primers are oriented with their 3' ends pointing towards each other. Repeated cycles of heat denaturation of the template, annealing of the primers to their complementary sequences and extension of the annealed primers with a DNA polymerase result in the amplification of the segment defined by the 5' ends of the PCR primers. Since the extension product of each primer can serve as a template for the other, each cycle essentially doubles the amount of the DNA fragment produced in the previous cycle. Since the primers are physically incorporated into the amplified product and mismatches between the 5' end of the primer and the template do not significantly affect the efficiency of the amplification, it is possible to alter the amplified sequence thereby introducing the desired mutation into the amplified DNA. By utilizing the thermostable Taq DNA polymerase isolated from the thermophilic bacteria *Thermus aquaticus*, it has been possible to avoid denaturation of the polymerase which necessitated the addition of enzyme after each heat denaturation step. This development has led to the automation of PCR by a variety of simple temperature-cycling devices. In addition, the specificity of the amplification reaction is increased by allowing the use of higher temperatures for primer annealing and extension. The increased specificity improves the overall yield of amplified products by minimizing the competition from non-target fragments for enzyme and primers.

Design and synthesis of oligonucleotides can be effected as known in the art and described, for example, in Sambrook et al. supra (1989) or in one of the references cited above with respect to site-directed mutagenesis.

As soon as a DNA-sequence coding for a TNF-mutein of the present invention has been created, expression can be effected by the phasmid technology as described above or by use of any suitable pro- or eukaryotic expression system well known in the art [see, e.g., Sambrook et al., supra].

Expression is effected preferably in prokaryotic cells, for example, in E. coli, Bacillus subtilis and so on, whereby E. coli, specifically E. coli K12 strains for example M15 [described as DZ 291 by Villarejo et al. in J. Bacteriol. 120, 466–474 (1974)], HB 101 [ATCC No. 33694], WK6 (Stanssens et al. supra) or E. coli SG13009 [Gottesman et al., J. Bacteriol. 148, 265–273 (1981)] are preferred. Expression of the muteins of the present invention can also be effected in lower or higher eukaryotic cells, like for example yeast cells (like Saccharomyces, Pichia etc.), filamentous fungi (like Aspergillus etc.) or cell lines (like chinese hamster ovary cell lines etc.), whereby expression in yeast cells is preferred [see Sreekrishna et al., Biochem. 28, 4117–4125, (1989); Hitzeman et al., Nature 293, 717–722 (1981); European Patent Application Publication No. 263 311]. Expression of the TNF-muteins of the present invention may occur in such systems either intracellularly, or, after suitable adaption of the gene, extracellularly (see Leemans et al., Gene 85, 99–108, 1989).

Suitable vectors used for expression in E. coil are mentioned e.g. by Sambrook et al. [supra] or by Fiers et al. in "Procd. 8th Int. Biotechnology Symposium" [Soc. Franc. de Microbiol., Paris, (Durand et al., eds.), pp. 680–697 (1988)] or and more specifically vectors of the pDS family [Bujard et al., Methods in Enzymology, eds. Wu and Grossmann, Academic Press, Inc. Vol. 155, 416–433 (1987); Stüber et al., Immunological Methods, eds. Lefkovits and Pernis, Academic Press, Inc., Vol. IV, 121–152 (1990)] like, for example, pDS56/RBSII,Sph1-TNFαSer29 or pDS56/RBSII,Sph1TNFαTrp32 (see Example I) or pDS56/RBSII, Sph1-TNFαGlu31 or pDS56/RBSII,Sph1-TNFαAsn31Thr32 (see Example VII). The transformed E. coli strains M15 (pREP4;pDS56/RBSII,Sph1-TNFαGlu31) and M15 (pREP4;pDS56/RBSII,Sph1-TNFαAsn31Thr32) have been deposited under the Budapest Treaty for patent purposes at the-Deutsche Sammlung yon Mikroorganismen und Zellkulturen GmbH (DSM) in Braunschweig, BRD at Sep. 8th, 1991 under accession numbers DSM 6714 and DSM 6715 respectively. These specific pDS56/RBSII-plasmids with their specific regulatable promoter/operator elements and ribosomal binding sites can achieve a high level of expression. Therefore, the plasmids can be maintained in E. coli cells only when the activity of the promoter/operator element is repressed by the binding of a lac repressor to the operator. The activity of the promoter can be restored when the culture has reached the desired cell density by addition of isopropyl-β-D-thio-galactopyranoside (IPTG), which inactivates the repressor and clears the promoter. Since most of the E. coli strains do not provide enough repressor molecules to completely repress the function of the promoter sequences present in these high copy number plasmids, such E. coli strains, E. coli M15 or SG13009, have to be first transformed with a plasmid, such as pREP 4, which codes for the lac repressor, before being transformed with the specific pDS56/RBSII-plasmids of the invention which thereafter can be stably maintained in the E. coli cells. In addition to coding for the lac repressor, pREP4 also contains a region of the plasmid pACYC184 [Chang and Cohen, J. Bacteriol. 134, 1141–1156 (1978)], which contains all information required for replication and stable transmission to daughter cells. The DNA sequence of $p^{REP4}$ is set out in FIG. 4A–4C and SEQ ID No: 14 [see also "System for high level production in E. coli and rapid purification of recombinant proteins: application to epitope mapping, preparation of antibodies and structure function analysis" by Stüber et al. in Immunological Methods, Vol. IV, pp 121–152, Lefkovits and Pernis (eds.), Academic Press, New York (1990)].

A preferred embodiment of the present invention is an expression vector suitable for producing a human Tumor Necrosis Factor mutein comprising the amino acid sequence set forth in SEQ ID No: 1 wherein SEQ ID No: 1 is changed by deletion, insertion, substitution or combinations thereof, of at least one amino acid so that the mutein shows a significant difference between its binding affinity to the human p75-(Tumor Necrosis Factor)-Receptor and to human. p55-Tumor Necrosis Factor)-Receptor when the vector is stably transformed or transfected in a prokaryotic or lower eukaryotic host cell.

Another preferred embodiment of the present invention is a vector comprising SEQ. ID No: 2 wherein the DNA sequence comprising positions 115 to 591 is changed by deletion, insertion, substitution or combinations thereof.

Transformation of the host cells by vectors as described above may be carried out by any conventional procedure [see, e.g., Sambrook et al. supra]. Where the host cell is a prokaryote, such as E. coli for example, competent cells which are capable of DNA uptake are prepared from cells harvested after exponential growth, phase and subsequently treated according to the known $CaCl_2$-method. Transformation can also be performed after forming a protoplast of the host cell or by other methods known in the art and described, for example in Sambrook et al. supra. Therefore a vector, especially for expression in a prokaryotic or lower eukaryotic host cell, comprising a DNA-sequence coding for a TNF-mutein as described above, and a host cell, especially a prokaryotic host cell, for example, E. coli, or a lower eukaryotic host cell, transformed by such a vector are also an object of the present invention.

Usually, the host organisms which contain a desired expression vector are grown under conditions which are optimal for their growth. In case of a procaryotic host at the end of the exponential growth, when the increase in cell number per unit time decreases, the expression of the desired TNF-mutein is induced, that is the DNA coding for the desired TNF-mutein is transcribed and the transcribed mRNA is translated. The induction can be carried out by adding an inducer or a derepressor to the growth medium or by altering a physical parameter, for example a change in temperature. In the expression vectors used in the preferred embodiments of the present invention, the expression is controlled by the lac repressor. By adding IPTG, the expression control sequence is derepressed and the synthesis of the desired TNF-mutein is thereby induced.

A preferred embodiment of the present invention is a prokaryotic or lower eukaryotic host cell stably transformed or transfected with a vector suitable for producing a human Tumor Necrosis Factor mutein comprising the amino acid sequence set forth in SEQ ID No: 1 wherein SEQ ID No: 1 is changed by deletion, insertion, substitution or combinations thereof, of at least one amino acid so that the mutein shows a significant difference between its binding affinity to the human p75-(Tumor Necrosis Factor)-Receptor and to human p55-(Tumor Necrosis Factor)-Receptor.

Another preferred embodiment of the present invention is a host cell which is stably transformed or transfected with an expression vector comprising positions 115 to 591 of SEQ ID No: 2 and in which the DNA sequence is changed by deletion, insertion, substitution or combinations thereof, such that the DNA sequence codes for a human Tumor Necrosis Factor mutein containing at least one amino acid different from SEQ ID No: 1.

TNF-muteins of the present invention produced by transformed host cells as stated above can be recovered from the culture medium or after opening the cells with or without extraction by any appropriate method known in protein and peptide chemistry such as, for example, precipitation with ammonium sulfate, dialysis, ultrafiltration, gelfiltration or ion-exchange chromatography, gel electrophoresis, isoelectric focusing, affinity chromatography, like immunoaffinity chromatography, HPLC or the like. Specifically preferred methods are precipitation with ammonium sulfate and/or polyethylenimine, dialysis, affinity chromatography, for example on phenyl-agarose, specifically phenyl-sepharose, or ion-exchange chromatography, specifically on a MONO-Q- and/or MONO-S-matrix (Pharmacia, Uppsata, Sweden) or more specifically preferred are those as described by Tavernier et al. [J. Mol. Biol. 211, 493–501 (1990)] and those disclosed in Example I or Example III.

It is therefore also an object of the present invention to provide a process for the preparation of a compound as specified above which process comprises cultivating a transformed host Cell as described above in a suitable medium and isolating a mutein from the culture supernatant or the host cell itself, and if desired converting said mutein into a pharmaceutically acceptable salt. The compounds whenever prepared according to such a process are also an object of the present invention.

The muteins of the present invention are characterized by showing a significant difference between its binding affinity to the human p75- TNF-R and the human p55-TNF-R. Such property can be determined by any assay known in the art measuring binding affinities. For example, the binding of TNF itself and of the muteins of the present invention can be measured using cells in cell culture which express the two types of TNF-receptors to a different degree, for example Hep-2 cells which exclusivly express the human p55-TNF-R and U937 or HL60 cells which express both the human p55-TNF-R and the human p75-TNF-R [see Brockhaus et al., Procd. Nat. Acad. Sci. U.S.A. 87, 3127–3131, (1990); Hohmann et al., J. Biol. Chem. 264, 14927–14934, (1989); Loetscher et al. (1990); Dembic et al. (1990)]. Of course binding affinities can also be determined directly by using purified native or recombinant p55-TNF-R and p75-TNF-R as specifically described in Example II2, or by using the corresponding soluble analogs of such receptors.

The term "significant difference between its binding affinity to the human p75-Tumor-Necrosis-Factor-Receptor (p75-TNF-R) and to the human p55-Tumor-Necrosis-Factor-Receptor" (p55-TNF-R) refers, in the context of the present invention, to a difference in binding affinities to the two types of TNF-receptors which is with respect to the assay system used, significant enough to say that a mutein of the present invention binds preferentially to one of the two TNF-receptors as compared to wild type TNF. The binding affinity for the p55-TNF-R expressed as a $K_D$-value is measured using Hep-2 cells which only carry that receptor. The binding affinity for the p75-TNF-R is measured using the U937 cells which predominantly, but not exclusively carry the p75 receptor. In terms of the assay system described in Example II (b)(iii)(Table E), the muteins of the present invention differ in their binding affinities to p55-TNF-R and p75-TNF-R by a factor in the range from about 10 to more than 200. A preferential upper limit of this range is 1000 and a most preferential upper limit of this range is 10000. More specifically this term means in the context of the assay-system of Example II (b)(iii) that a $K_D$-value of a specific TNF-mutein of the present invention is at least a factor of 10 or more, especially preferred at least a factor of $10^2$, larger than for TNF-α itself determined by using U937 cells whereby its $K_D$-value determined by using Hep-2 cells for the same TNF-mutein is not larger than a factor of 2 as for TNF-α itself [for specific data see Table E]. It is however understood that these specific $K_D$-values are given for illustration and should not be considered as limiting in any manner. Since the purified receptors bind TNFα in the filter binding assays of the present invention with high affinity (see Schönfeld et al., J. Biol. Chem. 266, 3863–3869), namely for the p75-TNF-R with a $K_D$ of $1.0 \times 10^{-11}$M and for the p55-TNF-R with a $K_D$ of $16 \times 10^{-11}$M the preferential binding of the muteins of the present invention to one of the two TNF-receptors can be also illustrated by a so called selectivity factor "S" which is defined in the following manner:

$$S = \frac{IC50\ p75 - TNF - R}{IC50\ p55 - TNF - R}$$

"IC50 p75-TNF-R" or "IC50 p55-TNF-R" stands for the concentration of a mutein of the present invention which concentration leads to a 50% inhibition of, the binding of TNFα to the p75-TNF-R or p55-TNF-R in a competition assay (such values can be calculated from the data shown in FIG. 1 and FIGS. 10A–10E; see Table F). Accordingly the muteins of the present invention can show an S-value in the range of 10 to at least 500, preferentially 1000 (see Table G). In addition based on the IC50-values the value of decrease of the affinity of the mutein for both receptors can be calculated (see Table F).

The muteins of the present invention can be characterized by their anti-tumour activity by methods known in the art and described for example in Example IV.

The muteins of the present invention may show considerably reduced cytotoxic activity in standard TNFassays which are based on murine cell lines, such as L929 (see Table E) or L-M cell lines.

TNF-muteins of the present invention can be used for the treatment of illnesses, for example cancer.

A further object of the present invention is a pharmaceutical composition and a process for its preparation which composition contains one or more compounds of the invention, if desired in combination with additional pharmaceutically active substances with our without non-toxic, inert, therapeutically compatible carrier materials. For this purpose, one or more compounds of the invention, where desired or required in combination with other pharmaceutically active substances, can be processed in a known manner with the usually used solid or liquid carrier materials. The dosage of such preparations can be effected having regard to the usual criteria in analogy to already used preparations of similar activity and structure.

A preferred embodiment of the present invention is a pharmaceutical composition comprising an effective amount of a human Tumor Necrosis Factor mutein compirsing SEQ ID No: 1 in which SEQ ID No: 1 is changed by deletion, insertion, substitution or combinations thereof, of at least one amine acid so that the mutein shows a significant difference between its binding affinity to the human p75-(Tumor Necrosis Factor)-Receptor and to human-p55-(Tumor Necrosis Factor)-Receptor or a pharmaceutically acceptable salt thereof and an inert carrier.

BRIEF DESCRIPTION OF THE DRAWINGS

FIGS. 4A–4C is the nucleotide sequence of plasmid pREP4.

FIGS. 6A–6C is the nucleotide sequence of plasmid pDS56/RBSII, Sph1-TNFα.

DETAILED DESCRIPTION OF THE INVENTION

After the invention has been described in general hereinbefore, the following Examples are intended to illustrate details of the invention, without thereby limiting it in any manner.

EXAMPLE 1

A. Preparation of Ser$^{29}$-TNFα and Trp$^{32}$-TNFα

(1) Construction of a mutagenesis vector

Figure 5:
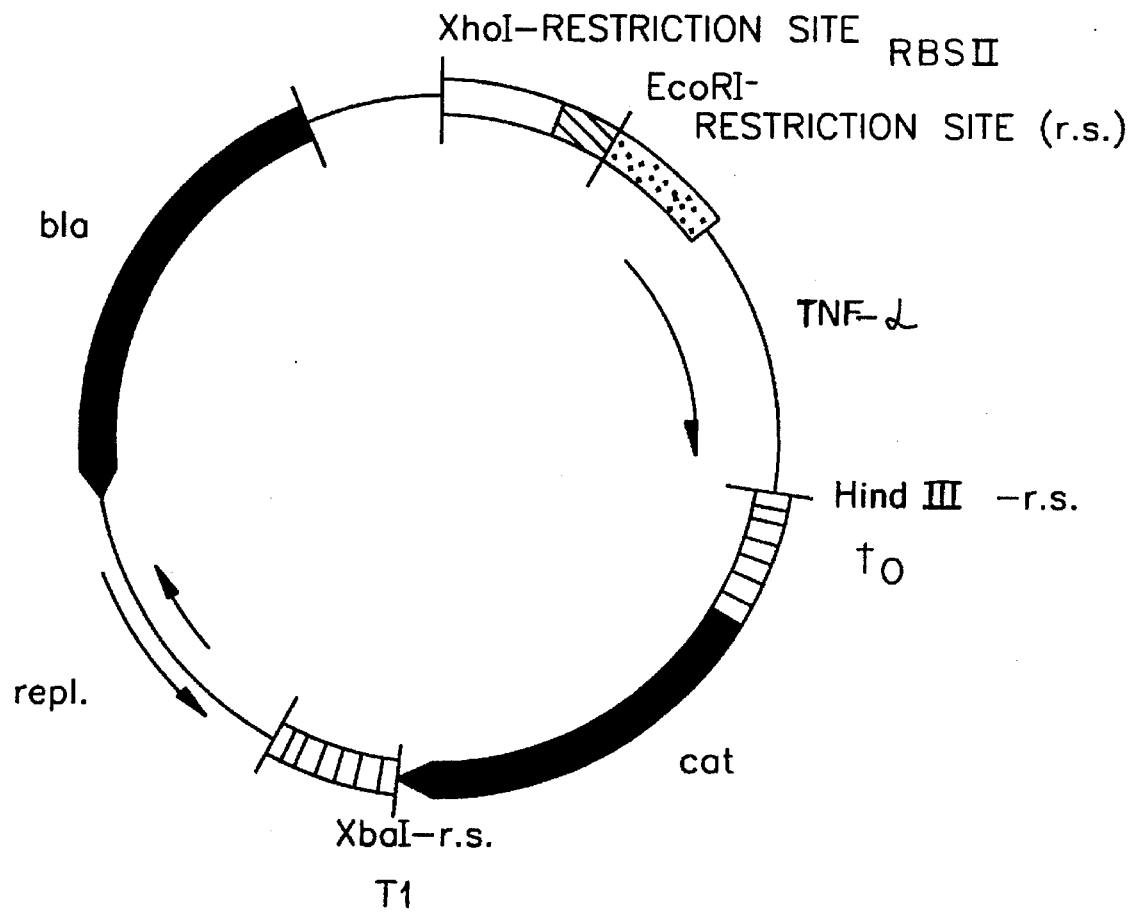
FIG. 5 is a schematic depiction of plasmid pDS56/RBSII, Sph1-TNFα.

From the human TNF expression plasmid pDS56/RBSII, Sph1-TNFα (see FIG. 5: The expression plasmid contain the regulatable promoter/operator element N25OPSN25OP29 (▭▶), the synthetic ribosomal binding site RBSII (▭▶), genes (▭▶) for β-lactamase (bla), chloramphenicol acetyl-transferase (cat), and transcriptional terminators (▭▶) to of phage lambda (t$_o$) and T1 of rrnB operon of *E. coli* (T1), and the replication region of plasmid pBR322 (repl.). The coding region under control of N25OPSN25OP29 and RBSII is indicated by an arrow; for complete nucleotide-sequence of the plasmid see [SEQ ID No: 2] FIGS. 6A–6C given by the one letter standard abreviations for nucleotides), an EcoR1-HindIII fragment was isolated, containing the ribosome binding site RBSII, the mature TNFα coding sequence and a 130 bp 3' non-translated sequence. This fragment was cloned into the EcoR1-HindIII opened pMac phasmids (Stanssens et al., supra); resulting in the constructions pMa/RBSII,Sph1-TNFα and pMc/RBSII,Sph1-TNFα.

(2) Isolation of single-stranded (ss)DNA

The pMa/RBSII,Sph1-TNFα phasmid was transformed to *E. coli* WK6 (Stanssens et al., supra). One colony was picked up and cultured in 5 ml LB medium (Sambrook et al., supra 1989) with carbenicillin (50 µg/ml) at 37° C., overnight. 1 ml of this confluent culture was used to inoculate 200 ml LB containing carbenicillin. When the absorbance (650 nm) reached a value of 0.1, the culture was infected with M13K07 helper phage (Stanssens et al., (1989) at a m.o.i. of about 20 and further incubated overnight at 37° C. Then, the cells were spun down (10 min, 10.000 rpm) and the supernatant was transferred into another tube. 50 ml PEG-solution (20% polyethylene glycol 6000; 2.5M NaCl) was added and the mixture was kept on ice for one hour to precipitate the phages. After centrifugation (10 min; 8000 rpm), the supernatant was removed and the tube was dried on paper towels for 10 min. The phage pellet was resuspended in 6 ml TE buffer (10 mM Tris-HCl, 0.1 mM EDTA, pH8). A first extraction was performed with 6 ml TE-saturated phenol, followed by vortexing for 3 min. After centrifugation. (3 min) in an Eppendorf centrifuge, the aqueous phase was transferred to a fresh tube and a second extraction was carried out with chloroform:isoamylalcohol (24:1) in the same way as described. The single stranded DNA could be precipitated by adding 1/10 volume of 5M NaClO$_4$ and 1 volume of isopropanol (−20° C., 2 hours). This ssDNA was pelleted by centrifugation for 20 min in an Eppendorf centrifuge. The pellet was dried and dissolved in 500 µl TE buffer as a control, 5 µl of this mixture was run on an agarose gel, containing 1 µg/ml ethidium bromide. Usually, the ratio of pMa/RBSII,Sph1-TNFα ssDNA (=(+) strand) over helper phage ssDNA was between 2:1 and 20:1. The amount of total ssDNA was estimated to be at least 200 ng/µl.

(3) Construction of a gap-duplex

From the phasmid pMc, the EcoR1-HindIII large fragment was isolated and used for hybridization to the pMa/RBSII, Sph1-TNFα(+)strand. In a typical experiment, 15 µl ssDNA (±3 µg), 15 µl of the double stranded, linear fragment (±1.5 µg), 10 ml hybridization buffer (1.5M KCl; 100 mM Tris-HCl, p.H 7.5) and 40 µl H$_2$O were mixed and incubated at 100° C. for 4 min, 65° C. for 8 min and room temperature for 15 min. An aliquot (10 ml) was electrophoresed on an agarose gel containing ethidium bromide, to check the formation of gap duplex DNA and, if so, to estimate its quantity (this usually amounted to 50 ng/10 ml hybridization mixture).

(4) Annealing of the mutant oligonucleotide and fill-in of the gap duplex

Oligonucleotides were synthesized. Containing the mutated codon and destroying or creating a restriction site in the TNF gene. The oligonucleotides 5'CCGGCGGTTG-GACCACTGGAGC3' [SEQ ID No: 15] and 5'CATTGGCCCAGCGGTTCAG3'[SEQ ID No: 16] (mutated bases underlined) were used to create the Ser$^{29}$ and Trp$^{32}$ mutations, respectively. After enzymatic phosphorylation, about 8 pmol was added to 40 ng of gap-duplex. H$_2$O was added to a final volume of 10 ml. This mixture was heated to 65° C. for 5 min and allowed to cool to room temperature. Subsequently, 18 ml H$_2$O, 4 µl fill-in buffer 10 (625 mM KCl, 275 mMTris-HCl, 150 mM MgCl$_2$, 20 mM DTT pH 7.5), 2 μl ATP 1 mM, 4 μl of the four dNTP's 1 mM, 1 μl ligase and 1 ml Klenow polymerase were added and the mixture was incubated at room temperature for 45 min.

(5) Transformation to E. coli WK6 mutS and E. coli WK6

We used 10 μl of the filled-in gap duplex DNA to transform (Sambrook et al., 1989) E. coli WK6 mutS (Stanssens et al., supra). From this mixture (1.2 ml), 100 ml was plated out on agar plates containing 25 μg/ml chloramphenicol to check transformation efficiency. The remainder was used to inoculate 20 ml LB+chloramphenicol and further grown overnight at 25° C. A small-scale plasmid DNA preparation [Birnboim, H. C. and Doly, J., Nucleic-Acids Res., 7, 1513, (1979)] of this culture (not yet grown to confluency) resulted in a mixed phasmid population that could be transformed to E. coli WK6. Again, 100 μl transformation mixture was plated out on agar plates containing chloramphenicol.

(6) Screening by colony hybridization

About 100 colonies, resulting from the transformation to E. coli WK6, were streaked on a nylon filter (PALL, Glen Cove, N.Y.) and incubated overnight at 37° C. The filter was transferred (face up) to Whatmann 3 MM papers which were soaked: in 0.5M NaOH (3 min). Neutralization was done by transfer to Whatmann 3 MM sheets soaked in 1M Tris-HCl pH 7.4 (twice for 1 min) and 2XSSC (20×SSC=3M NaCl; 0.3M Na citrate, pH7) (5 min). After drying, the filter was baked at 80° C. between sheets of 3 MM paper. Subsequently, the filter was prewetted in 6×SSC (5 min) and prehybridized at 67° C. for 5 min in 10× Denhardt solution (2% (w/v) Ficoll (400,000 MV), 2% (w/v) Polyvinylpyrrolidone (44,000 MW), 2% (w/v) Bovine Serum Albumin), 6×SSC buffer and 0.2% SDS. After rinsing in 6×SSC buffer, the filter was placed in a Petri dish containing 4 ml 6×SSC and 60 pmol of the $^{32}$P-labeled mutant oligonucleotide for 1 hour at room temperature, and rinsed in 100 ml 6×SSC. The filter was covered with Saran® wrap or suitable plastic film and autoradiographed on preflashed films (Fuji) at –70° C. for 1 hour. Subsequently, the filter was again washed in 6×SSC buffer at increasing temperatures (varying between 51° C. and 75° C., according to the lenght of the probe and its amount of G and C residues), followed each time by an autoradiography, as described above. For instance, a wash at 64° C. could clearly distinguish the Ser$^{29}$ mutants from the wild-type colonies, while the Trp$^{32}$ mutants were detected after two subsequent washes at 62° C. and 63° C., respectively.

(7) Restriction fragment analysis

Because the Ser$^{29}$ mutation created an Ava2 restriction site and Arg$^{32}$ destroyed the Nci1 restriction site, both corresponding endonucleases could be used for restriction fragment analysis to check once again the presence of the mutation. The colonies were picked up and grown to confluency in 5 ml LB medium containing chloramphenicol. From these cultures, plasmid DNA was prepared, digested with the appropriate restriction endonucleases and electrophoresed on agarose gels, according to classical procedures (Sambrook et al., 1989).

(8) Subcloning to a bacterial expression vector

Transfer of the mutated TNF gene to an expression vector was carried out exactly the opposite way as the construction of the mutagenesis vector. The phasmid pMc/RBSII,Sph1-TNFαSer29 or pMc/RBSII,Sph1-TNFαTrp32 was digested with EcoR1-HindIII and the small fragment was inserted into the EcoB1-HindIII opened pDS56/RBSII,Sph1-TNFα vector generating plasmids pDS56/RBSII,Sph1TNFαSer29 and pDS56/RBSII,Sph1-TNFαTrp32 and transformed into E. coli M15 cells already containing plasmid pREP4 [SEQ ID No: 14] (encoding the lac repressor; see FIGS. 3 and 4A–4C for a complete nucleotide sequence of the plasmid given by the one letter standard abreviations for nucleotides) by standard methods. Such cultures of transformed E. coli M15 were grown at 37° C. in LB medium (10 g bacto tryptone, 5 g yeast extract, 5 g NaCl per liter) containing 100 mg/l ampicillin and 25 mg/l kanamycin. At an optical density at 600 nm of about 0.7 to 1.0 units, IPTG was added to a final concentration of 2 mM. After an additional 2.5 to 5 h at 37° C. the cells were harvested by centrifugation and the TNF muteins were purified according to Tavernier et al. [J. Mol. Biol. 211, 493–501, (1990)]. The transformed E. coli strains M15 (pREP4;pDS56/RBSII,Sph1-TNFαSer29) and M15(pREP4;pDS56/RBSII,Sph1-TNFαTrp32) have been deposited under the Budapest Treaty for patent purposes at the Deutsche Sammlung von Mikroorganismen und Zellkulturen GmbH(DSM) in Braunschweig, BRD at Nov. 19th, 1990 under accession numbers DSM 6240 and DSM 6241 respectively.

Example II

A. Characterization of Ser$^{29}$-TNFα and Trp$^{32}$-TNFα

1) Differential binding and biological activity on Hep2-and U937 cells (a) Cell culture Hep-2 [ATCC No. CCL 23], U937 [ATCC No. CRL 1593] and RAJI [ATCC No. CCL 86] cells were grown in RPMI 1640 medium, supplemented with 10% (v/v) inactivated .fetal calf serum, L-glutamine (2 mM), sodium pyruvate (1 mM), 2-mercaptoethanol (5×10$^{-5}$M), 1% of a 100× mixture of non-essential amino acids [Gibro Laboratories, Paisley, GB] and gentamycine (25 mg/ml). The non-adherent cells (U937 and RAJI) were harvested after reaching a density of 1×10$^6$ cells/ml. For binding experiments, the adherent Hep-2 cells were grown to confluency, trypsinized, collected and seeded in large. Petri dishes (150 cm$^2$) at a density of 2.5×10$^6$ cells/ml. Subsequently, the dishes were placed in a CO$_2$-incubator overnight. Because Hep-2 cells are not strongly adherent, the cells could be harvested the same way as the non-adherent cells. Dulbecco's medium, supplemented with 10% inactivated newborn calf serum was used for L929 cell growth.

(b) Determination of the specific activities on L929, Hep-2 and U937 cells.

The amount of protein was determined by the Biorad (Richmond, Calif., USA) protein dye reagent according to the instructions of the manufacturer. The purity of the TNF muteins was determined by SDS-PAGE.

The cytotoxic activity on mouse L929 cells was determined using the standard L929 assay (Ruff and Gifford in "Lymphokines", ed. by E. Pick, Vol. 2, 235–275, Academic Press, 1981, Orlando, USA). The cytotoxicity assay on Hep-2 cells was performed the same way as the L929 assay with the only exception that cycloheximide (50 μg/ml) was added instead of actinomycin D.

(c.) Receptor binding assay (i.) Iodination of TNF-α and Trp$^{32}$-TNF

5 μg Iodogen (Pierce, USA) was dissolved in 10 μl chloroform and dried under a nitrogen stream in a small glass tube. To this, 10 μl Na$^{125}$I (Amersham, 100 mCi/ml in 0.1M borate buffer, pH 8) was added and kept for 15 min. on ice. This solution was quickly pipetted to an Eppendorf tube, containing 5 μg TNF-α [Pennica et al., s.a.] or 3.2 μg of Trp$^{32}$-TNF in 10 μl phosphate buffer pH 7. Again the reaction was kept for 15 min on ice. To separate the iodinated TNF-α from the Na$^{125}$I, a PD-10 gelfiltration column (Pharmacia) was first equilibrated with 0.1M phosphate buffer+0.25% gelatin and prerun with 1 µg TNF-α or Trp$^{32}$-TNF, depending on the iodinated TNF species. Subsequently, the reaction mixture was loaded onto the column, and fractions of about 400 µl were collected from which 2 µl aliquots were counted in a γ-counter (LKB 1275 Minigamma, Pharmacia LKB, Uppsala, Sweden). A specific radioactivity of 10–75 and 80 µCi/mg was obtained for TNF-α and Trp$^{32}$-TNF, respectively.

(ii.) Determination of the $K_D$-value of labeled TNF-α and Trp$^{32}$-TNF by Scatchard analysis A dilution series in multiples of 2 in the range of 12.8 nM to 0.006 nM of the labeled TNF-α or Trp$^{32}$-TNF was made up in a microtiterplate. Each dilution was made in triplicate. Non-specific binding was measured by the same setup, wherein each point contained a 100 fold excess of unlabeled TNF (1.28 µM to 0.6 nM). To each well, approximately 2×10$^6$ cells (U937, Hep-2 or RAJI) were added. The reaction was performed in 0.2 ml tissue culture medium, containing 0.1% NaN$_3$ for 2–3 hours at 4° C. After this, samples were transferred from the microtiterplates to small plastic tubes (Micronic systems), already containing 300 µl phthalate oil (dinonylphthalate 33%, dibutylphthalate 66% (v/v)). The tubes were centrifuged in a microfuge (Eppendorf) for 10 min. to spin down the cells, thereby separating them from the supernatant, using the phthalate oil as a separation medium. After inversion of the tubes, the cell pellet (now on top) could easily be isolated by melting off the top of the tubes with a hot scalpel. The amount of radioactivity, bound on the cells, was measured by counting in a γ-counter. From these data, a Scatchard plot and, subsequently, the dissociation constant $K_D$ was determined using the equilibrium binding type "HOT" in the EBDA/LIGAND programm [Mc.Pherson et al., J. Pharmacol. Methods 14, 213–228, (1985)].

(iii.) Determination of the $K_D$ of mutant TNF [Ser$^{29}$-TNF-α and Trp$^{32}$-TNF-α] by competition analysis The Scatchard data showed that a concentration of 0.4 nM radiolabeled TNF-α was high enough to show a clearly detectable signal and fell within the linear part of the saturation curves. This concentration, however, was also low enough to allow addition up to a 5000 fold excess of cold mutant TNF (2 µM), necessary to perform a competition experiment in which $^{125}$I-wild type TNF is the primary ligand and cold mutant the competitor.

A ten well dilution series of unlabeled mutant TNF (2 mM to 0.004 µM) in concentration steps in multiples of 2 was set up in a microtiterplate. The two remaining wells contained no unlabeled TNF (total binding) and a 5000 fold excess of the wild-type, unlabeled TNF (background), respectively. To all wells, 0.4 nM of radiolabeled TNF-α (10–75 µCi/µg) was added. After addition of 2×10$^6$ cells, the total volume was 0.2 ml/well. The medium of incubation, reaction conditions and isolation of the cells were exactly the same as described above for the Scatchard analysis experiments. Each point was measured in triplicate and the dissociation experiments were done twice, the average of the two $K_D$'s being indicated in Table E. Using the "DRUG" method of the EBDA/LIGAND program, competition curves were plotted and the $K_D$ of the muteins was calculated. The following experimental data were used for such calculations:

1. Labeling of hTNF
   first labeling (=batch 1):     1.2 × 10$^8$ dpm/5 µg
       = 3.7 × 10$^5$ dpm/pmol
       = ±10 µCi/µg
   second labeling (=batch:2)     5.3 × 10$^8$ dpm/3.2 µg
       = 1.9 × 10$^6$ dpm/pmol
       = ±75 µCi/µg
2. Determination of the $K_D$ of wild-type TNF
   We measured the $K_D$ of $^{125}$I-TNF (batch 1) on Hep-2 and U937 cells by Scatchard analysis.
   Hep-2: $K_D$ = 9.17 × 10$^{-10}$
   U937: $K_D$ = 2.5 × 10$^{-10}$
3. Competition experiments All displacement experiments were carried out, using $^{125}$I-TNF (batch 1) as the primary ligand, except experiment B.3 (table B, 3.), where $^{125}$I-TNF (batch 2) was used.

In each experiment, the binding at each concentration was measured in triplicate and only the averages are shown in the following tables (A–D).

From each experiment shown in these tables, the $K_D$ value was calculated using the programm of Mc. Pherson et al. (1985). The average of the $K_D$ determinations (2 experiments for Ser$^{29}$-TNFα on Hep-2 cells and on U937 cells, two experiments for Trp$^{32}$-TNFα on Hep-2 cells and three on U937 cells) are shown in table E.

TABLE A

Competition with Ser$^{29}$-TNFα on U937 cells.

|   | Mean dpm | concentration of mutant [mol] |
|---|---|---|
| 1. | 2120 | 0 |
|    | 1869 | 1 × 10$^{-9}$ |
|    | 1779 | 2 × 10$^{-9}$ |
|    | 1719 | 4 × 10$^{-9}$ |
|    | 1708 | 8 × 10$^{-9}$ |
|    | 1575 | 1.6 × 10$^{-8}$ |
|    | 1415 | 3.2 × 10$^{-8}$ |
|    | 1320 | 6.4 × 10$^{-8}$ |
|    | 1200 | 1.25 × 10$^{-7}$ |
|    | 983  | 2.5 × 10$^{-7}$ |
|    | 949  | 5 × 10$^{-7}$ |
|    | 632  | 1 × 10$^{-6}$ |
|    | 533  | 2 × 10$^{-6}$ |
| Background: | 299 |  |
| 2. | 1014 | 0 |
|    | 635  | 4 × 10$^{-9}$ |
|    | 603  | 8 × 10$^{-9}$ |
|    | 541  | 1.5 × 10$^{-8}$ |
|    | 572  | 3 × 10$^{-8}$ |
|    | 489  | 6 × 10$^{-8}$ |
|    | 413  | 1.2 × 10$^{-7}$ |
|    | 380  | 2.5 × 10$^{-7}$ |
|    | 319  | 5 × 10$^{-7}$ |
|    | 263  | 1 × 10$^{-6}$ |
|    | 238  | 2 × 10$^{-6}$ |
| Background: | 205 |  |

TABLE B

Competition with Trp$^{32}$-TNF-α on U937 cells

| 1. | 2120 | 0 |
|---|---|---|
|    | 1917 | 1 × 10$^{-9}$ |
|    | 1698 | 2 × 10$^{-9}$ |
|    | 1655 | 4 × 10$^{-9}$ |
|    | 1585 | 8 × 10$^{-9}$ |
|    | 1488 | 1.5 × 10$^{-8}$ |
|    | 1377 | 3 × 10$^{-8}$ |
|    | 1333 | 6 × 10$^{-8}$ |
|    | 1166 | 1.25 × 10$^{-7}$ |

TABLE B-continued

Competition with Trp$^{32}$-TNF-α on U937 cells

| | | |
|---|---|---|
| | 1026 | $2.5 \times 10^{-7}$ |
| | 953 | $5 \times 10^{-7}$ |
| | 777 | $1 \times 10^{-6}$ |
| | 628 | $2 \times 10^{-6}$ |
| Background: | 299 | |
| 2. | 1047 | 0 |
| | 653 | $4 \times 10^{9}$ |
| | 629 | $8 \times 10^{-9}$ |
| | 636 | $1.5 \times 10^{-8}$ |
| | 585 | $3 \times 10^{-8}$ |
| | 546 | $6 \times 10^{-8}$ |
| | 508 | $1.2 \times 10^{-7}$ |
| | 479 | $2.5 \times 10^{-7}$ |
| | 422 | $5 \times 10^{-7}$ |
| | 357 | $1.10^{-6}$ |
| | 294 | $2 \times 10^{-6}$ |
| Background: | 214 | |
| 3. | 8340 | 0 |
| (carried. out | 4759 | $4 \times 10^{-9}$ |
| with $^{125}$I- | 4041 | $8 \times 10^{-9}$ |
| TNF, batch 2) | 3620 | $1.5 \times 10^{-8}$ |
| | 3275 | $3 \times 10^{-8}$ |
| | 3034 | $6 \times 10^{-8}$ |
| | 2387 | $1.25 \times 10^{-7}$ |
| | 1981 | $2.5 \times 10^{-7}$ |
| | 1472 | $5 \times 10^{-7}$ |
| | 1192 | $1 \times 10^{-6}$ |
| | 814 | $2 \times 10^{-6}$ |
| Background: | 307 | |

TABLE C

Competition with Ser$^{29}$-TNF-α on Hep-2 cells

| | | |
|---|---|---|
| 1. | 938 | 0 |
| | 799 | $1 \times 10^{-9}$ |
| | 677 | $2 \times 10^{-9}$ |
| | 564 | $4 \times 10^{-9}$ |
| | 510 | $8 \times 10^{-9}$ |
| | 451 | $1.6 \times 10^{-8}$ |
| | 442 | $3.2 \times 10^{-8}$ |
| | 446 | $6.4 \times 10^{-8}$ |
| | 379 | $1.25 \times 10^{-7}$ |
| | 374 | $2.5 \times 10^{-7}$ |
| | 437 | $5 \times 10^{-7}$ |
| | 359 | $1 \times 10^{-6}$ |
| | 383 | $2 \times 10^{-6}$ |
| Background: | 353 | |
| 2. | 457 | 0 |
| | 273 | $4 \times 10^{-9}$ |
| | 240 | $8 \times 10^{-9}$ |
| | 253 | $1.5 \times 10^{-8}$ |
| | 235 | $3 \times 10^{-8}$ |
| | 207 | $6 \times 10^{-8}$ |
| | 239 | $1.2 \times 10^{-7}$ |
| | 215 | $2.5 \times 10^{-7}$ |
| | 211 | $5 \times 10^{-7}$ |
| | 193 | $1 \times 10^{-6}$ |
| | 238 | $2 \times 10^{-6}$ |
| Background: | 215 | |

TABLE D

Competition with Trp$^{32}$-TNF-α on Hep-2 cells

| | | |
|---|---|---|
| 1. | 938 | 0 |
| | 742 | $1 \times 10^{-9}$ |
| | 608 | $2 \times 10^{-9}$ |
| | 537 | $4 \times 10^{-9}$ |
| | 547 | $8 \times 10^{-9}$ |
| | 397 | $1.6 \times 10^{-8}$ |
| | 394 | $3.2 \times 10^{-8}$ |

TABLE D-continued

Competition with Trp$^{32}$-TNF-α on Hep-2 cells

| | | |
|---|---|---|
| | 405 | $6.4 \times 10^{-8}$ |
| | 395 | $1.25 \times 10^{-7}$ |
| | 388 | $2.5 \times 10^{-7}$ |
| | 379 | $5 \times 10^{-7}$ |
| | 353 | $1 \times 10^{-6}$ |
| | 386 | $2 \times 10^{-6}$ |
| Background: | 353 | |
| 2. | 445 | 0 |
| | 298 | $4 \times 10^{-9}$ |
| | 222 | $8 \times 10^{-9}$ |
| | 256 | $1.5 \times 10^{-8}$ |
| | 202 | $3 \times 10^{-8}$ |
| | 227 | $6 \times 10^{-8}$ |
| | 210 | $1.2 \times 10^{-7}$ |
| | 221 | $2.5 \times 10^{-7}$ |
| | 197 | $5 \times 10^{-7}$ |
| | 231 | $1 \times 10^{-6}$ |
| | 202 | $2 \times 10^{-6}$ |
| Background: | 203 | |

TABLE E

| | Hep-2 | | L929 | |
|---|---|---|---|---|
| | affinity ($K_D$) | specific activity (U/mg) | U937 affinity ($K_D$) | specific activity (U/mg) |
| TNF-α | $9.17 \times 10^{-10}$(*) (100%) | $2.9 \times 10^{7}$ (100%) | $2.5 \times 10^{-10}$(*) (100%) | $2 \times 10^{7}$ (100%) |
| Ser$^{29}$-TNF-α | $1.06 \times 10^{-9}$ (86.5%) | $9.3 \times 10^{6}$ (32%) | $5.07 \times 10^{-8}$ (0.49%) | $10^{5}$ (0.5%) |
| Trp$^{32}$-TNF-α | $1.06 \times 10^{-9}$ (86.5%) | $4.5 \times 10^{7}$ (155%) | $3.53 \times 10^{-8}$ (0.71%) | $6.4 \times 10^{4}$ (0.32%) |

$K_D$ values indicated by an asterisk (*) were obtained by Scatchard analysis. All other $K_D$ values were determined by competition analysis. Relative values (in percentage to TNF-α) are indicated between brackets.

It can be seen that the binding constant ($K_D$) of Ser$^{29}$-TNF-α and Trp$^{32}$-TNF-α determined with Hep-2 cells (which only carry the p55-TNF-R) are almost the same as TNF-α. Also the biological activity (specific activity) on these cells is largely retained (note that the accuracy, of this assay is only a factor of 3). Strikingly, the binding affinity (measured in the competition assay) of Ser$^{29}$-TNF-α and Trp$^{32}$-TNF-α to the U937 cells, which predominantly but not exclusively, carry the high affinity receptor p75-TNF-R, has been largely lost (increase in $K_D$-value by a factor of more than 100). Thus, the binding affinity of the Ser$^{29}$-TNF-α for p75-TNF-R has been reduced approximately 50 fold to about 2% of its binding affinity to p55-TNF-R. The binding affinity of Trp$^{32}$-TNF-α for p75-TNF-R has been reduced approximately 33 fold to about 3% of its binding affinity to p55-TNF-R. It may also be noted that the biological activity of Ser$^{29}$-TNF-α and Trp$^{32}$-TNF-α, determined in the standard assay based on L929-cells, has been largely lost (decrease by a factor more than 100).

2) Differential binding to the human p75-TNF-R and the human p55-TNF-R

Figure 1:
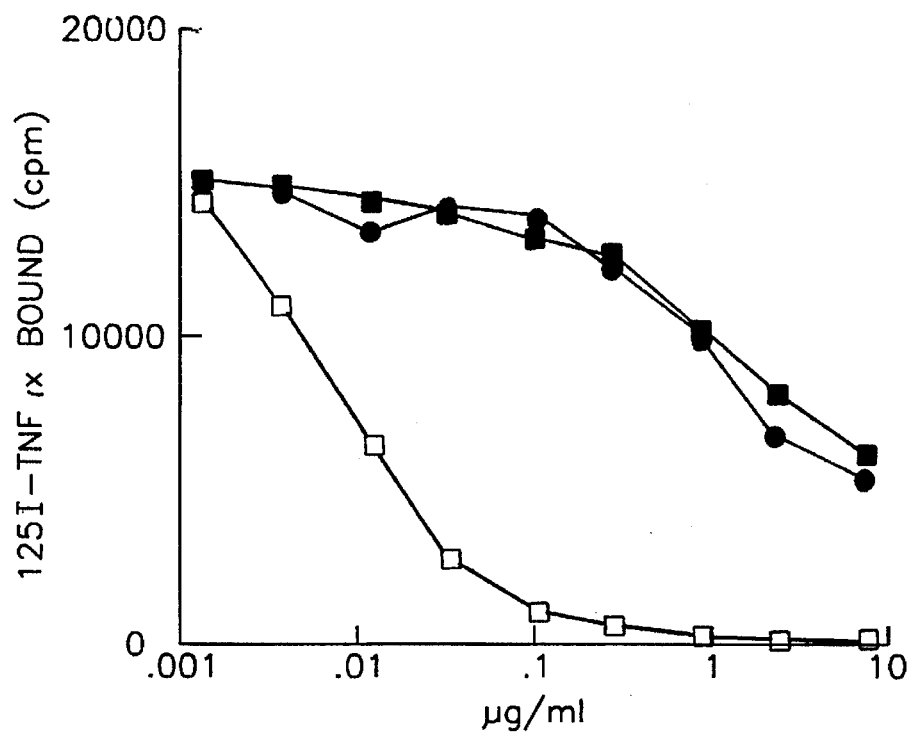
FIG. 1 is a graph showing the results of a competitive binding assay between $^{125}$I-TNF and Trp$^{32}$-TNF, Ser$^{29}$-TNF and wild type-TNF for the p75 receptor.
Figure 2:
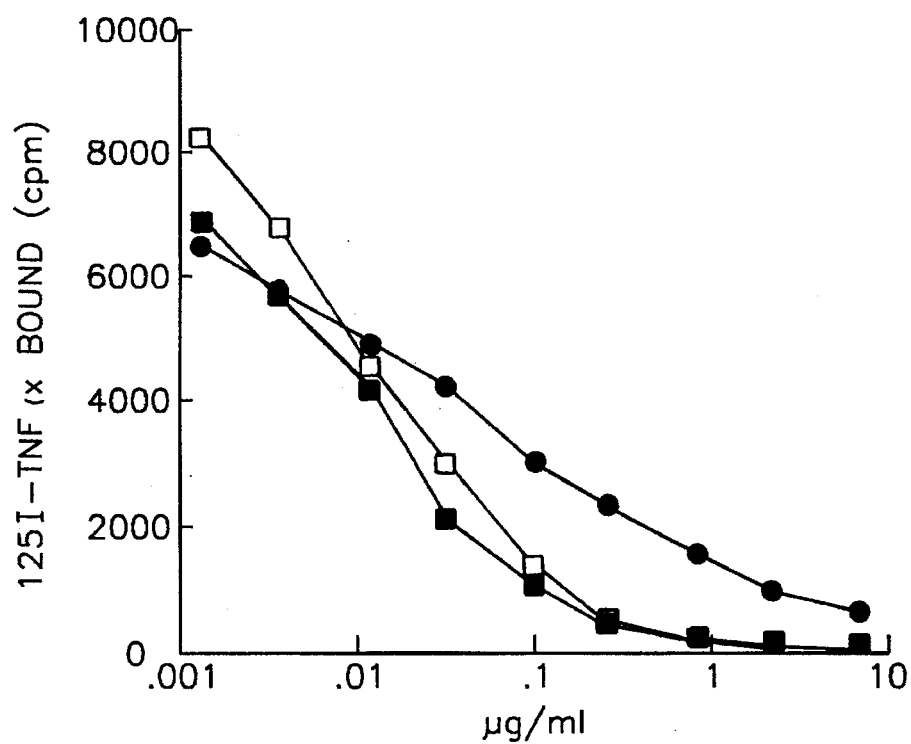
FIG. 2 is a graph showing the results of a competitive binding assay between $^{125}$I-TNF and Trp$^{32}$-TNF, Ser$^{29}$-TNF and wild type-TNF for the p55 receptor.
Figure 3:
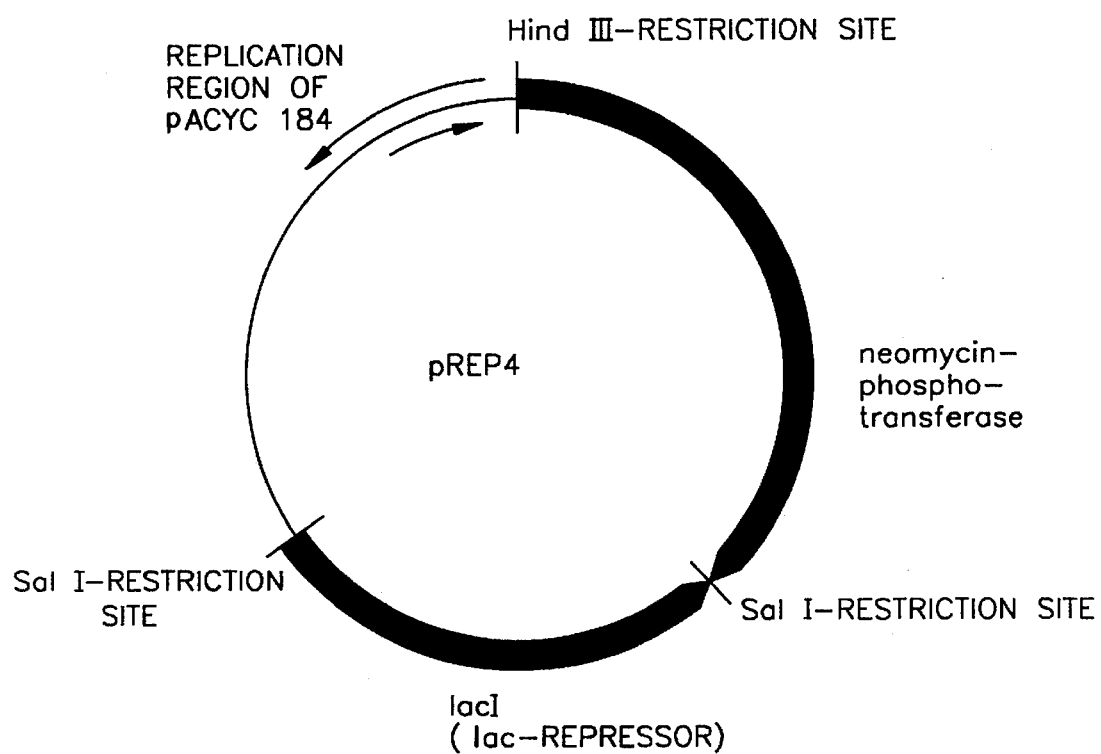
FIG. 3 is a schematic depiction of plasmid pREP4.

Competition of human $^{125}$I-TNF-α binding by Trp$^{32}$- and Ser$^{29}$-TNF-α and human TNF-α to TNF-receptors purified from HL60 cells was determined as follows. 2 μl aliquots of the native p55-TNF-R and the p75-TNF-R purified as described in European Patent Application No. 90116707.2 dissolved at a concentration of about 0.3 μg/ml in 20 mM Hepes, 50 mM Tris, 50 mM NaCl, 1 mM EDTA, 0.1% octylglucoside, 0.1 mg/ml BSA, pH 8.0, were spotted onto prewetted nitrocellulose filters in triplicate. The filters were blocked with blocking buffer (50 mM Tris, 140 mM NaCl, 5 mM EDTA, 0.02% $NaN_3$, 1% defatted milk powder) for 1.5 hours at room temperature. After washing with PBS the filters were incubated with 10 ng/ml $^{125}$I-TNFα and varying concentrations of $Trp^{32}$- or $Ser^{29}$-TNFα, or TNFα overnight at 4° C. The filters were washed with blocking buffer (2× for 5 min.) and with $H_2O$ (1× for 5 min.), air dried, and counted in a γ-counter. Results are given in FIGS. 1 and 2, whereby FIG. 1 shows binding of TNFα (open rectangle), $Ser^{29}$-TNFα (filled circles) and $Trp^{32}$-TNFα (filled rectangle) to human p75TNF-R in case of FIG. 2 to human p75-TNF-R and in case of FIG. 2 to human p55-TNF-R. Based on the data shown in FIG. 1 and in addition those of FIGS. 10A–10E the IC50-values were calculated and are listed for $Ser^{29}$- and $Trp^{32}$-TNFα in Table F. Values for the decrease in affinity for these muteins on both receptors with respect to TNFα are also given in Table F. Values for "S", the selectivity factor, based on IC50 values given in Table F and calculated from FIGS. 10A–10E are shown in Table G.

TABLE F

| Receptor | Competitor | IC50 µg/ml | Decrease in Affinity -fold |
| --- | --- | --- | --- |
| p75-TNF-R | TNFα | 0.010 | — |
|  | $Ser^{29}$-TNFα | 2.5 | 250 |
|  | $Trp^{32}$-TNFα | 5 | 500 |
| p55-TNF-R | TNFα | 0.011 | — |
|  | $Ser^{29}$-TNFα | 0.09 | 8.2 |
|  | $Trp^{32}$-TNFα | 0.017 | 1.5 |

TABLE G

| Mutein | $S = \frac{IC50\ p75\text{-}TNF\text{-}R}{IC50\ p55\text{-}TNF\text{-}R}$ |
| --- | --- |
| TNFα | 1 |
| $Ser^{29}$—TNFα | 28 |
| $Trp^{32}$—TNFα | 294 |
| $Gly^{29}$—TNFα | 80 |
| $Tyr^{29}$—TNFα | 110 |
| $Tyr^{32}$—TNFα | 90 |
| $Ser^{29}$—$Trp^{32}$—TNFα | 450 |

EXAMPLE III

Purification of $Trp^{32}$-TNFα

Transformed cells obtained according to Example I were processed in the following manner:

a) Opening by French press, addition of polyethyleneimine until a final concentration of 0.4%, pH 7.6; and removal of precipitate.

b) Ammonium sulphate precipitation at pH 7.2; fraction 30–70% c) Dialysis against 25% ammonium sulphate in 1.0 mM Tris, pH 6.8 d) Phenyl-Sepharose column CL-4B (35×250 mm)
Load in 25% ammonium sulphate—10 mM Tris, pH 6.8
Elution: gradient 25% ammonium sulphate-Tris buffer to 20 mM ethanolamine, pH 9 (2 times 150 ml).

e) Column Mono Q (HR 16/10).
Load: in 20 mM ethanolamine, pH 9. Elution: gradient (2 times 300 ml) in the same buffer, from 0 to 1M sodium chloride (Pharmacia, FPLC). Active fractions dialysed versus 0.01M phosphate buffer pH 7 f) Column of Heparin Sepharose CL-6B (30×80 mm)
Load in 0.01M phosphate buffer pH 7. Elute with a gradient in the same buffer from 0 to 1M sodium chloride g) Active fractions were concentrated on Amicon (microultrafiltration system 8 MC; membrane Ø 25 mm; diaflo 10 YM10–25 mm) and separately loaded on a gelfiltration column (Ultrapac TSK G-2000 SWG; 21.5×600 mm), equilibrated in 0.01M phosphate pH 7 and 0.9% sodium chloride LPS (determined by test kit of Kabivitrum):
Most active fraction contained 5 mg/ml $Trp^{32}$-TNFα; endotoxin content: 26 E.U./mg
The last active fraction contained 1.8 mg/ml TNF and 47 E.U./mg protein.

EXAMPLE IV

Figure 7:
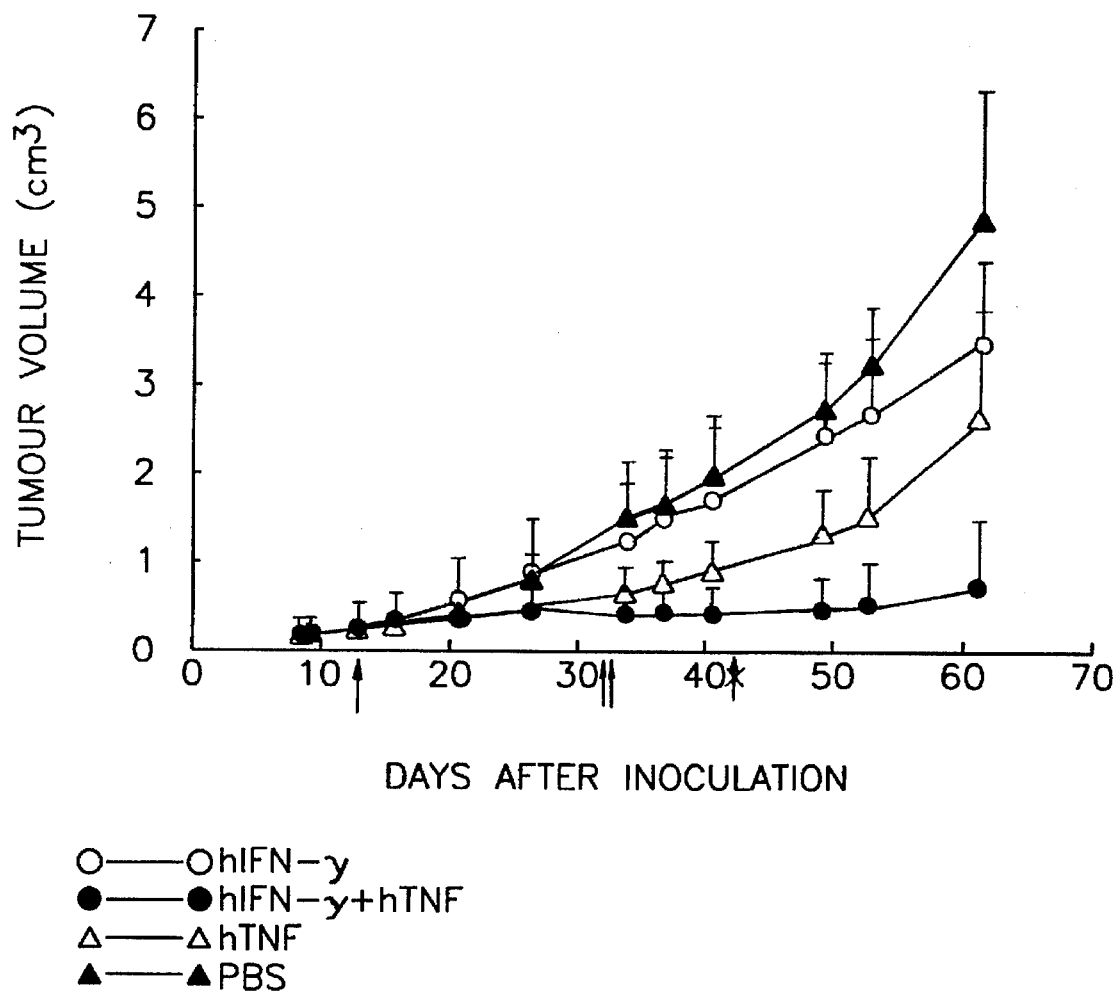
FIG. 7 is a graph showing the results of an assay measuring the antitumor effect of interferon-gamma and TNF, alone or in combination.

1. Anti-tumour effect of hTNFα and hIFNγ on subcutaneous HT-29 tumours in nude mice, $5\times10^6$ HT-29 human colon adenocarcinoma cells [ATCC HTB38] were subcutaneously injected in nude mice. Groups consisted of 5 mice. The treatment comprises daily perilesional injections during 6 days per week, followed by 1 day without treatment. Results are given in FIG. 7 whereby "PBS" refers to phosphate buffered saline as known in the art. The single arrow indicates the start of the treatment with 5 µg hTNFα or 5000 IU human Interferon γ (hIFNγ) or both. The double arrow indicates the time that these doses were doubled and the crossed arrow indicates the end of the treatment.

2. Comparison of the anti-tumour potential of hTNFα and $Trp^{32}$- TNFα

Figure 8:
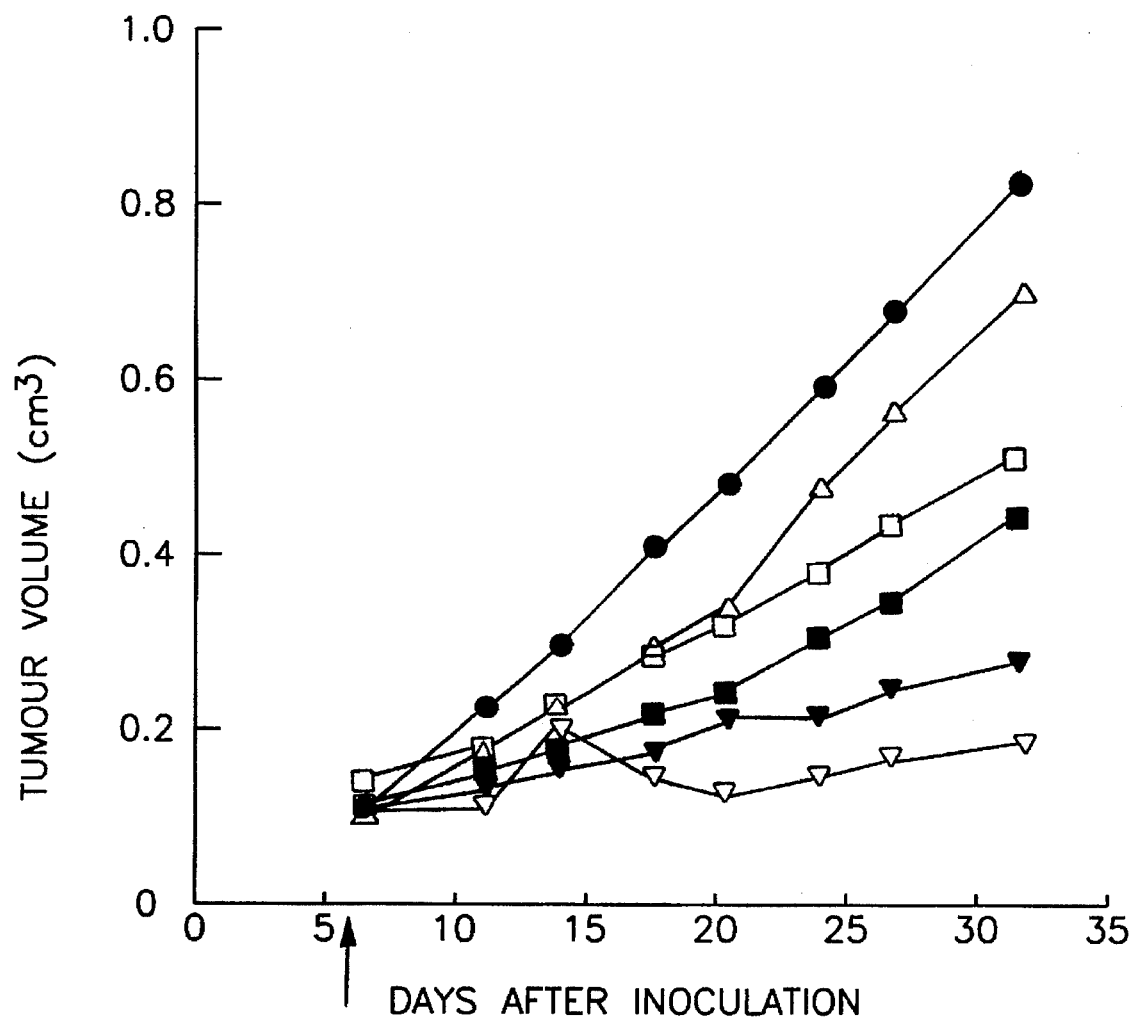
FIG. 8 is a graph showing the results of an assay measuring the antitumor effect of interferon-gamma and TNF, alone or in combination and Trp$^{32}$-TNF alone or in combination with interferon-gamma.
Figure 9A:
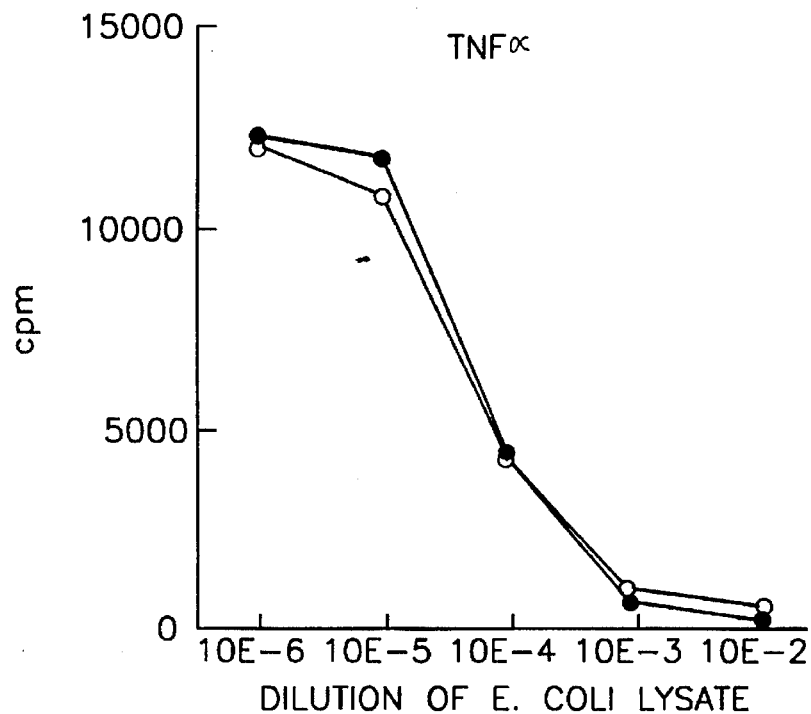
FIGS. 9A–9F is a series of graphs showing the results of a competitive binding assay between $^{125}$I-TNF and various muteins for the p75 receptor and the p55 receptor.
Figure 9B:
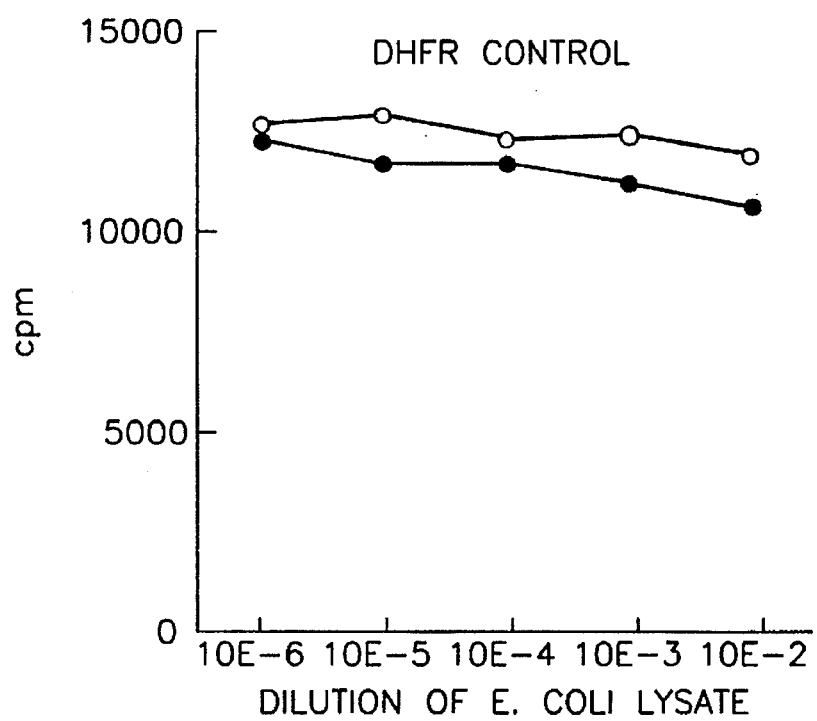
Figure 9C:
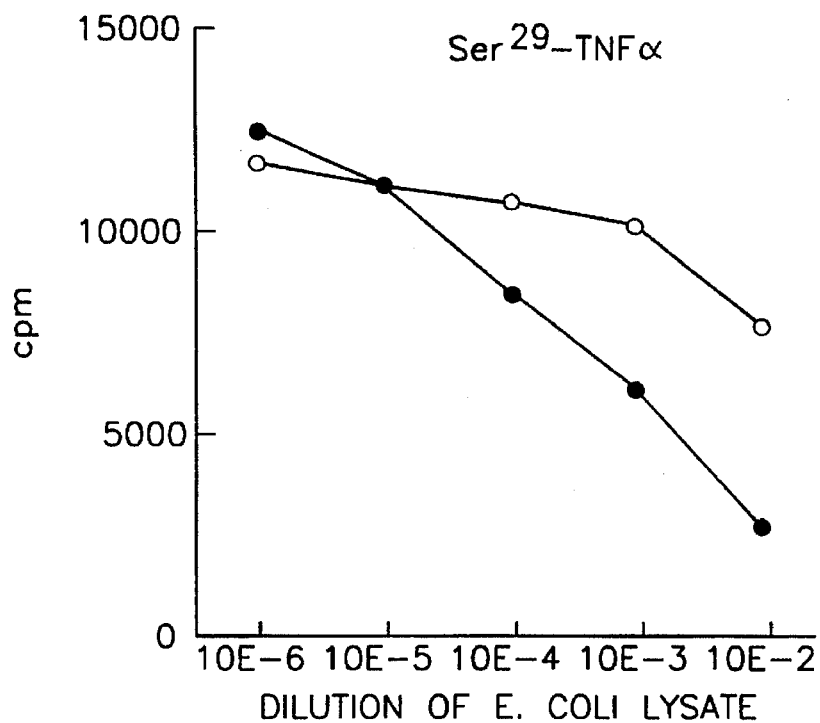
Figure 9D:
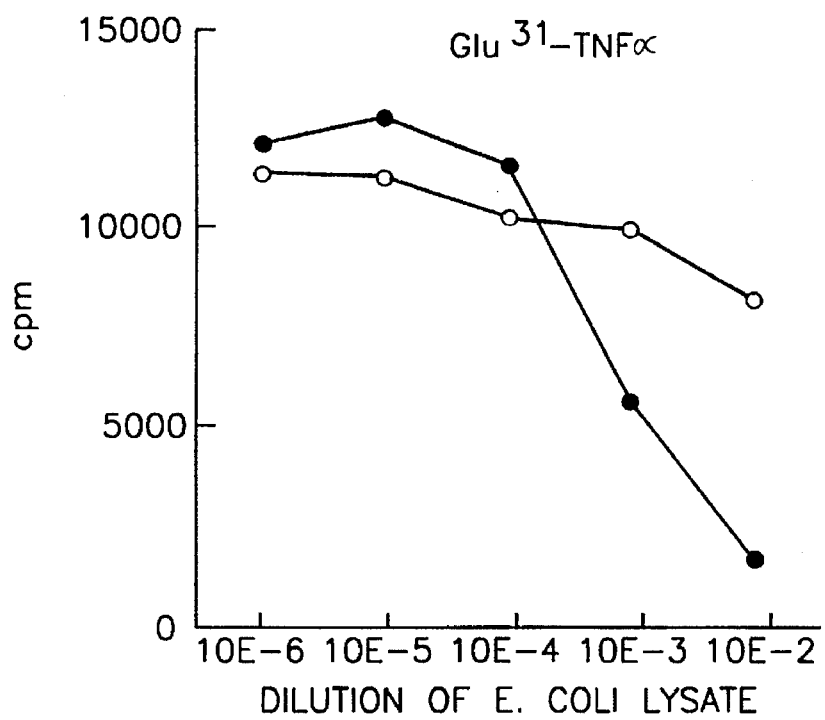
Figure 9E:
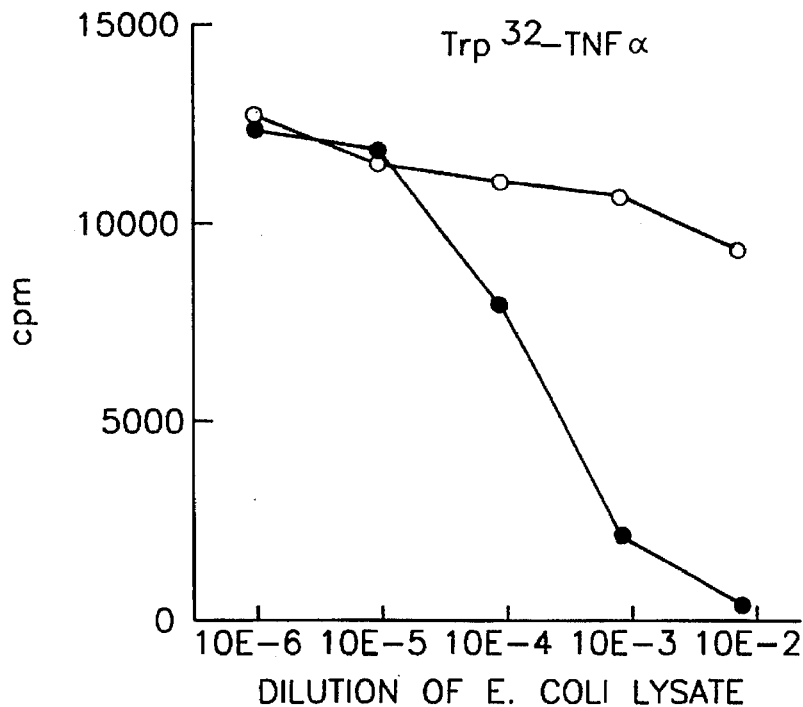
Figure 9F:
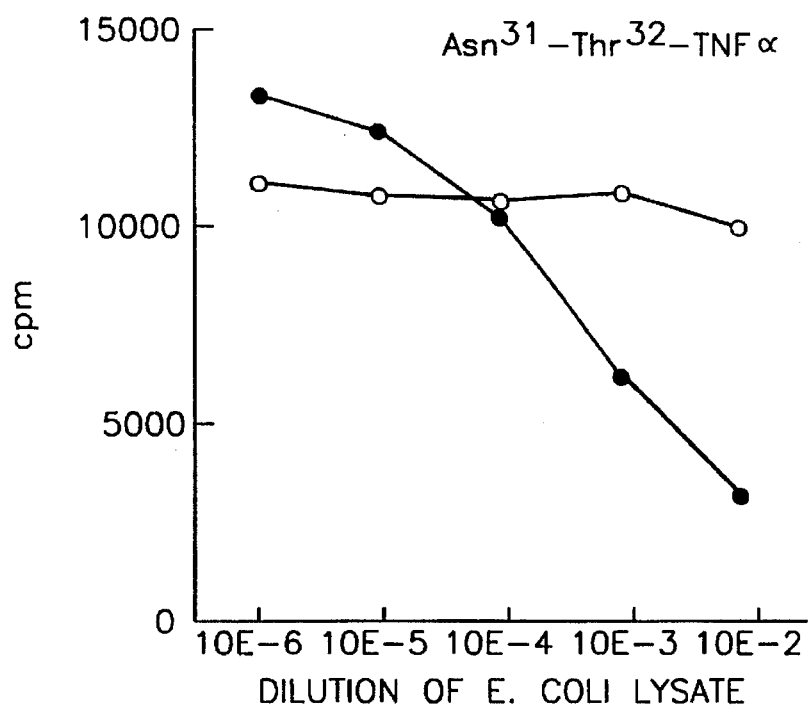
Figure 10A:
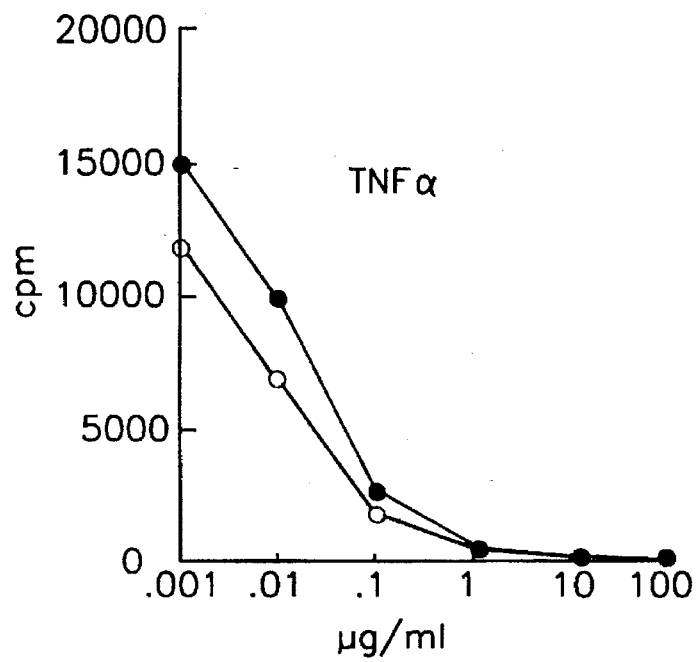
FIGS. 10A–10E is a series of graphs showing the results of a competitive binding assay between $^{125}$I-TNF and various muteins for the p75 receptor and the p55 receptor.
Figure 10B:
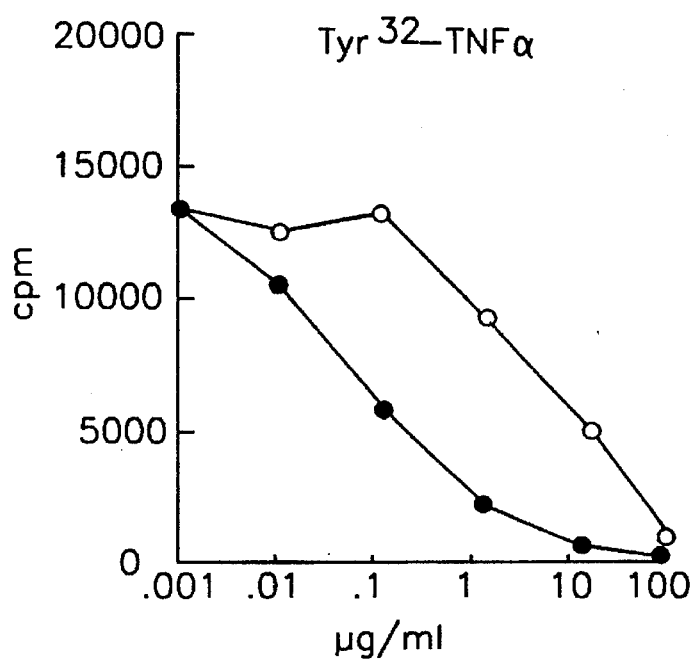
Figure 10C:
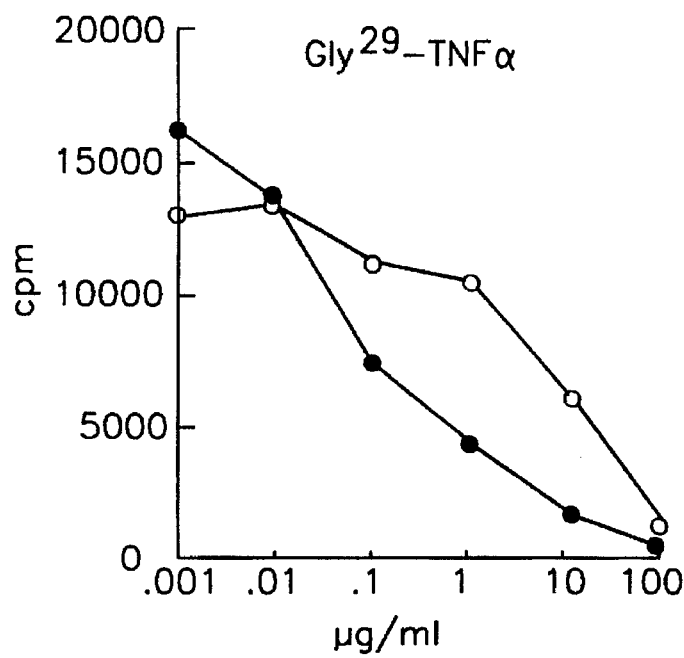
Figure 10D:
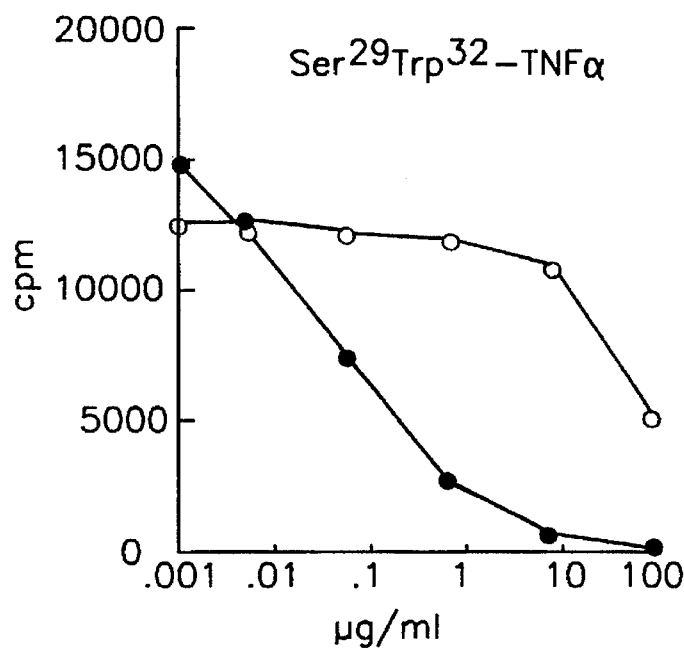
Figure 10E:
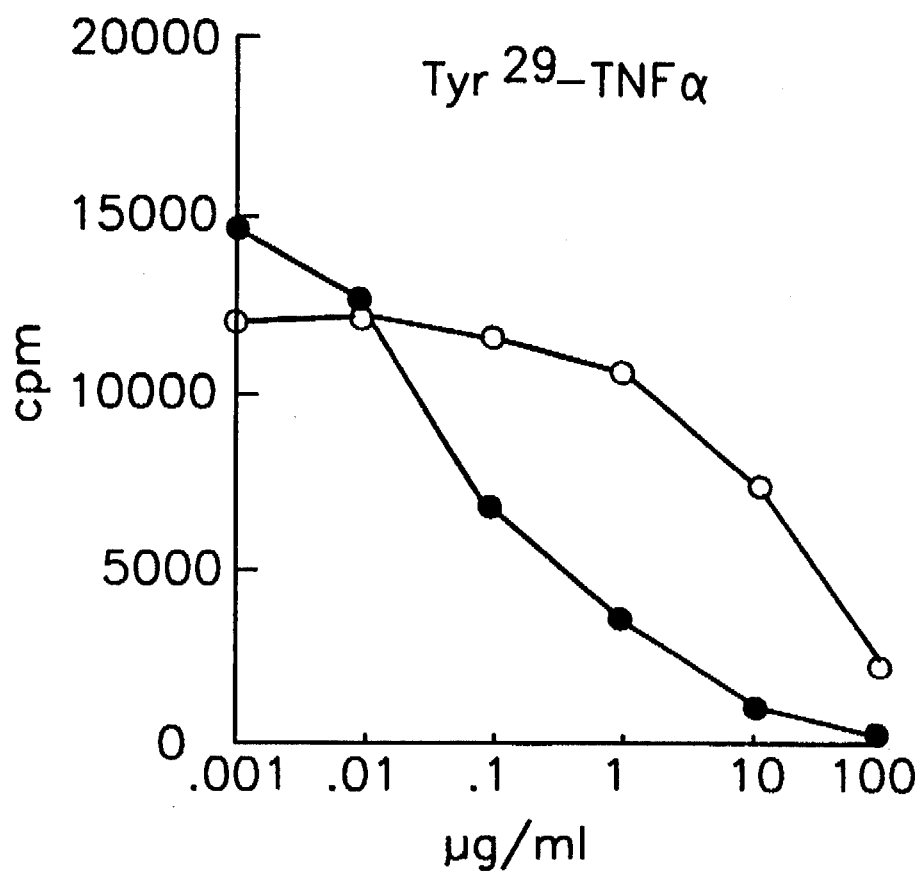

$5\times10^6$ HT-29 human colon adenocarcinoma cells were subcutaneously injected in nude mice. Groups consisted of 5 mice. The treatment started on day 6 following inoculation and comprises daily perilesional injections during 6 days per week. Tumour volume was estimated every 3 or 4 days by measuring the larger (a) and the smaller (b) diameter and calculating the $a\times b^2\times 0.4$ according to Attia and Weiss as known in the art. Results are given in FIG. 8 whereby the arrow indicates the start of the treatment and open triangles with tip down refers to $10^4$ IU of hIFNγ and 10 µg hTNFα, filled triangles with tip down refer to $10^4$ IU of hIFN-γ and 10 µg $Trp^{32}$-TNF, filled rectangles refer to 10 µg $Trp^{32}$-TNFα, open reactangles refer to 10 µg hTNFα, open triangles refer to phosphate buffered saline and filled circles refer to $10^4$ IU of hIFNγ. In vitro, there is no difference in cytotoxicity for Hep or HT-29 cells between hTNFα and $Trp^{32}$-TNFα.

EXAMPLE V

Preparation of $Ser^{29}$-$Trp^{32}$-TNFα

$Ser^{29}$-$Trp^{32}$-TNFα was prepared as described in Example I with the following exceptions:

1. The oligonucleotide used, contains the following sequence [SEQ ID No: 17] (mutated bases underlined):
5'GGGCATTGGCCCAGCGGTTFGGAC-CACTGGAGC3'

2. An Nci 1 site was destroyed while an Ava 2-site was created, allowing for check of the presence of the mutation by restriction fragment analysis. No hybridization analysis was performed. 6 clones resulting from the WK6 transformation were grown up and DNA was prepared and analysed as described in Example I, 3 of the 6 clones contained the mutation.

This DNA sequence was subcloned into the pDS56 expression vector, generating the plasmid pDS56/RBSII, Sph1-TNFαSer29Trp32, and transformed to the E. coli M15 strain. Expression and purification was performed as described in Example I.

EXAMPLE VI

Preparation of Gly$^{29}$-TNFα,Tyr$^{29}$-TNFα and Tyr$^{32}$-TNFα

Gly$^{29}$-TNFα,Tyr$^{29}$-TNFα and Tyr$^{32}$-TNFα were prepared as described in Example I with the following exception. Oligonucleotides were used, containing a fully degenerated codon at position 29 or 32, resulting in a random insertion of all twenty amino acids at one of the two positions. The sequence of these oligonucleotides are as follows:

Position 29 [SEQ ID No: 18]
5' CCACGCCATTCGCGAGGAGGGCATTGGCCCGGCGGTTNNNCCACTGGAGC 3'

Position 32 [SEQ ID No: 19]:
5' CCACGCCATTCGCGAGGAGGGCATTGGCNNNGCGGTTCAGCC 3' where N=A, C, G or T and mutated bases are underlined.

Together with the mutation, also a unique Nru-1 site is introduced. Thus, instead of directly transforming the phasmid-pool, isolated from the WK6 mutS strain, this DNA was first digested with Nru-1, the linear band eluted from the agarose gel, ligated and transformed to the SURE-strain (Stratagene, La Jolla, Calif., USA). In this way, one can select only for phasmids, containing the mutations. 168 colonies obtained were inoculated in microtiterplates, grown to confluency and their lysates tested for biological activity towards Hep-2 cells in a manner as described in Example IIa and for differential binding as described in Example IIb or Example VIII. On the basis of the biological activity on the one side and differential binding as determined according to Example IIb or Example VIII colonies were selected and further characterized by DNA sequence analysis of corresponding inserts as known in the art. DNA-sequences coding for Gly$^{29}$-TNFα, Tyr$^{29}$-TNFα and Tyr$^{32}$-TNFα were isolated from corresponding colonies and cloned in bacterial expression vectors as described in Example I. Muteins expressed were purified to more than 95% homogeneity by means of a MONO-Q ion exchange chromatography step.

EXAMPLE VII

Figure 11:
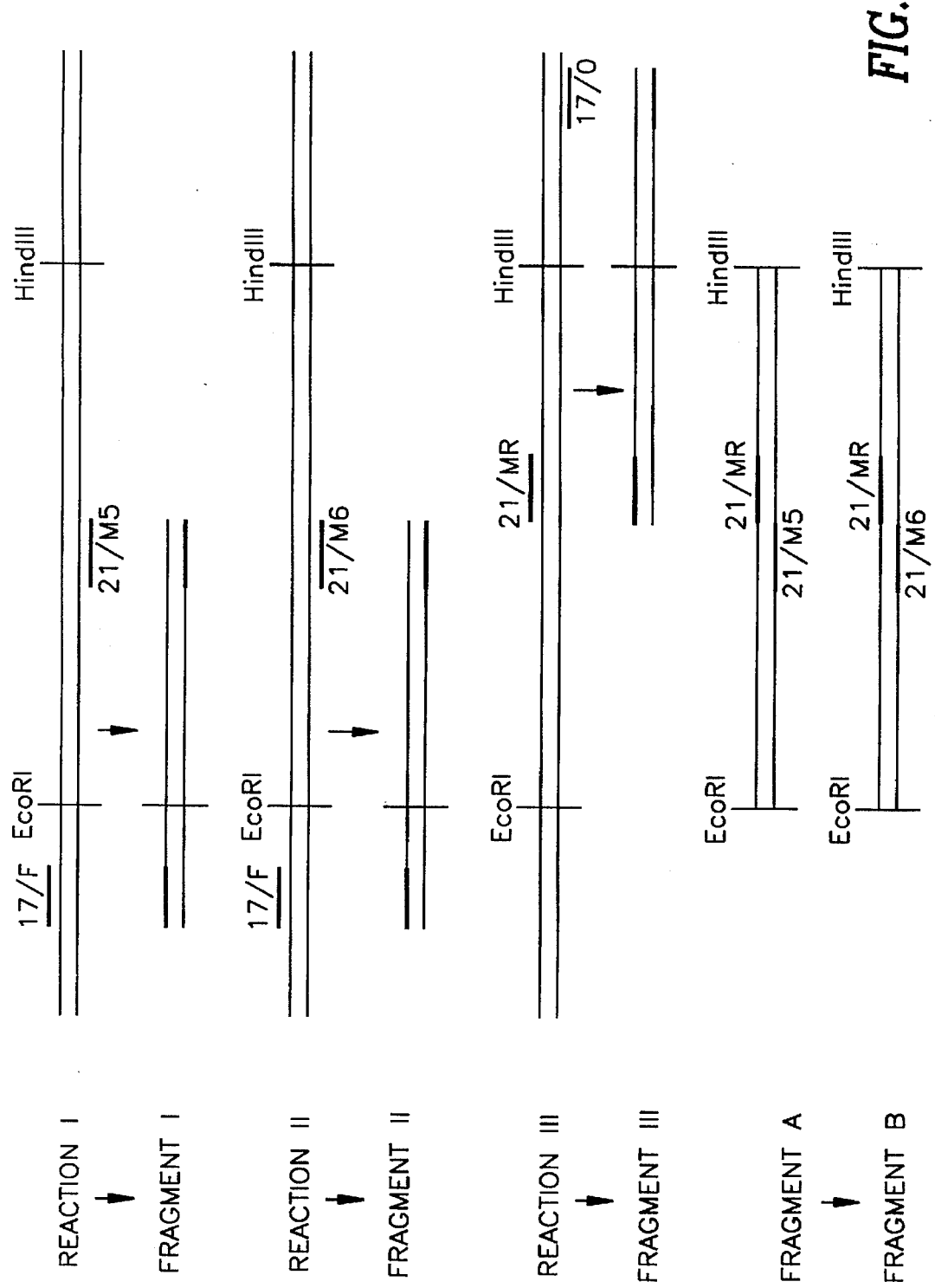
FIG. 11 is a schematic representation of mutagenesis of the TNF β gene using PCR with primers containing the altered codons.

Preparation of Glu$^{31}$-TNFα and Asn$^{31}$-Thr$^{32}$-TNFα
Mutagenesis of the TNFα gene using PCR Three PCR reactions were performed with plasmid pDS56/RBSII,Sph1-TNFα [SEQ ID No: 2][FIGS. 5, 6A–6C] as the template DNA using a Perkin-Elmer Cetus GeneAmp™ DNA Amplification Reagent Kit with Ampli-Taq™ Recombinant Taq DNA Polymerase (Perkin Elmer Cetus, Vaterstetten, BRD) [see FIG. 11]. In reaction I primers 17/F [SEQ ID No: 20](5'-GGCGTATCACGAGGCCCTTTCG-3'; primer 17/F comprises nucleotides 3949–3970 of plasmid pDS56/RBSII, Sph1-TNFα) and 21/M5 [SEQ ID No: 22] (5-ATTGGCCCGCTCGTTCAGCCACTGGAGCTGCCC-CTC-3'; primer 21/M5 comprises nucleotides which are complementary to nucleotides 219–184 of plasmid pDS56/RBSII,Sph1-TNFα, mutated bases are underlined) were used, reaction II contained primers 17/F and 21/M6 [SEQ ID No: 23] (5'-ATTGGCAGTGTTGTTCAGCCA-CTGGAGCTGCCCCTC-3'; primer 21/M6 comprises nucleotides which are complementary to nucleotides 219–184 of plasmid-pDS56/RBSII,Sph1-TNFα, mutated bases are underlined), and reaction III contained primers 21/MR [SEQ ID No: 24] (5'-GCCCTCCTGCCAATGGCGTGG-3'; primer 21/MR comprises nucleotides 220–241 of plasmid pDS56/RBSII,Sph1-TNFα and 17/0 [SEQ ID No: 21] (5'-CATTACTGGATCTATCAACAGG-3'; primer 17/0 comprises nucleotides which are complementary to nucleotides 748–727 of plasmid pDS56/RBSII,Sph1-TNFα). Therfore 10 µl template DNA (10 ng), 5 µl each of the two primers (100 pmole each), 16 µl dNTP's mix (1.25 mM of dATP, dGTP, dCTP, and dTTP), 10 µl 10× reaction buffer (100 mM Tris-HCl pH 8.3, 500 mM KCL, 15 mM MgCl$_2$ and 0.1% gelatin), 1µl (5 units) AmpliTaq™ DNA polymerase and 53 µl H$_2$O were mixed in an Eppendorf tube and overlaid with 80 µl mineral oil (Perkin-Elmer Cetus). The tubes were transferred to a DNA thermal cycler (TRIO-Thermoblock, Biometra) and kept for 1 min at 94° C., before 35 cycles of melting the DNA (1 min at 94° C.), annealing the primers (1 min at 50° C.),and extending the primers (3 min at 72° C.) were performed. After additional 2 min at 72° C., the reactions were cooled to room temperature and extracted with chloroform. The DNA present in the aqueous phase was precipitated with ethanol and subjected to electrophoresis in a 6% polyacrylamide get [Sambrook et al., 1989]. After staining of the DNA with ethidium bromide, fragments I, II and III [see FIG. 11; these fragments originate from reactions I, II and III, respectively] were isolated from the gel and purified [Sambrook et al., 1989].

Preparation of DNA fragments encoding Glu$^{31}$-TNFα and Asn$^{31}$-Thr$^{32}$-TNFα

Fragments I, II and III were enzymatically phosphorylated, before in two parallel reactions fragments I and III and fragments II and III were ligated with each other [Sambrook et al., 1989]. After heat-inactivation of the ligase and digestion with restriction enzymes EcoRI and HindIII, the DNA was subjected to electrophoresis in a 6% polyacrylamide gel. After staining of the DNA with ethidium bromide, the EcoRI-HindIII fragments A and B [see FIG. 7] were isolated from the gel and purified as previously described.

Preparation of plasmids encoding Glu$^{31}$-TNFα and Asn$^{31}$-Thr$^{32}$-TNFα

In separate experiments, the EcoRI-HindIII fragments A and B were inserted according to standard methods [Sambrook et al., 1989] into the EcoRI-HindIII opened plasmid pDS56/RBSII,Sph1-TNFαSer29 generating plasmids pDS56/RBSII,Sph1-TNFαGlu31 and pDS56/RBSII, Sph1-TNFαAsn31Thr32, respectively. Plasmid DNA was prepared [Birnboim et al., 1979] and the identity of .the coding region for the TNFα muteins was confirmed by sequencing the double-stranded DNA [Sambrook et al., 1989].

Production of Glu$^{31}$-TNFα and Asn$^{31}$-Thr$^{32}$-TNFα

Plasmids pDS56/RBSII,Sph1-TNFαGlu31 and pDS56/RBSII,Sph1-TNFαAsn31Thr32 were transformed into E. coli M15 cells containing already plasmid pREP4 by standard methods. Transformed cells were grown at 37° C. in LB medium containing 100 mg/; ampicillin and 25 mg/l kanamycin. At an optical density at 600 nm of about 0.7 to 1.0, IPTG was added to a final concentration of 2 mM. After additional 2.5 to 5 h at 37° C. the cells were harvested by centrifugation.

EXAMPLE VIII

Differential binding to recombinant human D75-TNF-R and recombinant human p55-TNF-R 1. 10 ml suspensions of transformed and induced *E. coli* cells expressing recombinant human TNFα, Ser$^{29}$-TNFα, Trp$^{32}$-TNFα, Glu$^{31}$-TNFα, and Asn$^{31}$-Thr$^{32}$-TNFα[*E. coli* cells expressing recombinant dihydrofolate reductase (DHFR) were included as a control] were centrifuged at 4,000 rpm for 10 min and resuspended in 0.9 ml of lysis buffer (10 mM Tris-HCl pH 8.0, 5 mM EDTA, 2 mM PMSF, 10 mM benzidine, 200 units/ml aprotinine and 0.1 mg/ml lysozyme). After 20 min incubation at room temperature 50 µl of 1M MgCl$_2$, 20 µl of 5 mg/ml DNase1, 50 µl 5M NaCl and 50 µl of 10% NP-40 were added and the mixture was further incubated at room temperature for 15 min. 0.5. ml of the lysate clarified by centrifugation at 13,000 rpm for 5 min was subjected to ammonium sulfate precipitation (30%–70% cut). The 70% ammonium sulfate pellet was dissolved in 0.2 ml PBS and analyzed by SDS-PAGE to confirm the presence of the recombinant proteins.

For the differential binding assay microtiter plates were coated with recombinant human p75-TNF-R-human IgGγ3 p55-TNF-R-human IgGγ3 fusion proteins (European Patent Applications Publ. Nos. 417 563, 422 339) dissolved in PBS at 0.3 µg/ml and 0.1 µg/ml, respectively, (100 µl/well, overnight at 4° C.). After blocking with blocking buffer (50 mM Tris pH 7.4, 140 mM NaCl, 5 mM EDTA, 0.02%, NAN$_3$, 1% defatted milk powder) the microtiter plate was washed With PBS and incubated with 5 ng/ml human $^{125}$I-TNFα (labelled by the Iodogen method to a specific activity of about 30 µCi/µg as described above) in the presence of different dilutions of the *E. coli* lysate partially purified by ammonium sulfate precipitation. The volume was 100 µl/well and each dilution was assayed in duplicate. After three hours at room temperature the wells were thoroughly washed with PBS and counted in a γ-counter. Results are shown in FIGS. 9A–9F whereby closed circles refer to binding to p55-TNF-R-human IgGγ3- and open circles refer to binding to p75-TNF-R-human IgGγ3.

2. Determination of binding of Ser$^{29}$-Trp$^{32}$-TNFα, Gly$^{29}$-TNFα, Tyr$^{29}$-TNFα and Tyr$^{32}$-TNFα was performed as described under 1. with the only exception that MONO-Q ion exchange chromatography purified muteins were used. Results are shown in FIGS. 10A–10E whereby open and closed circles have the same meaning as in FIGS. 9A–9F and µg/ml gives the amount of purified mutein/ml.

---

We claim:

1. A purified and isolated DNA coding for a human Tumor Necrosis Factor-alpha mutein which is at least ten times more selective for human p55 Tumor Necrosis Factor Receptor than for human p75 Tumor Necrosis Factor Receptor, wherein the mutein comprises SEQ ID No: 1 changed by amino acid substitution of at least one of position 29, 31 or 32; and wherein amino acid residue 32 is Trp, Tyr, Thr or Gln.

2. An expression vector suitable for producing, when stably transformed or transfected in a prokaryotic or lower eukaryotic host cell a human Tumor Necrosis Factor-alpha mutein which is at least ten times more selective for human p55 Tumor Necrosis Factor Receptor than for human p75 Tumor Necrosis Factor Receptor, wherein the vector comprises the DNA of claim 1.

3. A prokaryotic or lower eukaryotic host cell stably transformed or transfected with the vector of claim 2.

4. The host cell of claim 3 wherein the host cell is *E. coli*.

* * * * *